US009605022B2

(12) United States Patent
Borzilleri et al.

(10) Patent No.: US 9,605,022 B2
(45) Date of Patent: *Mar. 28, 2017

(54) MACROCYCLIC COMPOUNDS FOR INHIBITION OF INHIBITORS OF APOPTOSIS

(71) Applicant: Ensemble Therapeutics Corporation, Cambridge, MA (US)

(72) Inventors: Robert M. Borzilleri, Princeton, NJ (US); Yong Zhang, Princeton, NJ (US); Michael Miller, Princeton, NJ (US); Andrew Fraley, Arlington, MA (US)

(73) Assignee: Ensemble Therapeutics Corporation, Cambridge, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/441,807

(22) PCT Filed: Nov. 7, 2013

(86) PCT No.: PCT/US2013/068856
§ 371 (c)(1),
(2) Date: May 8, 2015

(87) PCT Pub. No.: WO2014/074665
PCT Pub. Date: May 15, 2014

(65) Prior Publication Data
US 2015/0284427 A1    Oct. 8, 2015

Related U.S. Application Data

(60) Provisional application No. 61/724,577, filed on Nov. 9, 2012.

(51) Int. Cl.
*C07K 7/06* (2006.01)
*A61K 38/08* (2006.01)
*A61K 45/06* (2006.01)

(52) U.S. Cl.
CPC ............... *C07K 7/06* (2013.01); *A61K 38/08* (2013.01); *A61K 45/06* (2013.01)

(58) Field of Classification Search
None
See application file for complete search history.

(56) References Cited

U.S. PATENT DOCUMENTS

2014/0135270 A1* 5/2014 Borzilleri ............. C07D 471/08
514/18.9

FOREIGN PATENT DOCUMENTS

WO    2013/071035 A1    5/2013

OTHER PUBLICATIONS

Nikolovska-Coleska, Zaneta et al, "Interaction of a cyclic, bivalent smac mimetic with the x-llinked inhibitor of apoptosis protein." Biochem. (2008) 47 p. 9811-9824.*
Le Quement, Sebastian T. et al, "Solid-phase synthesis of smac peptidomimetics incorporating triazoloprolines and biarylalanines." ACS Combi. Sci. (2011) 13 p. 667-675.*
Brewster, Keith and Pinder, Roger Martin, "Tetrazole analogues of phenylalanine." Eur. J. Med. Chem. (1975) 10(2) p. 117-120.*
Liu, Zhihong et al, "Structural basis for binding of smac/diablo to the xiap bir3 domain." Nature (2000) 408 p. 1004-1008.*
Oost, Thorstein K. et al, "Discovery of potent antagonists of the antiapoptoti protein xiap for the treatment of cancer." J. Med. Chem. (2004) 47 p. 4417-4426.*
Nokolovska-Coleska, Zaneta et al, "Interaction of a cyclic, bivalent smac mimetic with the x-linked inhibitor of apoptosis protein." Biochem. (2008) 47 p. 9811-9824.*
Hein, Christopher D. et al, "Click chemistry, a powerful tool for pharmaceutical sciences." Pharma. Res. (2008) 25(10) p. 2216-2230.*
Le Quement, Sebastian T. et al, "Solid phase synthesis of smac peptidomimetics incorporating triazoloprolines and biarylalanines." ACS Comb. Sci. (2011) 13 p. 667-675.*
Deiters, Alexander et al, "Adding amino acids with novel reactivity to the genetic code of *Saccaromyces cerevisiae*." J. Am. Chem. Soc. (2003) 125(39) p. 11782-11783.*
Oost et al., "Discovery of Potent Antagonists of the Antiapoptotic Protein Xiap for the Treatment of Cancer", Journal of Medicinal Chemistry, American Chemical Society, US, vol. 47, pp. 4417-4426 (2004).
International Preliminary Report on Patentability for corresponding International Application No. PCT/US2013/068856 dated May 12, 2015.

* cited by examiner

*Primary Examiner* — Fred Reynolds
(74) *Attorney, Agent, or Firm* — McCarter & English, LLP; Steven G. Davis; Mei Bai

(57) ABSTRACT

There are disclosed compounds that modulate the activity of inhibitors of apoptosis (IAPs), pharmaceutical compositions containing said compounds and methods of treating proliferative disorders and disorders of dysregulated apoptosis, such as cancer, utilizing the compounds of the invention.

11 Claims, No Drawings

MACROCYCLIC COMPOUNDS FOR INHIBITION OF INHIBITORS OF APOPTOSIS

CROSS-REFERENCE TO RELATED APPLICATIONS

This application is a 35 U.S.C. §371 national stage filing of International Application No. PCT/US2013/068856, filed on Nov. 7, 2013, which claims the benefit of U.S. Provisional Application No. 61/724,577, filed on Nov. 9, 2012. The contents of the foregoing applications are hereby incorporated by reference in their entirety.

FIELD OF THE INVENTION

The invention relates generally to macrocyclic compounds that modulate the activity of inhibitors of apoptosis (IAPs), pharmaceutical compositions containing said compounds and methods of treating proliferative disorders and disorders of dysregulated apoptosis, such as cancer, utilizing the compounds of the invention.

BACKGROUND OF THE INVENTION

Apoptosis or programmed cell death is a genetically and biochemically regulated mechanism that plays an important role in development and homeostasis in invertebrates as well as vertebrates.

Aberrancies in apoptosis that lead to premature cell death have been linked to a variety of developmental disorders. Deficiencies in apoptosis that result in the lack of cell death have been linked to cancer and chronic viral infections.

Caspases are cysteine-containing aspartate specific proteases that play a key role in effecting apoptosis. Once activated from their inactive zymogen form by proteolytic processing, caspases digest vital cell proteins from within the cell. Since caspases are such strong proteases, tight control of this family of proteins is necessary to prevent premature cell death. In addition to proteolytic processing, caspases are also regulated by a family of molecules known as Inhibitors of Apoptosis Proteins (IAP). IAPs are naturally occurring intra-cellular proteins that suppress caspase-dependent apoptosis. SMAC, an intracellular protein also known as DIABLO, functions to modulate the activity of IAPs. In normal healthy cells, SMAC and IAPs function together to maintain healthy cells. However, in certain disease states, e.g., cancers and other proliferative disorders, the activities of IAPs are not adequately modulated and therefore, prevent apoptosis and cause or exacerbate abnormal proliferation and survival.

IAP antagonists, also known as SMAC mimetics, are synthetic molecules that mimic the structure and IAP modulating activity of the four N-terminal amino acids of SMAC (AVPI). When administered to a subject suffering proliferative disorders, the compounds antagonize IAP activities causing an increase in apoptosis among abnormally proliferating cells.

IAPs are found in all organisms ranging from *Drosophila* to human and are known to be overexpressed in many human cancers. IAPs comprise one to three Baculovirus IAP repeat (BIR) domains. The BIR domain is a zinc binding domain of about 70 residues comprising 4 alpha-helices and 3 beta strands, with cysteine and histidine residues that coordinate the zinc ion. The BIR 2 and 3 domains contain a conserved inhibitor of apoptosis binding motif (IBM) capable of binding caspases—and inhibiting their proteolytic activity.

As an example, human X-chromosome linked IAP (XIAP) inhibits the executioner caspases-3, and -7 as well as the Apaf-1-cytochrome C mediated activation of the initiator caspase-9. Caspases-3 and -7 are inhibited by the BIR2 domain of XIAP, while the BIR3 domain of XIAP is responsible for the inhibition of caspase-9 activation. XIAP is expressed ubiquitously in most adult and fetal tissues. Overexpression of XIAP in tumor cells has been demonstrated to confer protection of the tumor cells against a variety of pro-apoptotic stimuli and promotes resistance to chemotherapy. Consistent with this, a strong correlation between XIAP protein levels and survival has been demonstrated for patients with acute myelogenous leukemia.

Other BIR2-3 containing IAP family members, while capable of binding caspases, do not directly inhibit their proteolytic activity. Rather they inhibit apoptosis by affecting signaling activities of key proteins in cell survival pathways. Like XIAP, these IAPs possess a carboxyl-terminal RING finger domain capable of conjugating ubiquitin to specific protein substrates. As an example, cellular IAPs 1 and 2 (cIAP1/2), ubiquitinate RIPK, a signaling intermediate of tumor necrosis death receptor (TNF-DR) activation. Ubiquitinated RIPK is unable to activate caspase-8 in the context of DR activation by TNF family DR ligands. On the contrary, the long ubiquitin chains attached to RIPK provide a scaffold by which cell components of the NFkB cell survival signaling cascade can attach and become activated.

In normal cells undergoing apoptosis, the IAP-mediated inhibition is removed by the mitochondrial protein SMAC (second mitochondrial activator of caspases; also known as DIABLO). SMAC is synthesized as a precursor molecule of 239 amino acids; the N-terminal 55 residues serving as the mitochondria targeting sequence that is removed after import. The mature form of SMAC resides in the intermembrane space of mitochondria. At the time of apoptosis induction, SMAC is released from mitochondria into the cytosol where, together with cytochrome c, it binds to XIAP, and eliminates its' inhibitory effect on caspases. SMAC also binds cIAP1/2 and inhibits their ability to ubiquitinate RIPK. SMAC interacts with essentially all IAPs that have been examined to date and thus appears to be a master regulator of apoptosis in mammals.

Down-regulation of XIAP expression by antisense oligonucleotides has been shown to sensitize tumor cells to death induced by a wide range of pro-apoptotic agents, both in vitro and in vivo. SMAC/DIABLO-derived peptides have also been demonstrated to sensitize a number of different tumor induced select cell lines to undergo apoptosis as single agents, while other cell lines require an additional stimulus such as DR agonists or co-treatment with pro-apoptotic drugs. Because IAP inhibition appears to be a viable mechanism for promoting apoptosis and treating diseases and conditions that are sensitive to apoptosis, there is a continuing need to develop compounds that can inhibit IAP.

SUMMARY OF THE INVENTION

The present invention provides compounds, methods of modulating the activity of IAP, and methods for treating various medical conditions using such compounds.

The present invention also provides processes and intermediates for making the compounds of the present invention or stereoisomers, tautomers or pharmaceutically acceptable salts thereof.

The present invention also provides pharmaceutical compositions comprising a pharmaceutically acceptable carrier and one or more of the compounds of the present invention or stereoisomers, tautomers or pharmaceutically acceptable salts thereof.

The compounds of the invention may be used in the treatment and/or prophylaxis of multiple diseases or disorders associated with IAP inhibition, such as cancer and other maladies.

The compounds of the invention may be used in therapy.

The compounds of the invention may be used for the manufacture of a medicament for the treatment and/or prophylaxis of multiple diseases or disorders associated with IAP inhibition.

The compounds of the invention can be used alone, in combination with other compounds of the present invention, or in combination with one or more other agent(s).

Other features and advantages of the invention will be apparent from the following detailed description and claims.

DETAILED DESCRIPTION OF THE INVENTION

I. Compounds of the Invention

In a first aspect, the invention provides a compound of Formula (I):

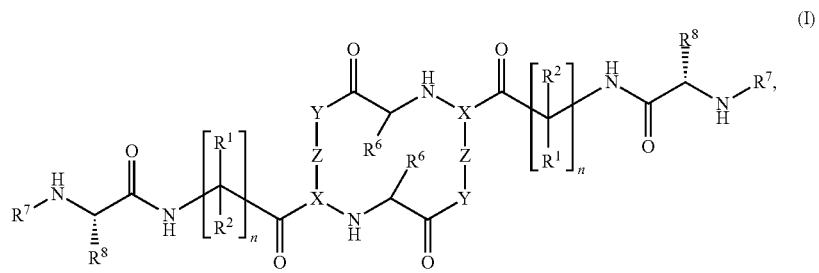

including pharmaceutically acceptable salts thereof, wherein the variables are as defined in the detailed description, wherein:

each n is independently 1 or 2;

each $R^1$ is independently hydrogen, $C_1$-$C_4$ alkyl, cycloalkyl or —($C_1$-$C_4$ alkylene)-$R^4$, wherein each $R^4$ is independently hydrogen, aryl, or cycloalkyl, wherein at least one $R^1$ is other than hydrogen; and each $R^2$ is hydrogen; or $R^1$ and $R^2$ are taken together with the carbon atom to which they are commonly bound to form a cycloalkyl;

each $R^6$ is independently —($C_1$-$C_4$ alkylene)-$R^9$, wherein each $R^9$ is independently selected from hydrogen, aryl, heteroaryl and cycloalkyl; wherein any aryl, heteroaryl or cycloalkyl portion of $R^6$ is optionally substituted with up to two substituents independently selected from halo, $CF_3$, OH, $C_1$-$C_4$ alkoxy, $C_1$-$C_4$ alkenyloxy, phenyl, phenyloxy, and phenylmethyloxy; and wherein one —$CH_2$— in the —($C_1$-$C_4$ alkylene)-portion of $R^6$ is optionally replaced with —O—;

each $R^7$ is independently hydrogen or $C_1$-$C_4$ alkyl;

each $R^8$ is independently $C_1$-$C_4$ alkyl;

each X is independently selected from:

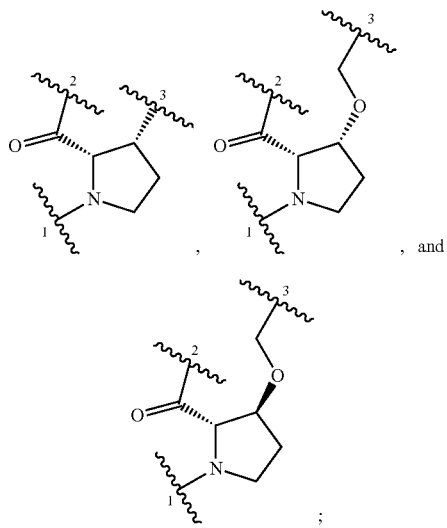

, and each Z is:

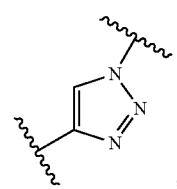

, wherein each -| represents a point of attachment to the compound;

each Y is independently selected from:

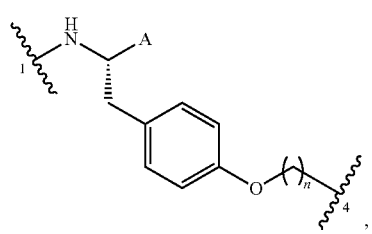

, n = 1-3

-continued

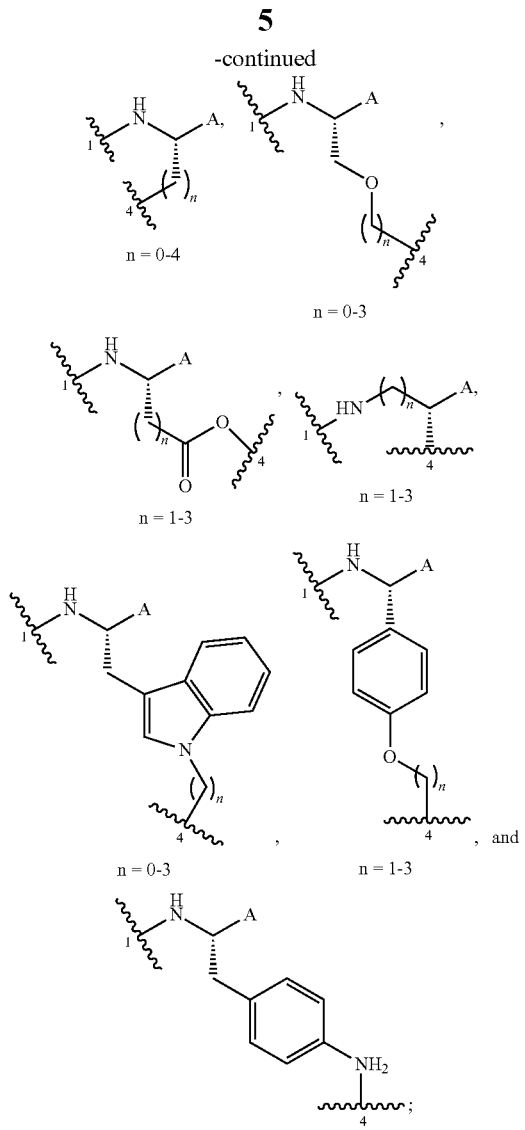

wherein:
- -|¹ represents a point of attachment to a —C=O portion of the compound;
- -|² represents a point of attachment to a —NH portion of the compound;
- -|³ represents a first point of attachment to Z;
- -|⁴ represents a second point of attachment to Z; and A is selected from —C(O)R³ or

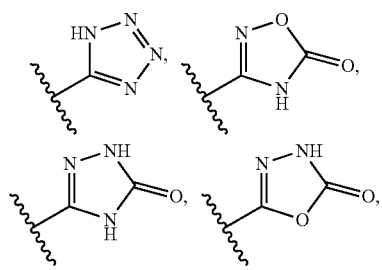

-continued

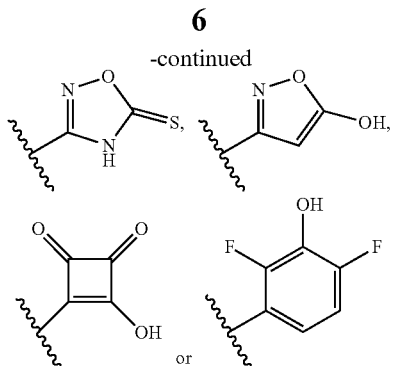

(including the various tautomeric forms);

$R^3$ is OH, NHCN, NHSO$_2$R$^{10}$, NHOR$^{11}$ or N(R$^{12}$)(R$^{13}$);

$R^{10}$ and $R^{11}$ are selected from hydrogen, optionally substituted: —C$_1$-C$_4$ alkyl, cycloalkyl, aryl, heteroaryl, heterocyclyl or heterocycloalkyl;

each of $R^{12}$ and $R^{13}$ are independently selected from hydrogen, —C$_1$-C$_4$ alkyl, —(C$_1$-C$_4$ alkylene)-NH—(C$_1$-C$_4$ alkyl), and —(C$_1$-C$_4$ alkylene)-O—(C$_1$-C$_4$ hydroxyalkyl), or $R^{12}$ and $R^{13}$ are taken together with the nitrogen atom to which they are commonly bound to form a saturated heterocyclyl optionally comprising one additional heteroatom selected from N, O and S, and wherein the saturated heterocycle is optionally substituted with methyl.

In a second aspect, the invention provides a compound of Formula (I) within the scope of the first aspect, wherein each $R^1$ is independently C$_1$-C$_4$ alkyl;

each $R^6$ is independently —(C$_1$-C$_4$ alkylene)-R$^9$, wherein each $R^9$ is independently selected from hydrogen, aryl and heteroaryl;

each $R^7$ is independently selected from hydrogen and methyl;

each $R^8$ is independently selected from methyl and ethyl;

each Y is independently

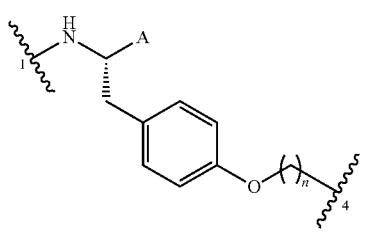

A is —C(O)R³ or

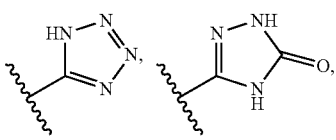

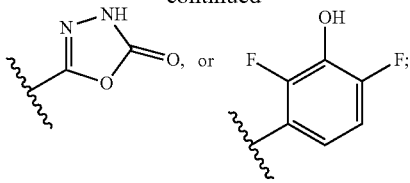

and

R$^3$ is R$^3$ is OH, NHSO$_2$R$^{16}$ or N(R$^{12}$)(R$^{13}$);

and/or a pharmaceutically acceptable salt thereof.

In a third aspect, the invention provides a compound of Formula (I) within the scope of the first or second aspect, wherein each R$^1$ is independently t-butyl;

each R$^6$ is independently —(C$_1$-C$_4$ alkylene)-R$^9$, wherein each R$^9$ is aryl;

each R$^7$ is independently selected from hydrogen and methyl;

each R$^8$ is independently selected from methyl and ethyl each Y is independently

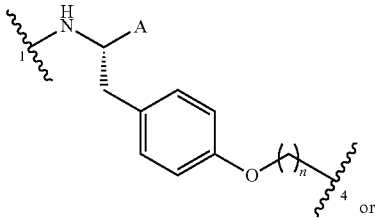

n = 1-3 or

A is —C(O)R$^3$ or

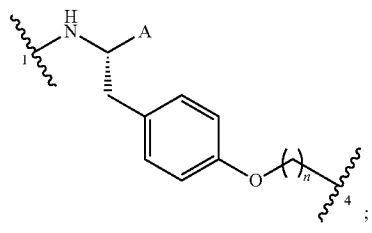

and

R$^3$ is R$^3$ is OH, NHSO$_2$R$^{16}$ or N(R$^{12}$)(R$^{13}$);

and/or a pharmaceutically acceptable salt thereof.

In a fourth aspect, the invention provides a compound of Formula (I) within the scope of the first, second or third aspect, wherein:

each R$^6$ is independently —(C$_1$-C$_4$ alkylene)-R$^9$, wherein each R$^9$ is naphthalenyl;

each R$^7$ is methyl;

each R$^8$ is methyl;

each Y is independently

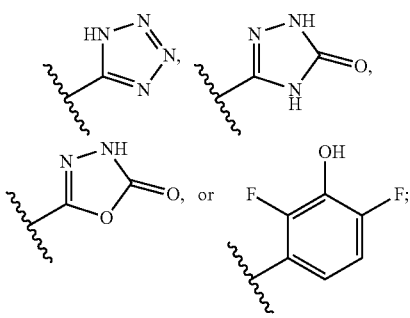

n = 1-3 n = 0-4

A is —C(O)R$^3$ or

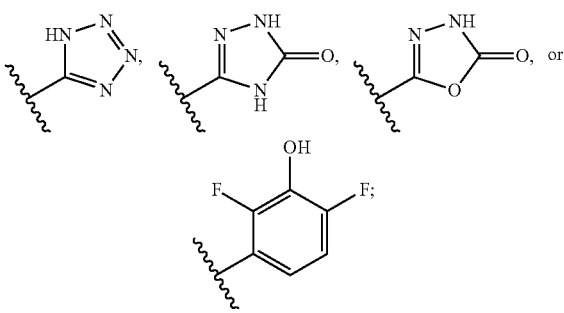

and

R$^3$ is R$^3$ is OH, NHSO$_2$R$^{10}$ or N(R$^{12}$)(R$^{13}$);

and/or a pharmaceutically acceptable salt thereof.

In another aspect, the invention provides a compound selected from the exemplified examples within the scope of the first aspect, or a pharmaceutically acceptable salt, tautomer or stereoisomer thereof.

In another aspect, the invention provides a compound selected from any subset list of compounds within the scope of any of the above aspects.

In another embodiment, the compounds of the invention have BIR3 IC$_{50}$ values ≤0.10.

In another embodiment, the compounds of the invention have BIR3 IC$_{50}$ values ≤0.050.

In another embodiment, the compounds of the invention have BIR3 IC$_{50}$ values ≤0.020.

In another embodiment, the compounds of the invention have BIR3 IC$_{50}$ values ≤0.0050.

In another embodiment, the compounds of the invention have BIR2-3 IC$_{50}$ values ≤0.025.

In another embodiment, the compounds of the invention have BIR2-3 IC$_{50}$ values ≤0.010.

In another embodiment, the compounds of the invention have BIR2-3 IC$_{50}$ values ≤0.0050.

In another embodiment, the compounds of the invention have BIR2-3 IC$_{50}$ values ≤0.0010.

II. Other Embodiments of the Invention

In another embodiment, the present invention provides a composition comprising one or more compounds of the present invention or a stereoisomer, a tautomer, a pharmaceutically acceptable salt, or a solvate thereof.

In another embodiment, the present invention provides a pharmaceutical composition comprising a pharmaceutically acceptable carrier and at least one of the compounds of the present invention or a stereoisomer, a tautomer, a pharmaceutically acceptable salt, or a solvate thereof.

In another embodiment, the present invention provides a pharmaceutical composition, comprising: a pharmaceutically acceptable carrier and a therapeutically effective amount of at least one of the compounds of the present invention or a stereoisomer, a tautomer, a pharmaceutically acceptable salt, or a solvate thereof.

In another embodiment, the present invention provides a process for making a compound of the present invention or a stereoisomer, a tautomer, a pharmaceutically acceptable salt, or a solvate thereof.

In another embodiment, the present invention provides an intermediate for making a compound of the present invention or a stereoisomer, a tautomer, a pharmaceutically acceptable salt, or a solvate thereof.

In another embodiment, the present invention provides a method for the treatment and/or prophylaxis of various types of cancer, comprising administering to a patient in need of such treatment and/or prophylaxis a therapeutically effective amount of one or more compounds of the present invention, alone, or, optionally, in combination with another compound of the present invention and/or at least one other type of therapeutic agent.

In another embodiment, the present invention provides a compound of the present invention for use in therapy.

In another embodiment, the present invention provides a combined preparation of a compound of the present invention and additional therapeutic agent(s) for simultaneous, separate or sequential use in therapy.

In another embodiment, the present invention provides a combined preparation of a compound of the present invention and additional therapeutic agent(s) for simultaneous, separate or sequential use in the treatment and/or prophylaxis of multiple diseases or disorders associated with the inhibition of apoptosis.

In another aspect, the invention provides a method of treating a patient suffering from or susceptible to a medical condition that is sensitive to apoptosis. A number of medical conditions can be treated. The method comprises administering to the patient a therapeutically effective amount of a composition comprising a compound described herein. For example, the compounds described herein may be used to treat or prevent infections, proliferative diseases (e.g., cancer), and autoimmune diseases.

In another aspect, the invention provides a method of inhibiting the activity of an IAP in a cell, thus promoting apoptosis. The method comprises exposing the cell to a compound described herein.

III. Therapeutic Applications

The compounds and pharmaceutical compositions of the present invention are useful in treating or preventing any disease or conditions that are sensitive to apoptosis. These include infections (e.g. skin infections, GI infection, urinary tract infections, genito-urinary infections, systemic infections), proliferative diseases (e.g., cancer), and autoimmune diseases (e.g., rheumatoid arthritis, lupus). The compounds and pharmaceutical compositions may be administered to animals, preferably mammals (e.g., domesticated animals, cats, dogs, mice, rats), and more preferably humans. Any method of administration may be used to deliver the compound or pharmaceutical composition to the animal. In certain embodiments, the compound or pharmaceutical composition is administered orally. In other embodiments, the compound or pharmaceutical composition is administered parenterally.

In one embodiment, the compounds of this invention can be used for the treatment of any cancer type that fails to undergo apoptosis in a patient. This includes, but is not limited to: solid tumors, including but not limited to carcinomas; sarcomas including Kaposi's sarcoma; erythroblastoma; glioblastoma; meningioma; astrocytoma; melanoma; and myoblastoma. Treatment or prevention of non-solid tumor cancers, such as leukemia, is also contemplated by this invention.

Types of cancers that may be treated with the compounds of this invention include, but are not limited to, brain cancers, skin cancers, bladder cancers, ovarian cancers, breast cancers, gastric cancers, pancreatic cancers, prostate cancers, colon cancers, blood cancers, lung cancers and bone cancers. Examples of such cancer types include neuroblastoma, intestine carcinoma such as rectum carcinoma, colon carcinoma, familiar adenomatous polyposis carcinoma and hereditary non-polyposis colorectal cancer, esophageal carcinoma, labial carcinoma, larynx carcinoma, hypopharynx carcinoma, tong carcinoma, salivary gland carcinoma, gastric carcinoma, adenocarcinoma, medullary thyroid carcinoma, papillary thyroid carcinoma, renal carcinoma, kidney parenchymal carcinoma, ovarian carcinoma, cervix carcinoma, uterine corpus carcinoma, endometrium carcinoma, chorion carcinoma, pancreatic carcinoma, prostate carcinoma, testis carcinoma, breast carcinoma, urinary carcinoma, melanoma, brain tumors such as glioblastoma, astrocytoma, meningioma, medulloblastoma and peripheral neuroectodermal tumors, Hodgkin lymphoma, non-Hodgkin lymphoma, Burkitt lymphoma, acute lymphatic leukemia (ALL), chronic lymphatic leukemia (CLL), acute myeloid leukemia (AML), chronic myeloid leukemia (CML), adult T-cell leukemia lymphoma, diffuse large B-cell lymphoma (DLBCL), hepatocellular carcinoma, gall bladder carcinoma, bronchial carcinoma, small cell lung carcinoma, non-small cell lung carcinoma, multiple myeloma, basalioma, teratoma, retinoblastoma, choroid melanoma, seminoma, rhabdomyosarcoma, craniopharyngioma, osteosarcoma, chondrosarcoma, myosarcoma, liposarcoma, fibrosarcoma, Ewing sarcoma and plasmocytoma.

In addition to apoptosis defects found in tumors, defects in the ability to eliminate self-reactive cells of the immune system due to apoptosis resistance are considered to play a key role in the pathogenesis of autoimmune diseases. Autoimmune diseases are characterized in that the cells of the immune system produce antibodies against its own organs and molecules or directly attack tissues resulting in the destruction of the latter. A failure of those self-reactive cells to undergo apoptosis leads to the manifestation of the disease. Defects in apoptosis regulation have been identified in autoimmune diseases such as systemic lupus erythematosus or rheumatoid arthritis.

Thus, according to another embodiment, the invention provides a method of treating an autoimmune disease by providing to a patient in need thereof a compound or composition of the present invention. Examples of such autoimmune diseases include, but are not limited to, collagen diseases such as rheumatoid arthritis, systemic lupus erythematosus. Sharp's syndrome, CREST syndrome (calcinosis, Raynaud's syndrome, esophageal dysmotility, telangiectasia), dermatomyositis, vasculitis (Morbus Wegener's) and Sjogren's syndrome, renal diseases such as Goodpasture's syndrome, rapidly-progressing glomerulonephritis and membrano-proliferative glomerulonephritis type II, endocrine diseases such as type-I diabetes, autoimmune polyendocrinopathy-candidiasis-ectodermal dystrophy (APECED), autoimmune parathyroidism, pernicious anemia, gonad insufficiency, idiopathic Morbus Addison's, hyperthyreosis, Hashimoto's thyroiditis and primary myxedema, skin diseases such as *pemphigus vulgaris*, bullous pemphigoid, herpes gestationis, epidermolysis bullosa and erythema multiforme major, liver diseases such as primary biliary cirrhosis, autoimmune cholangitis, autoimmune hepatitis type-1, autoimmune hepatitis type-2, primary sclerosing cholangitis, neuronal diseases such as multiple sclerosis, myasthenia gravis, myasthenic Lambert-Eaton syndrome, acquired neuromyotomy, Guillain-Barre syndrome (Muller-Fischer syndrome), stiff-man syndrome, cerebellar degeneration, ataxia, opsoclonus, sensoric neuropathy and achalasia, blood diseases such as autoimmune hemolytic anemia, idiopathic thrombocytopenic purpura (Morbus Werlhof), infectious diseases with associated autoimmune reactions such as AIDS, Malaria and Chagas disease.

Compounds of the invention are useful for sensitizing cells to apoptotic signals. Thus, in one embodiment, the compounds of the invention are co-administered with radiation therapy or a second therapeutic agent with cytostatic or antineoplastic activity. Suitable cytostatic chemotherapy compounds include, but are not limited to (i) antimetabolites; (ii) DNA-fragmenting agents, (iii) DNA-crosslinking agents, (iv) intercalating agents (v) protein synthesis inhibitors, (vi) topoisomerase I poisons, such as camptothecin or topotecan; (vii) topoisomerase II poisons, (viii) microtubule-directed agents, (ix) kinase inhibitors (x) miscellaneous investigational agents (xi) hormones and (xii) hormone antagonists. It is contemplated that compounds of the invention may be useful in combination with any known agents falling into the above 12 classes as well as any future agents that are currently in development. In particular, it is contemplated that compounds of the invention may be useful in combination with current Standards of Care as well as any that evolve over the foreseeable future. Specific dosages and dosing regimens would be based on physicians' evolving knowledge and the general skill in the art.

The combination therapy is intended to embrace administration of these therapeutic agents in a sequential manner, that is, wherein each therapeutic agent is administered at a different time, as well as administration of these therapeutic agents, or at least two of the therapeutic agents, in a substantially simultaneous manner. Substantially simultaneous administration can be accomplished, for example, by administering to the subject a single dosage form having a fixed ratio of each therapeutic agent or in multiple, single dosage forms for each of the therapeutic agents. Sequential or substantially simultaneous administration of each therapeutic agent can be effected by any appropriate route including, but not limited to, oral routes, intravenous routes, intramuscular routes, and direct absorption through mucous membrane tissues. The therapeutic agents can be administered by the same route or by different routes. For example, a first therapeutic agent of the combination selected may be administered by intravenous injection while the other therapeutic agents of the combination may be administered orally. Alternatively, for example, all therapeutic agents may be administered orally or all therapeutic agents may be administered by intravenous injection. Combination therapy also can embrace the administration of the therapeutic agents as described above in further combination with other biologically active ingredients and non-drug therapies (e.g., surgery or radiation treatment.) Where the combination therapy further comprises a non-drug treatment, the non-drug treatment may be conducted at any suitable time so long as a beneficial effect from the co-action of the combination of the therapeutic agents and non-drug treatment is achieved. For example, in appropriate cases, the beneficial effect is still achieved when the non-drug treatment is temporally removed from the administration of the therapeutic agents, perhaps by days or even weeks.

IV. Pharmaceutical Compositions and Dosing

The invention also provides pharmaceutically acceptable compositions which comprise a therapeutically effective amount of one or more of the compounds of Formula I, formulated together with one or more pharmaceutically acceptable carriers (additives) and/or diluents, and optionally, one or more additional therapeutic agents described above. As described in detail below, the pharmaceutical compositions of the present invention may be specially formulated for administration in solid or liquid form, including those adapted for the following: (1) oral administration, for example, drenches (aqueous or nonaqueous solutions or suspensions), tablets, e.g., those targeted for buccal, sublingual, and systemic absorption, boluses, powders, granules, pastes for application to the tongue; (2) parenteral administration, for example, by subcutaneous, intramuscular, intravenous or epidural injection as, for example, a sterile solution or suspension, or sustained release formulation; (3) topical application, for example, as a cream, ointment, or a controlled release patch or spray applied to the skin; (4) intravaginally or intrarectally, for example, as a pessary, cream or foam; (5) sublingually; (6) ocularly; (7) transdermally; or (8) nasally.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The phrase "pharmaceutically acceptable carrier" as used herein means a pharmaceutically acceptable material, composition or vehicle, such as a liquid or solid filler, diluent, excipient, manufacturing aid (e.g., lubricant, talc magnesium, calcium or zinc stearate, or steric acid), or solvent encapsulating material, involved in carrying or transporting the subject compound from one organ, or portion of the body, to another organ, or portion of the body. Each carrier must be "acceptable" in the sense of being compatible with the other ingredients of the formulation and not injurious to the patient. Some examples of materials which can serve as pharmaceutically acceptable carriers include: (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) pH buffered solutions; (21) polyesters, polycarbonates and/or polyanhydrides; and (22) other non-toxic compatible substances employed in pharmaceutical formulations.

Wetting agents, emulsifiers and lubricants, such as sodium lauryl sulfate and magnesium stearate, as well as coloring agents, release agents, coating agents, sweetening, flavoring and perfuming agents, preservatives and antioxidants can also be present in the compositions.

Examples of pharmaceutically acceptable antioxidants include: (1) water soluble antioxidants, such as ascorbic acid, cysteine hydrochloride, sodium bisulfate, sodium metabisulfite, sodium sulfite and the like; (2) oil-soluble antioxidants, such as ascorbyl palmitate, butylated hydroxyanisole (BHA), butylated hydroxytoluene (BHT), lecithin, propyl gallate, alpha-tocopherol, and the like; and (3) metal chelating agents, such as citric acid, ethylenediamine tetraacetic acid (EDTA), sorbitol, tartaric acid, phosphoric acid, and the like.

Formulations of the present invention include those suitable for oral, nasal, topical (including buccal and sublingual), rectal, vaginal and/or parenteral administration. The formulations may conveniently be presented in unit dosage form and may be prepared by any methods well known in the art of pharmacy. The amount of active ingredient which can be combined with a carrier material to produce a single dosage form will vary depending upon the host being treated, the particular mode of administration. The amount of active ingredient which can be combined with a carrier material to produce a single dosage form will generally be that amount of the compound which produces a therapeutic effect. Generally, out of one hundred percent, this amount will range from about 0.1 percent to about ninety-nine percent of active ingredient, preferably from about 5 percent to about 70 percent, most preferably from about 10 percent to about 30 percent.

In certain embodiments, a formulation of the present invention comprises an excipient selected from the group consisting of cyclodextrins, celluloses, liposomes, micelle forming agents, e.g., bile acids, and polymeric carriers, e.g., polyesters and polyanhydrides; and a compound of the present invention. In certain embodiments, an aforementioned formulation renders orally bioavailable a compound of the present invention.

Methods of preparing these formulations or compositions include the step of bringing into association a compound of the present invention with the carrier and, optionally, one or more accessory ingredients. In general, the formulations are prepared by uniformly and intimately bringing into association a compound of the present invention with liquid carriers, or finely divided solid carriers, or both, and then, if necessary, shaping the product.

Formulations of the invention suitable for oral administration may be in the form of capsules, cachets, pills, tablets, lozenges (using a flavored basis, usually sucrose and acacia or tragacanth), powders, granules, or as a solution or a suspension in an aqueous or non-aqueous liquid, or as an oil-in-water or water-in-oil liquid emulsion, or as an elixir or syrup, or as pastilles (using an inert base, such as gelatin and glycerin, or sucrose and acacia) and/or as mouth washes and the like, each containing a predetermined amount of a compound of the present invention as an active ingredient. A compound of the present invention may also be administered as a bolus, electuary or paste.

In solid dosage forms of the invention for oral administration (capsules, tablets, pills, dragees, powders, granules, troches and the like), the active ingredient is mixed with one or more pharmaceutically acceptable carriers, such as sodium citrate or dicalcium phosphate, and/or any of the following: (1) fillers or extenders, such as starches, lactose, sucrose, glucose, mannitol, and/or silicic acid; (2) binders, such as, for example, carboxymethylcellulose, alginates, gelatin, polyvinyl pyrrolidone, sucrose and/or acacia; (3) humectants, such as glycerol; (4) disintegrating agents, such as agar-agar, calcium carbonate, potato or tapioca starch, alginic acid, certain silicates, and sodium carbonate; (5) solution retarding agents, such as paraffin; (6) absorption accelerators, such as quaternary ammonium compounds and surfactants, such as poloxamer and sodium lauryl sulfate; (7) wetting agents, such as, for example, cetyl alcohol, glycerol monostearate, and non-ionic surfactants; (8) absorbents, such as kaolin and bentonite clay; (9) lubricants, such as talc, calcium stearate, magnesium stearate, solid polyethylene glycols, sodium lauryl sulfate, zinc stearate, sodium stearate, stearic acid, and mixtures thereof; (10) coloring agents; and (11) controlled release agents such as crospovidone or ethyl cellulose. In the case of capsules, tablets and pills, the pharmaceutical compositions may also comprise buffering agents. Solid compositions of a similar type may also be employed as fillers in soft and hard shelled gelatin capsules using such excipients as lactose or milk sugars, as well as high molecular weight polyethylene glycols and the like.

A tablet may be made by compression or molding, optionally with one or more accessory ingredients. Compressed tablets may be prepared using binder (for example, gelatin or hydroxypropylmethyl cellulose), lubricant, inert diluent, preservative, disintegrant (for example, sodium starch glycolate or cross-linked sodium carboxymethyl cellulose), surface active or dispersing agent. Molded tablets may be made by molding in a suitable machine a mixture of the powdered compound moistened with an inert liquid diluent.

The tablets, and other solid dosage forms of the pharmaceutical compositions of the present invention, such as dragees, capsules, pills and granules, may optionally be scored or prepared with coatings and shells, such as enteric coatings and other coatings well known in the pharmaceutical formulating art. They may also be formulated so as to provide slow or controlled release of the active ingredient therein using, for example, hydroxypropylmethyl cellulose in varying proportions to provide the desired release profile, other polymer matrices, liposomes and/or microspheres. They may be formulated for rapid release, e.g., freeze-dried. They may be sterilized by, for example, filtration through a bacteria retaining filter, or by incorporating sterilizing agents in the form of sterile solid compositions which can be dissolved in sterile water, or some other sterile injectable medium immediately before use. These compositions may also optionally contain opacifying agents and may be of a composition that they release the active ingredient(s) only, or preferentially, in a certain portion of the gastrointestinal tract, optionally, in a delayed manner. Examples of embedding compositions which can be used include polymeric substances and waxes. The active ingredient can also be in micro-encapsulated form, if appropriate, with one or more of the above described excipients.

Liquid dosage forms for oral administration of the compounds of the invention include pharmaceutically acceptable emulsions, microemulsions, solutions, suspensions, syrups and elixirs. In addition to the active ingredient, the liquid dosage forms may contain inert diluents commonly used in the art, such as, for example, water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor and sesame oils), glycerol, tetrahydrofuryl alcohol, polyethylene glycols and fatty acid esters of sorbitan, and mixtures thereof.

Besides inert diluents, the oral compositions can also include adjuvants such as wetting agents, emulsifying and suspending agents, sweetening, flavoring, coloring, perfuming and preservative agents.

Suspensions, in addition to the active compounds, may contain suspending agents as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof.

Formulations of the pharmaceutical compositions of the invention for rectal or vaginal administration may be presented as a suppository, which may be prepared by mixing one or more compounds of the invention with one or more suitable nonirritating excipients or carriers comprising, for example, cocoa butter, polyethylene glycol, a suppository wax or a salicylate, and which is solid at room temperature, but liquid at body temperature and, therefore, will melt in the rectum or vaginal cavity and release the active compound.

Formulations of the present invention which are suitable for vaginal administration also include pessaries, tampons, creams, gels, pastes, foams or spray formulations containing such carriers as are known in the art to be appropriate.

Dosage forms for the topical or transdermal administration of a compound of this invention include powders, sprays, ointments, pastes, creams, lotions, gels, solutions, patches and inhalants. The active compound may be mixed under sterile conditions with a pharmaceutically acceptable carrier, and with any preservatives, buffers, or propellants which may be required.

The ointments, pastes, creams and gels may contain, in addition to an active compound of this invention, excipients, such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to a compound of this invention, excipients such as lactose, talc, silicic acid, aluminum hydroxide, calcium silicates and polyamide powder, or mixtures of these substances. Sprays can additionally contain customary propellants, such as chlorofluorohydrocarbons and volatile unsubstituted hydrocarbons, such as butane and propane.

Transdermal patches have the added advantage of providing controlled delivery of a compound of the present invention to the body. Such dosage forms can be made by dissolving or dispersing the compound in the proper medium. Absorption enhancers can also be used to increase the flux of the compound across the skin. The rate of such flux can be controlled by either providing a rate controlling membrane or dispersing the compound in a polymer matrix or gel.

Ophthalmic formulations, eye ointments, powders, solutions and the like, are also contemplated as being within the scope of this invention.

Pharmaceutical compositions of this invention suitable for parenteral administration comprise one or more compounds of the invention in combination with one or more pharmaceutically acceptable sterile isotonic aqueous or non-aqueous solutions, dispersions, suspensions or emulsions, or sterile powders which may be reconstituted into sterile injectable solutions or dispersions just prior to use, which may contain sugars, alcohols, antioxidants, buffers, bacteriostats, solutes which render the formulation isotonic with the blood of the intended recipient or suspending or thickening agents.

Examples of suitable aqueous and non-aqueous carriers which may be employed in the pharmaceutical compositions of the invention include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

These compositions may also contain adjuvants such as preservatives, wetting agents, emulsifying agents and dispersing agents. Prevention of the action of microorganisms upon the subject compounds may be ensured by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents which delay absorption such as aluminum monostearate and gelatin.

In some cases, in order to prolong the effect of a drug, it is desirable to slow the absorption of the drug from subcutaneous or intramuscular injection. This may be accomplished by the use of a liquid suspension of crystalline or amorphous material having poor water solubility. The rate of absorption of the drug then depends upon its rate of dissolution which, in turn, may depend upon crystal size and crystalline form. Alternatively, delayed absorption of a parenterally administered drug form is accomplished by dissolving or suspending the drug in an oil vehicle.

Injectable depot forms are made by forming microencapsuled matrices of the subject compounds in biodegradable polymers such as polylactide-polyglycolide. Depending on the ratio of drug to polymer, and the nature of the particular polymer employed, the rate of drug release can be controlled. Examples of other biodegradable polymers include poly(orthoesters) and poly(anhydrides). Depot injectable formulations are also prepared by entrapping the drug in liposomes or microemulsions which are compatible with body tissue.

When the compounds of the present invention are administered as pharmaceuticals, to humans and animals, they can be given per se or as a pharmaceutical composition containing, for example, 0.1 to 99% (more preferably, 10 to 30%) of active ingredient in combination with a pharmaceutically acceptable carrier.

Regardless of the route of administration selected, the compounds of the present invention, which may be used in a suitable hydrated form, and/or the pharmaceutical compositions of the present invention, are formulated into pharmaceutically acceptable dosage forms by conventional methods known to those of skill in the art.

Actual dosage levels of the active ingredients in the pharmaceutical compositions of this invention may be varied so as to obtain an amount of the active ingredient which is effective to achieve the desired therapeutic response for a particular patient, composition, and mode of administration, without being toxic to the patient.

The selected dosage level will depend upon a variety of factors including the activity of the particular compound of the present invention employed, or the ester, salt or amide thereof, the route of administration, the time of administration, the rate of excretion or metabolism of the particular compound being employed, the rate and extent of absorption, the duration of the treatment, other drugs, compounds and/or materials used in combination with the particular compound employed, the age, sex, weight, condition, general health and prior medical history of the patient being treated, and like factors well known in the medical arts.

A physician or veterinarian having ordinary skill in the art can readily determine and prescribe the effective amount of the pharmaceutical composition required. For example, the physician or veterinarian could start doses of the compounds of the invention employed in the pharmaceutical composition at levels lower than that required in order to achieve the desired therapeutic effect and gradually increase the dosage until the desired effect is achieved.

In general, a suitable daily dose of a compound of the invention will be that amount of the compound which is the lowest dose effective to produce a therapeutic effect. Such an effective dose will generally depend upon the factors described above. Generally, oral, intravenous, intracerebroventricular and subcutaneous doses of the compounds of this invention for a patient will range from about 0.01 to about 50 mg per kilogram of body weight per day.

If desired, the effective daily dose of the active compound may be administered as two, three, four, five, six or more sub-doses administered separately at appropriate intervals throughout the day, optionally, in unit dosage forms. In certain aspects of the invention, dosing is one administration per day.

While it is possible for a compound of the present invention to be administered alone, it is preferable to administer the compound as a pharmaceutical formulation (composition).

V. Definitions

Throughout the specification and the appended claims, a given chemical formula or name shall encompass all stereo and optical isomers and racemates thereof where such isomers exist. Unless otherwise indicated, all chiral (enantiomeric and diastereomeric) and racemic forms are within the scope of the invention. Many geometric isomers of C=C double bonds, C=N double bonds, ring systems, and the like can also be present in the compounds, and all such stable isomers are contemplated in the present invention. Cis- and trans- (or E- and Z-) geometric isomers of the compounds of the present invention are described and may be isolated as a mixture of isomers or as separated isomeric forms. The present compounds can be isolated in optically active or racemic forms. Optically active forms may be prepared by resolution of racemic forms or by synthesis from optically active starting materials. All processes used to prepare compounds of the present invention and intermediates made therein are considered to be part of the present invention. When enantiomeric or diastereomeric products are prepared, they may be separated by conventional methods, for example, by chromatography or fractional crystallization. Depending on the process conditions the end products of the present invention are obtained either in free (neutral) or salt form. Both the free form and the salts of these end products are within the scope of the invention. If so desired, one form of a compound may be converted into another form. A free base or acid may be converted into a salt; a salt may be converted into the free compound or another salt; a mixture of isomeric compounds of the present invention may be separated into the individual isomers. Compounds of the present invention, free form and salts thereof, may exist in multiple tautomeric forms, in which hydrogen atoms are transposed to other parts of the molecules and the chemical bonds between the atoms of the molecules are consequently rearranged. It should be understood that all tautomeric forms, insofar as they may exist, are included within the invention.

As used herein, the term "alkyl" or "alkylene" is intended to include both branched and straight-chain saturated aliphatic hydrocarbon groups having the specified number of carbon atoms. For example, "$C_1$-$C_6$ alkyl" denotes alkyl having 1 to 6 carbon atoms. Example alkyl groups include, but are not limited to, methyl (Me), ethyl (Et), propyl (e.g., n-propyl and isopropyl), butyl (e.g., n-butyl, isobutyl, t-butyl), and pentyl (e.g., n-pentyl, isopentyl, neopentyl).

The term "alkoxy" or "alkyloxy" refers to an —O-alkyl group. "$C_{1-6}$ alkoxy" (or alkyloxy), is intended to include $C_1$, $C_2$, $C_3$, $C_4$, $C_5$, and $C_6$ alkoxy groups. Example alkoxy groups include, but are not limited to, methoxy, ethoxy, propoxy (e.g., n-propoxy and isopropoxy), and t-butoxy. Similarly, "alkylthio" or "thioalkoxy" represents an alkyl group as defined above with the indicated number of carbon atoms attached through a sulphur bridge; for example methyl-S— and ethyl-S—.

The term "aryl", either alone or in combination with another radical, means a carbocyclic aromatic monocyclic group containing 6 carbon atoms which may be further fused to a second 5- or 6-membered carbocyclic group which may be aromatic, saturated or unsaturated. Aryl includes, but is not limited to, phenyl, indanyl, 1-naphthalenyl, 2-naphthalenyl and terahydronaphthalenyl. The fused aryls may be connected to another group either at a suitable position on the cycloalkyl ring or the aromatic ring. For example:

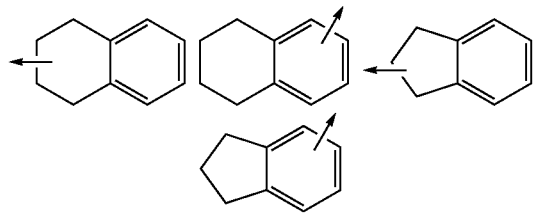

Arrowed lines drawn from the ring system indicate that the bond may be attached to any of the suitable ring atoms.

The term "cycloalkyl" refers to cyclized alkyl groups. $C_{3-6}$ cycloalkyl is intended to include $C_3$, $C_4$, $C_5$, and $C_6$ cycloalkyl groups. Example cycloalkyl groups include, but are not limited to, cyclopropyl, cyclobutyl, cyclopentyl, cyclohexyl, and norbornyl. Branched cycloalkyl groups such as 1-methylcyclopropyl and 2-methylcyclopropyl are included in the definition of "cycloalkyl". The term "cycloalkenyl" refers to cyclized alkenyl groups. $C_{4-6}$ cycloalkenyl is intended to include $C_4$, $C_5$, and $C_6$ cycloalkenyl groups. Example cycloalkenyl groups include, but are not limited to, cyclobutenyl, cyclopentenyl, and cyclohexenyl.

"Halo" or "halogen" includes fluoro, chloro, bromo, and iodo. "Haloalkyl" is intended to include both branched and straight-chain saturated aliphatic hydrocarbon groups having the specified number of carbon atoms, substituted with 1 or more halogens. Examples of haloalkyl include, but are not limited to, fluoromethyl, difluoromethyl, trifluoromethyl, trichloromethyl, pentafluoroethyl, pentachloroethyl, 2,2,2-trifluoroethyl, heptafluoropropyl, and heptachloropropyl. Examples of haloalkyl also include "fluoroalkyl" that is intended to include both branched and straight-chain saturated aliphatic hydrocarbon groups having the specified number of carbon atoms, substituted with 1 or more fluorine atoms. naphthalenyl "Haloalkoxy" or "haloalkyloxy" represents a haloalkyl group as defined above with the indicated number of carbon atoms attached through an oxygen bridge. For example, "$C_{1-6}$ haloalkoxy", is intended to include $C_1$, $C_2$, $C_3$, $C_4$, $C_5$, and $C_6$ haloalkoxy groups. Examples of haloalkoxy include, but are not limited to, trifluoromethoxy, 2,2,2-trifluoroethoxy, and pentafluorothoxy. Similarly, "haloalkylthio" or "thiohaloalkoxy" represents a haloalkyl group as defined above with the indicated number of carbon atoms attached through a sulphur bridge; for example trifluoromethyl-S—, and pentafluoroethyl-S—.

As used herein, the term "heteroaryl" or "aromatic heterocyclic group" is intended to mean stable monocyclic and polycyclic aromatic hydrocarbons that include at least one heteroatom ring member such as sulfur, oxygen, or nitrogen. Heteroaryl groups include, without limitation, pyridyl, pyrimidinyl, pyrazinyl, pyridazinyl, triazinyl, furyl, quinolyl, isoquinolyl, thienyl, imidazolyl, thiazolyl, indolyl, pyrroyl, oxazolyl, benzofuryl, benzothienyl, benzthiazolyl, isoxazolyl, pyrazolyl, triazolyl, tetrazolyl, indazolyl, 1,2,4-thiadiazolyl, isothiazolyl, purinyl, carbazolyl, benzimidazolyl, indolinyl, benzodioxolanyl, and benzodioxane. Heteroaryl groups are substituted or unsubstituted. The nitrogen atom is substituted or unsubstituted (i.e., N or NR wherein R is H or another substituent, if defined). The nitrogen and sulfur heteroatoms may optionally be oxidized (i.e., N→O and $S(O)_p$, wherein p is 0, 1 or 2).

As used herein, the term "heterocyclo", "heterocyclic" or "heterocyclyl" is intended to mean a 5, 6 or 7 membered non-aromatic ring system containing from 1 to 4 heteroatoms selected from O, N or S. Examples of heterocycles include, but are not limited to, pyrrolidinyl, tetrahydrofuranyl, tetrahydropyranyl, piperidyl, pyrrolinyl, piperazinyl, imidazolinyl, morpholinyl, imidazolidinyl, pyrazolidinyl and pyrazolinyl.

The term "counter ion" is used to represent a negatively charged species such as chloride, bromide, hydroxide, acetate, and sulfate or a positively charged species such as sodium (Na+), potassium (K+), ammonium ($R_nNH_m$+ where n=0-4 and m=0-4) and the like.

The term "electron withdrawing group" (EWG) refers to a substituent which polarizes a bond, drawing electron density towards itself and away from other bonded atoms. Examples of EWG include, but are not limited to, $CF_3$, $CF_2CF_3$, CN, halogen, haloalkyl, $NO_2$, sulfone, sulfoxide, ester, sulfonamide, carboxamide, alkoxy, alkoxyether, alkenyl, alkynyl, OH, C(O)alkyl, $CO_2H$, phenyl, heteroaryl, —O-phenyl, and —O— heteroaryl. Preferred examples of EWG include, but are not limited to, $CF_3$, $CF_2CF_3$, CN, halogen, $SO_2(C_{1-4}$ alkyl), $CONH(C_{1-4}$ alkyl), $CON(C_{1-4}$ alkyl)$_2$, and heteroaryl. More preferred examples of EWG include, but are not limited to, $CF_3$ and CN.

As used herein, the term "amine protecting group" means any group known in the art of organic synthesis for the protection of amine groups which is stable to an ester reducing agent, a disubstituted hydrazine, R4-M and R7-M, a nucleophile, a hydrazine reducing agent, an activator, a strong base, a hindered amine base and a cyclizing agent. Such amine protecting groups fitting these criteria include those listed in Wuts, P. G. M. and Greene, T. W. *Protecting Groups in Organic Synthesis*, 4th Edition, Wiley (2007) and *The Peptides: Analysis, Synthesis, Biology*, Vol. 3, Academic Press, New York (1981), the disclosure of which is hereby incorporated by reference. Examples of amine protecting groups include, but are not limited to, the following: (1) acyl types such as formyl, trifluoroacetyl, phthalyl, and p-toluenesulfonyl; (2) aromatic carbamate types such as benzyloxycarbonyl (Cbz) and substituted benzyloxycarbonyls, 1-(p-biphenyl)-1-methylethoxycarbonyl, and 9-fluorenylmethyloxycarbonyl (Fmoc); (3) aliphatic carbamate types such as tert-butyloxycarbonyl (Boc), ethoxycarbonyl, diisopropylmethoxycarbonyl, and allyloxycarbonyl; (4) cyclic alkyl carbamate types such as cyclopentyloxycarbonyl and adamantyloxycarbonyl; (5) alkyl types such as triphenylmethyl and benzyl; (6) trialkylsilane such as trimethylsilane; (7) thiol containing types such as phenylthiocarbonyl and dithiasuccinoyl; and (8) alkyl types such as triphenylmethyl, methyl, and benzyl; and substituted alkyl types such as 2,2,2-trichloroethyl, 2-phenylethyl, and t-butyl; and trialkylsilane types such as trimethylsilane.

As referred to herein, the term "substituted" means that at least one hydrogen atom is replaced with a non-hydrogen group, provided that normal valencies are maintained and that the substitution results in a stable compound. Ring double bonds, as used herein, are double bonds that are formed between two adjacent ring atoms (e.g., C=C, C=N, or N=N).

In cases wherein there are nitrogen atoms (e.g., amines) on compounds of the present invention, these may be converted to N-oxides by treatment with an oxidizing agent (e.g., mCPBA and/or hydrogen peroxides) to afford other compounds of this invention. Thus, shown and claimed nitrogen atoms are considered to cover both the shown nitrogen and its N-oxide (N→O) derivative.

When any variable occurs more than one time in any constituent or formula for a compound, its definition at each occurrence is independent of its definition at every other occurrence. Thus, for example, if a group is shown to be substituted with 0-3 R, then said group may optionally be substituted with up to three R groups, and at each occurrence R is selected independently from the definition of R. Also, combinations of substituents and/or variables are permissible only if such combinations result in stable compounds.

When a bond to a substituent is shown to cross a bond connecting two atoms in a ring, then such substituent may be bonded to any atom on the ring. When a substituent is listed without indicating the atom in which such substituent is bonded to the rest of the compound of a given formula, then such substituent may be bonded via any atom in such substituent. Combinations of substituents and/or variables are permissible only if such combinations result in stable compounds.

The phrase "pharmaceutically acceptable" is employed herein to refer to those compounds, materials, compositions, and/or dosage forms that are, within the scope of sound medical judgment, suitable for use in contact with the tissues of human beings and animals without excessive toxicity, irritation, allergic response, and/or other problem or complication, commensurate with a reasonable benefit/risk ratio.

As used herein, "pharmaceutically acceptable salts" refer to derivatives of the disclosed compounds wherein the parent compound is modified by making acid or base salts thereof. Examples of pharmaceutically acceptable salts include, but are not limited to, mineral or organic acid salts of basic groups such as amines; and alkali or organic salts of acidic groups such as carboxylic acids. The pharmaceutically acceptable salts include the conventional non-toxic salts or the quaternary ammonium salts of the parent compound formed, for example, from non-toxic inorganic or organic acids. For example, such conventional non-toxic salts include those derived from inorganic acids such as hydrochloric, hydrobromic, sulfuric, sulfamic, phosphoric, and nitric; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, and isethionic, and the like.

The pharmaceutically acceptable salts of the present invention can be synthesized from the parent compound that contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, nonaqueous media like ether, ethyl acetate, ethanol, isopropanol, or acetonitrile are preferred. Lists of suitable salts are found in *Remington: The Science and Practice of Pharmacy*, 22$^{nd}$ Edition, Allen, L. V. Jr., Ed.; Pharmaceutical Press, London, UK (2012), the disclosure of which is hereby incorporated by reference.

In addition, compounds of formula I may have prodrug forms. Any compound that will be converted in vivo to provide the bioactive agent (i.e., a compound of formula I) is a prodrug within the scope and spirit of the invention. Various forms of prodrugs are well known in the art. For examples of such prodrug derivatives, see:

a) *Design of Prodrugs*, Bundgaard, H., ed., Elsevier (1985), and Methods in Enzymology, 112:309-396, Widder, K. et al., eds., Academic Press (1985);

b) Bundgaard, H., Chapter 5, "Design and Application of Prodrugs," *A Textbook of Drug Design and Development*, pp. 113-191, Krosgaard-Larsen, P. et al., eds., Harwood Academic Publishers (1991);

c) Bundgaard, H., *Adv. Drug Deliv. Rev.*, 8:1-38 (1992);

d) Bundgaard, H. et al., *J. Pharm. Sci.*, 77:285 (1988);

e) Kakeya, N. et al., *Chem. Pharm. Bull.*, 32:692 (1984); and f) Rautio, J (Editor). Prodrugs and Targeted Delivery (*Methods and Principles in Medicinal Chemistry*), Vol 47, Wiley-VCH, 2011.

Compounds containing a carboxy group can form physiologically hydrolyzable esters that serve as prodrugs by being hydrolyzed in the body to yield formula I compounds per se. Such prodrugs are preferably administered orally since hydrolysis in many instances occurs principally under the influence of the digestive enzymes. Parenteral administration may be used where the ester per se is active, or in those instances where hydrolysis occurs in the blood. Examples of physiologically hydrolyzable esters of compounds of formula I include $C_{1-6}$alkyl, $C_{1-6}$alkylbenzyl, 4-methoxybenzyl, indanyl, phthalyl, methoxymethyl, $C_{1-6}$ alkanoyloxy-$C_{1-6}$alkyl (e.g., acetoxymethyl, pivaloyloxymethyl or propionyloxymethyl), $C_{1-6}$alkoxycarbonyloxy-$C_{1-6}$alkyl (e.g., methoxycarbonyl-oxymethyl or ethoxycarbonyloxymethyl, glycyloxymethyl, phenylglycyloxymethyl, (5-methyl-2-oxo-1,3-dioxolen-4-yl)-methyl), and other well known physiologically hydrolyzable esters used, for example, in the penicillin and cephalosporin arts. Such esters may be prepared by conventional techniques known in the art.

Preparation of prodrugs is well known in the art and described in, for example, King, F. D., ed., *Medicinal Chemistry: Principles and Practice*, The Royal Society of Chemistry, Cambridge, UK (2$^{nd}$ edition, reproduced, 2006); Testa, B. et al., *Hydrolysis in Drug and Prodrug Metabolism. Chemistry, Biochemistry and Enzymology*, VCHA and Wiley-VCH, Zurich, Switzerland (2003); Wermuth, C. G., ed., *The Practice of Medicinal Chemistry*, 3$^{rd}$ edition, Academic Press, San Diego, Calif. (2008).

The present invention is intended to include all isotopes of atoms occurring in the present compounds. Isotopes include those atoms having the same atomic number but different mass numbers. By way of general example and without limitation, isotopes of hydrogen include deuterium and tritium. Isotopes of carbon include $^{13}C$ and $^{14}C$. Isotopically-labeled compounds of the invention can generally be prepared by conventional techniques known to those skilled in the art or by processes analogous to those described herein, using an appropriate isotopically-labeled reagent in place of the non-labeled reagent otherwise employed.

The term "solvate" means a physical association of a compound of this invention with one or more solvent molecules, whether organic or inorganic. This physical association includes hydrogen bonding. In certain instances the solvate will be capable of isolation, for example when one or more solvent molecules are incorporated in the crystal lattice of the crystalline solid. The solvent molecules in the solvate may be present in a regular arrangement and/or a non-ordered arrangement. The solvate may comprise either a stoichiometric or nonstoichiometric amount of the solvent molecules. "Solvate" encompasses both solution-phase and isolable solvates. Exemplary solvates include, but are not limited to, hydrates, ethanolates, methanolates, and isopropanolates. Methods of solvation are generally known in the art.

As used herein, the term "patient" refers to organisms to be treated by the methods of the present invention. Such organisms preferably include, but are not limited to, mammals (e.g., murines, simians, equines, bovines, porcines, canines, felines, and the like), and most preferably includes humans.

As used herein, the term "therapeutically effective amount" refers to the amount of a compound (e.g., a compound of the present invention) sufficient to effect beneficial or desired results. An effective amount can be administered in one or more administrations, applications or dosages and is not intended to be limited to a particular formulation or administration route. As used herein, the term "treating" includes any effect, e.g., lessening, reducing, modulating, ameliorating or eliminating, that results in the improvement of the condition, disease, disorder, and the like, or ameliorating a symptom thereof.

As used herein, the term "pharmaceutical composition" refers to the combination of an active agent with a carrier, inert or active, making the composition especially suitable for diagnostic or therapeutic use in vivo or ex vivo.

Examples of bases include, but are not limited to, alkali metals (e.g., sodium) hydroxides, alkaline earth metals (e.g., magnesium), hydroxides, ammonia, and compounds of formula $NW_4^+$, wherein W is $C_{1-4}$ alkyl, and the like.

For therapeutic use, salts of the compounds of the present invention are contemplated as being pharmaceutically acceptable. However, salts of acids and bases that are non-pharmaceutically acceptable may also find use, for example, in the preparation or purification of a pharmaceutically acceptable compound.

VI. Methods of Preparation

The macrocyclic compounds 10 can be prepared using the synthetic sequence depicted in Scheme 1. Reaction of a chlorinated resin 2 with commercially available (S)-2-((((9H-fluoren-9-yl)methoxy)carbonyl)amino)-3-(naphthalen-2-yl)propanoic acid (1) in the presence of a base, such as Hunig's base, provides resin-linked compound 3. Conversion of 3 to resin-linked peptide 4 can occur through standard Fmoc solid phase peptide synthesis protocol (i.e., sequential removal of the Fmoc protecting group under basic conditions such as piperidine, followed by amide formation in the presence of a coupling reagent, such as HATU). Azide-alkyne cycloaddition ("click reaction") of the resin-linked peptide 4 (containing an azide) with Fmoc protected alkyne 5 then provides the resin-linked triazole compound 6, which can be converted to the fully elaborated peptide 7 through Fmoc solid phase peptide synthesis protocol. Resin-linked peptide 7 can undergo an azide-alkyne cycloaddition with Fmoc protected alkyne 8. Subsequent removal of the Fmoc group, cleavage from the resin and macrolactamization affords cyclic peptide intermediate 9. Base-promoted hydrolysis and Boc-deprotection of 9 provides the desired analog 10.

SCHEME 1

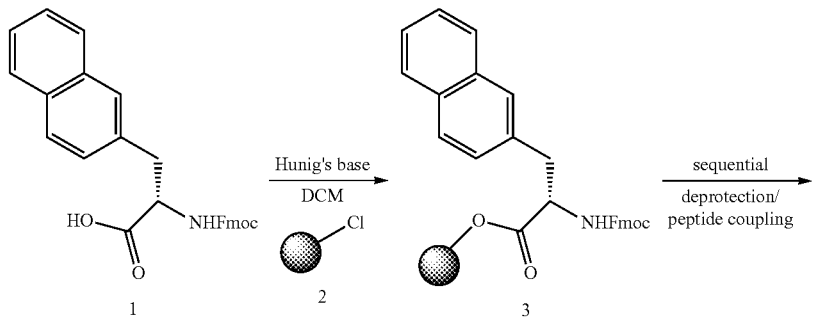

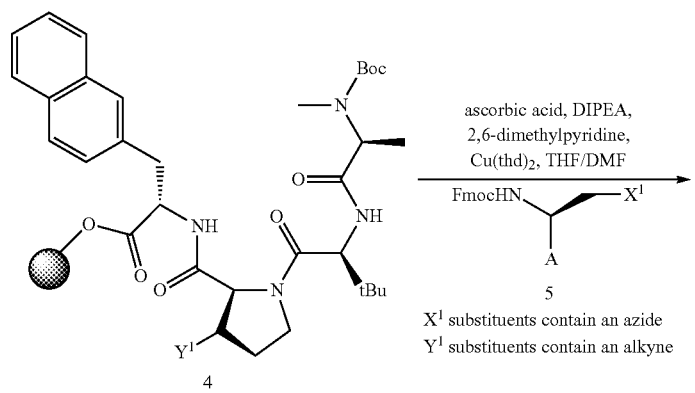

X¹ substituents contain an azide
Y¹ substituents contain an alkyne

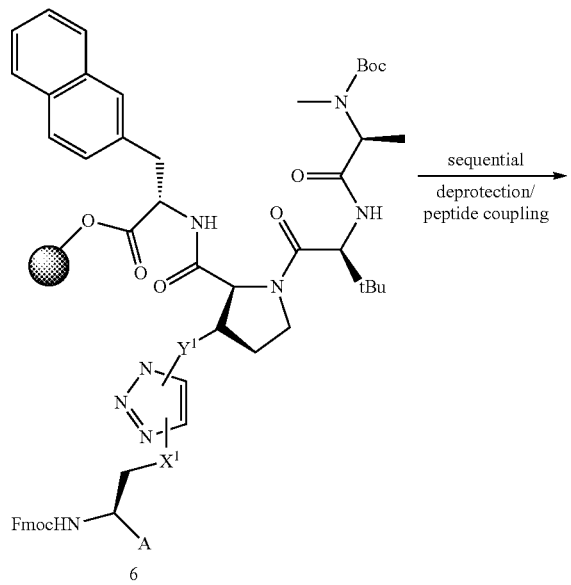

-continued
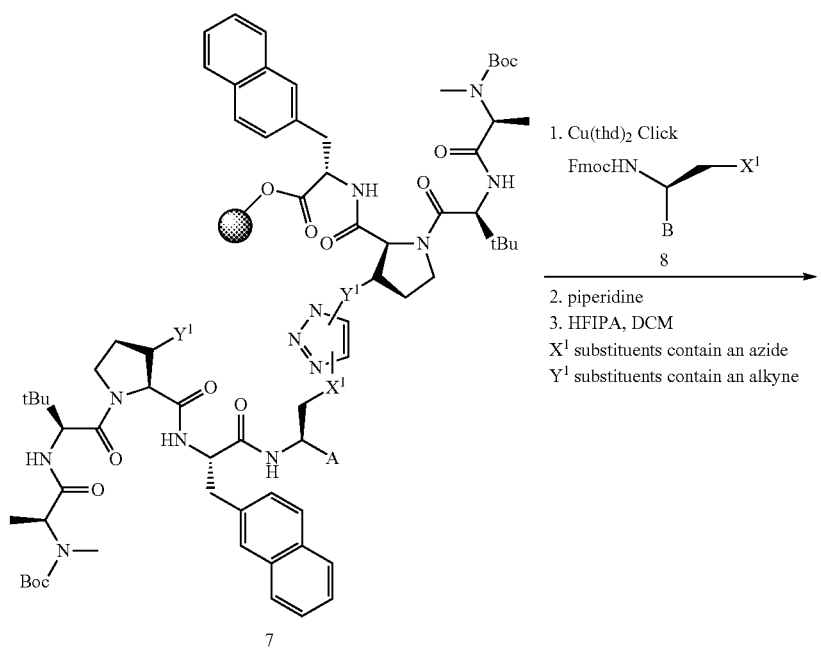
7
1. Cu(thd)$_2$ Click
FmocHN—$\overset{\displaystyle}{\underset{B}{\text{CH}}}$—X$^1$
8
2. piperidine
3. HFIPA, DCM
X$^1$ substituents contain an azide
Y$^1$ substituents contain an alkyne
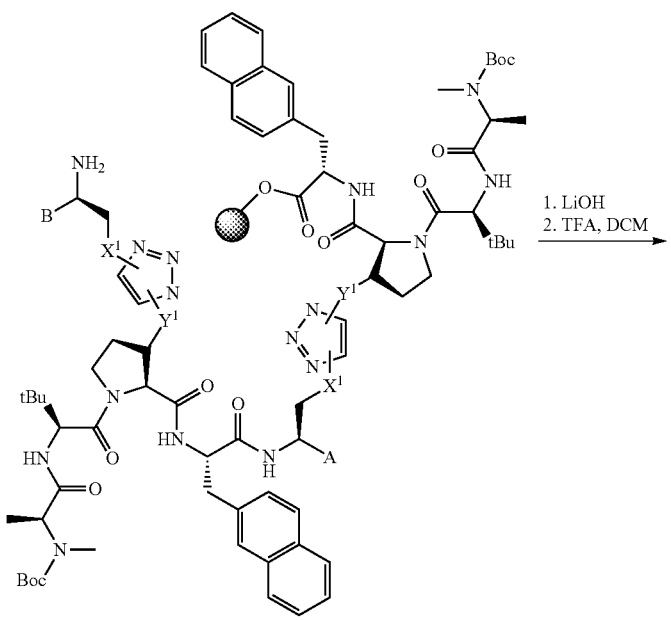
9
1. LiOH
2. TFA, DCM

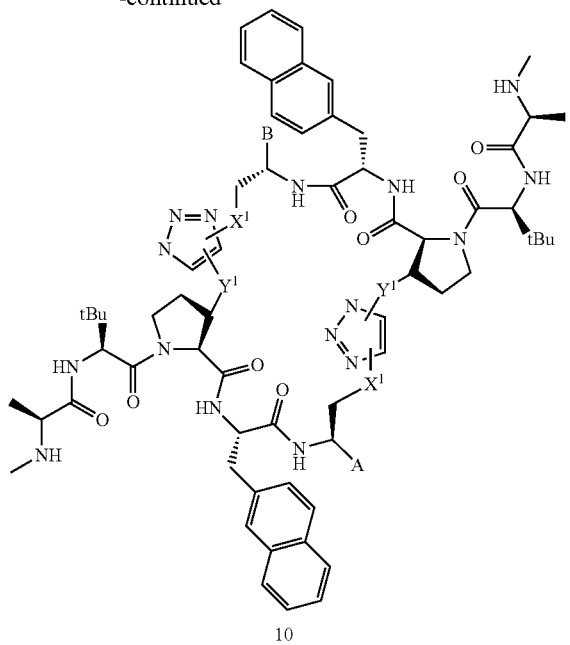

10

The peptide coupling partner 24 can be prepared in solution as shown in Scheme 2. Readily available (2S,3S)-1-(tert-butoxycarbonyl)-3-hydroxypyrrolidine-2-carboxylic acid (11) can be converted to acid 15 in five straightforward steps. Thus, t-butyl ester formation of 11 followed by mesylation of the requisite alcohol affords compound 12. Displacement of the methansulfonyl group of 12 with sodium azide affords intermediate 13, which can be treated with acid to afford azide 14. N-Boc-protection of 14 furnishes 15. Compound 15 can then undergo amide formation with 16 in the presence of, for example, EDC to give dipeptide 17. Removal of the Boc group of 17 and coupling of the requisite amine 18 with commercially available acid 19 (Chem-Impex) gives tripeptide 20. Removal of the Boc protecting group of 20 under acidic conditions and subsequent coupling of the resulting amine 21 with commercially available acid 22 (Chem-Impex) can provide compound 23. Hydrolysis of the methyl ester of 23 then affords the versatile coupling partner 24.

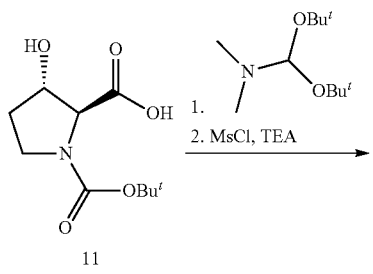

SCHEME 2

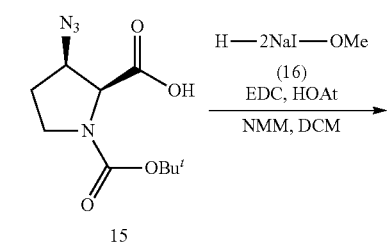

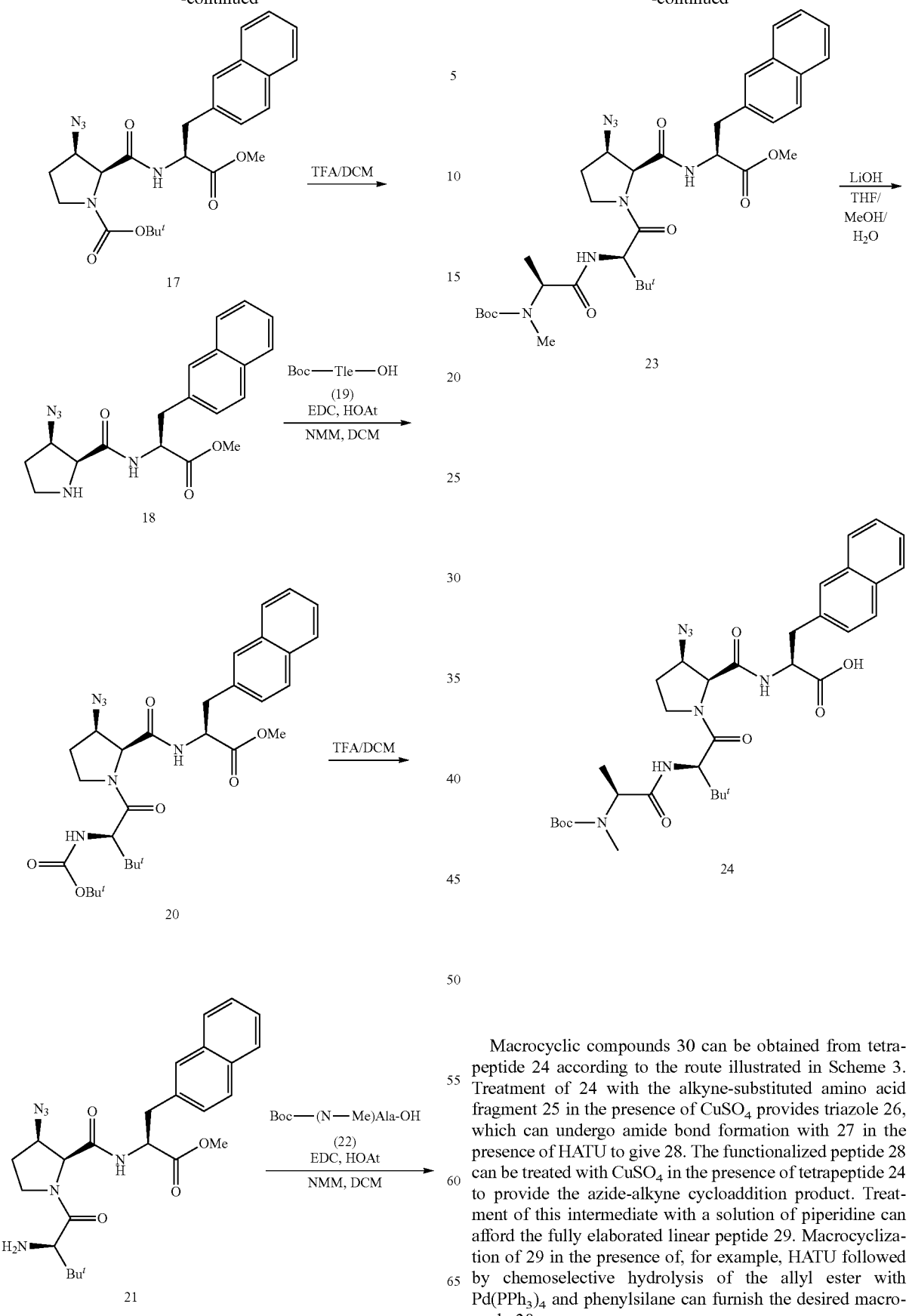

Macrocyclic compounds 30 can be obtained from tetrapeptide 24 according to the route illustrated in Scheme 3. Treatment of 24 with the alkyne-substituted amino acid fragment 25 in the presence of $CuSO_4$ provides triazole 26, which can undergo amide bond formation with 27 in the presence of HATU to give 28. The functionalized peptide 28 can be treated with $CuSO_4$ in the presence of tetrapeptide 24 to provide the azide-alkyne cycloaddition product. Treatment of this intermediate with a solution of piperidine can afford the fully elaborated linear peptide 29. Macrocyclization of 29 in the presence of, for example, HATU followed by chemoselective hydrolysis of the allyl ester with $Pd(PPh_3)_4$ and phenylsilane can furnish the desired macrocycle 30.

SCHEME 3
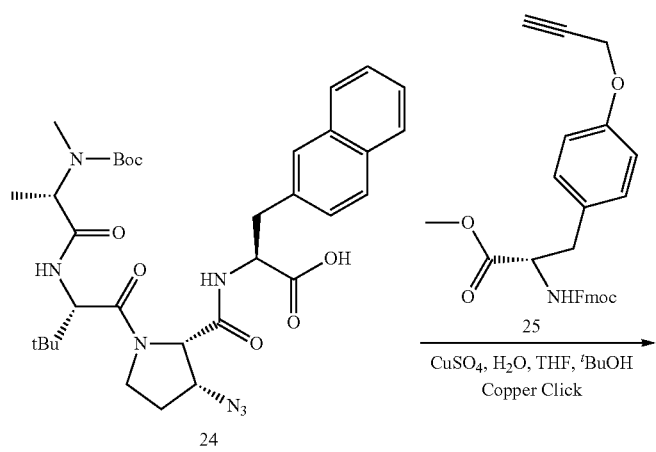
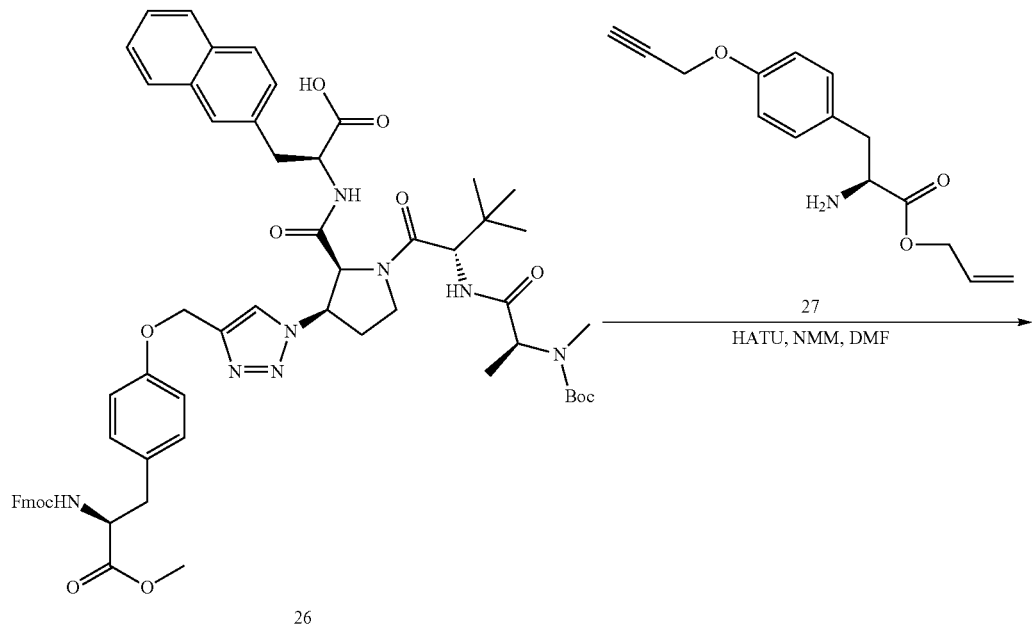

-continued
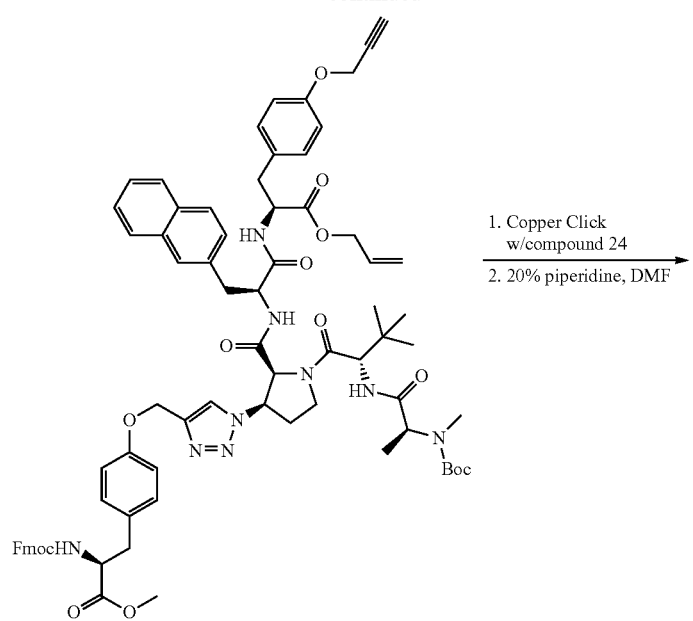
28
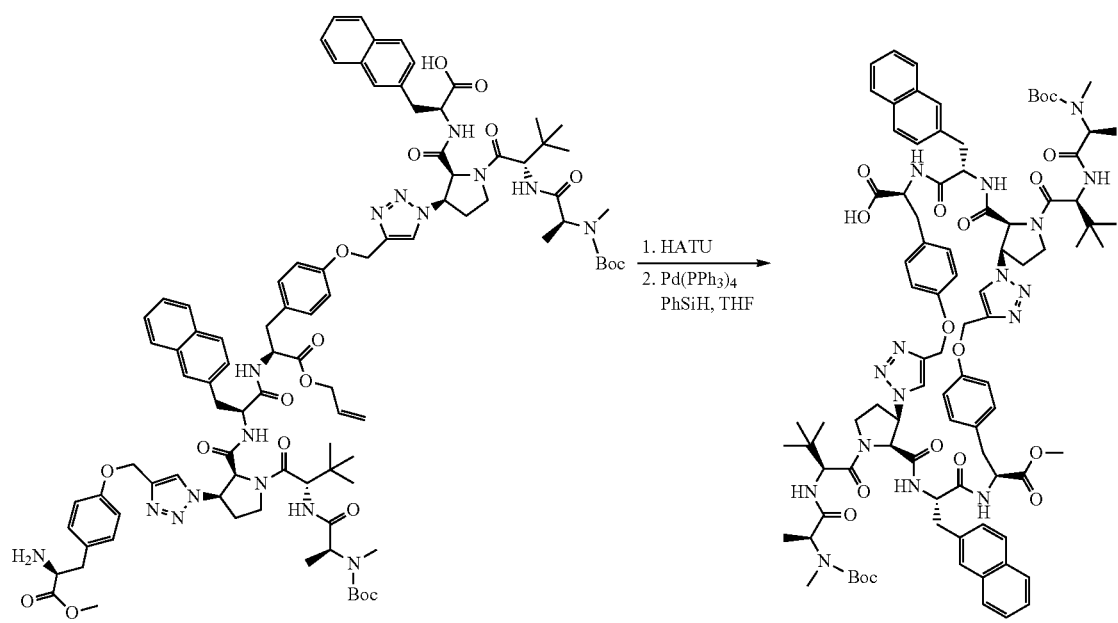
29 30

Macrocyclic bis-carboxylic acid compounds 31 can be prepared from key intermediate 30 via base-promoted hydrolysis with, for example, LiOH and subsequent Boc-deprotection in acidic media (Scheme 4). Alternatively, the mono-acid mono-ester 32 can be obtained by treatment of 30 with TFA.

SCHEME 4

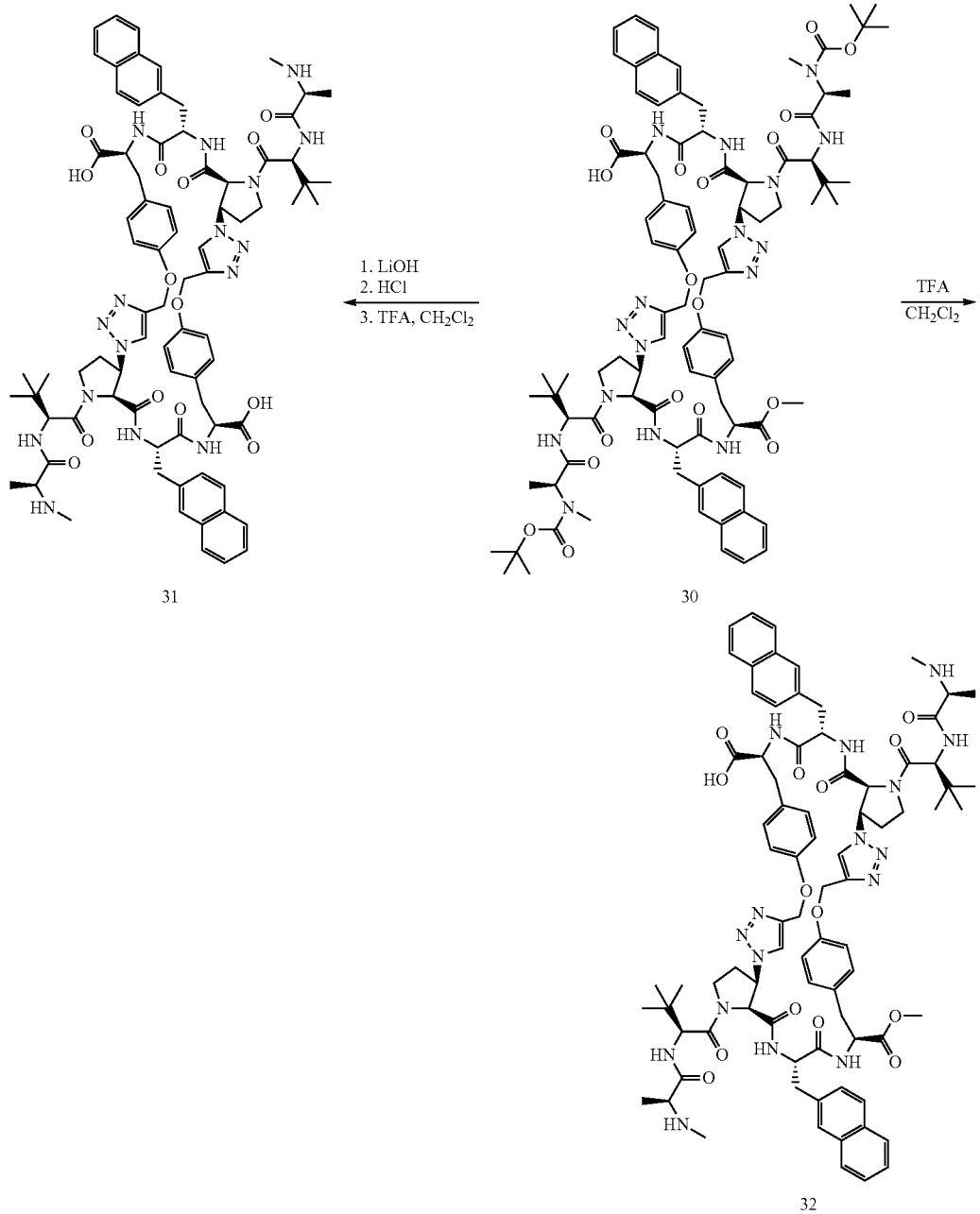

Analogs such as 35 can be prepared according to the synthetic sequence depicted in Scheme 5. Macrocycle 30 can be coupled to various amines, such as (3,5-difluoro-4-methoxyphenyl)methanamine to afford compounds such as 33. The phenol from the anisole fragment of 33 can be unmasked upon treatment with various reagents such as TMS-I. This reagent also facilitates N-Boc-deprotection leading to ester 34 along with the acid 35.

SCHEME 5
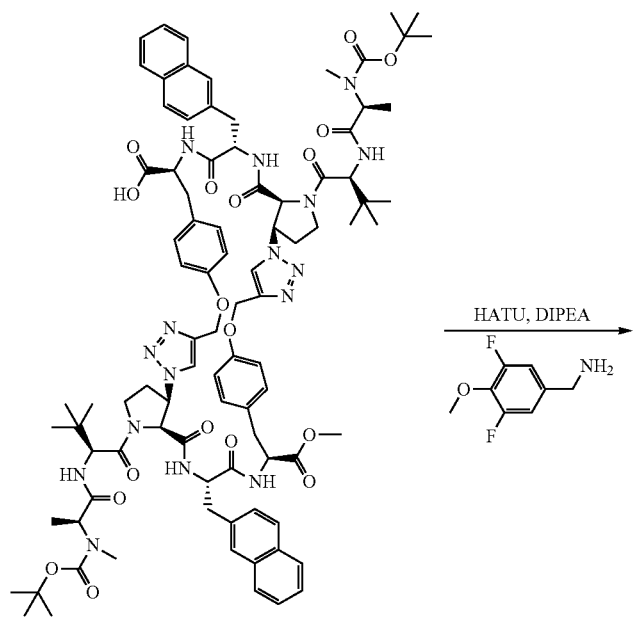
30
HATU, DIPEA
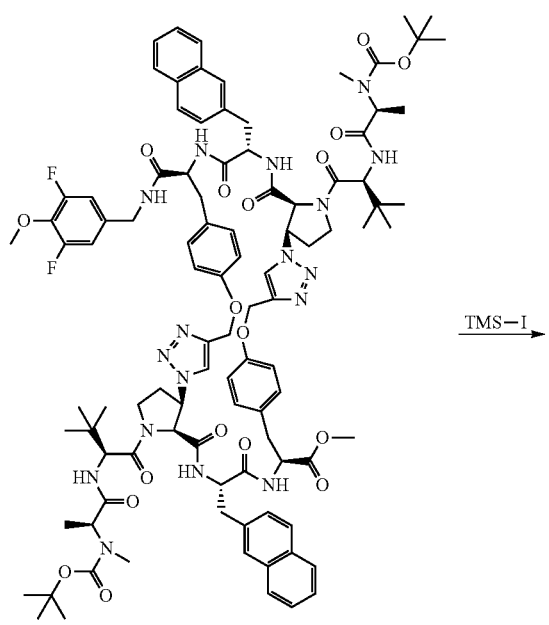
33
TMS—I

-continued

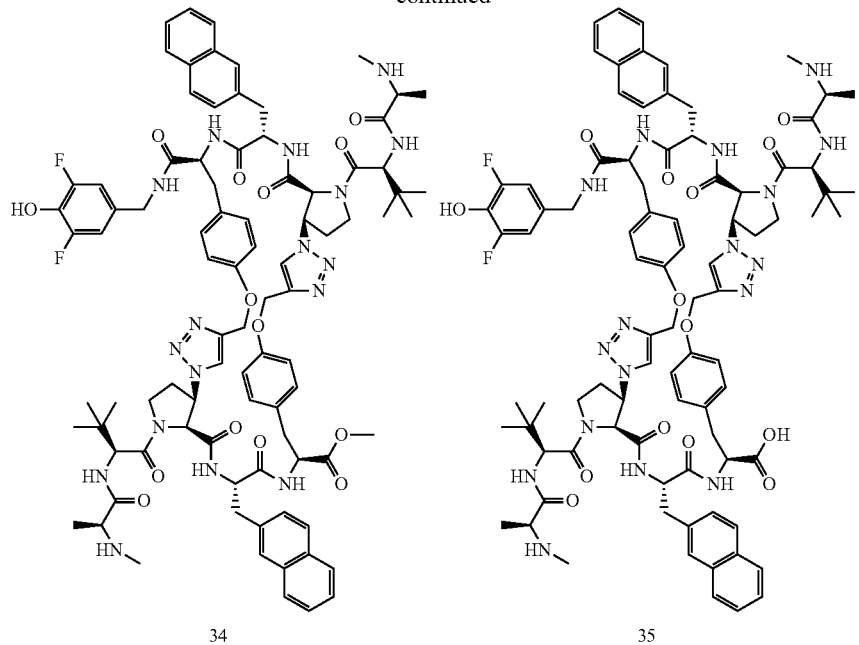

34    35

Analogs such as 39 can be prepared according to the synthetic route illustrated in Scheme 6. Sequential treatment of macrocycle 30 with CDI and an appropriately substituted sulfonamide 36 in the presence of a base, such as DBU, can provide acylsulfonamide derivative 37. Base-promoted hydrolysis of methyl ester 37, followed by removal of the Boc group of the resulting intermediate 38 under acidic condition (e.g. TFA) can provide the desired macrocyclic derivative 39.

-continued

SCHEME 6

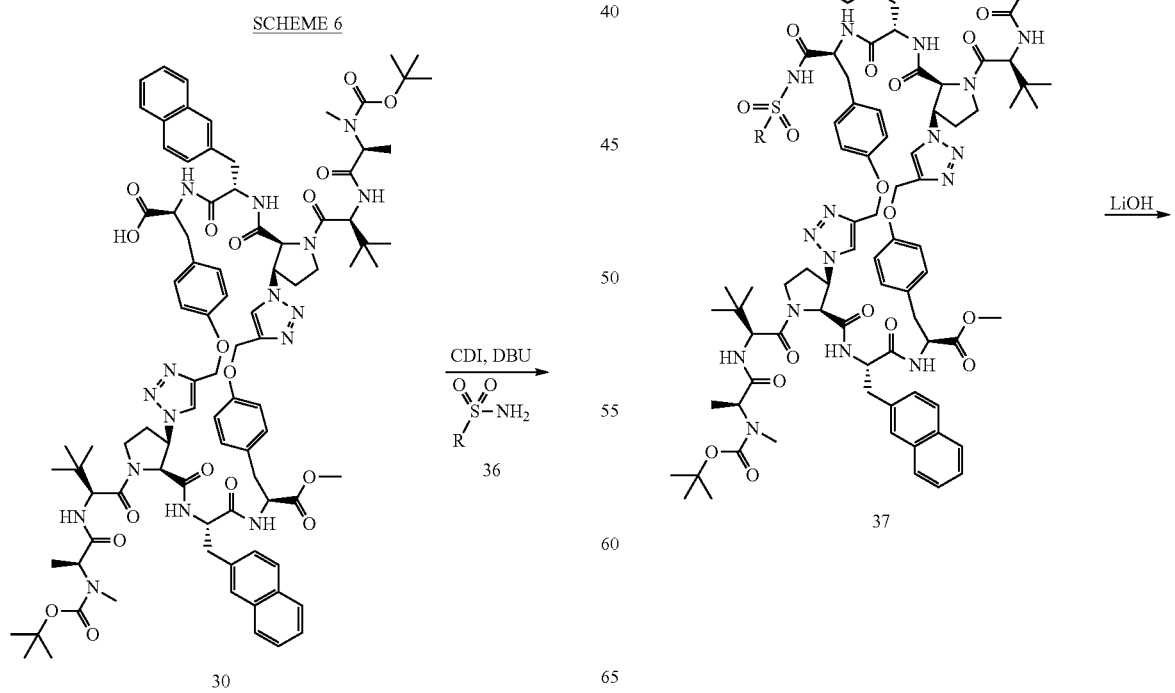

41
-continued

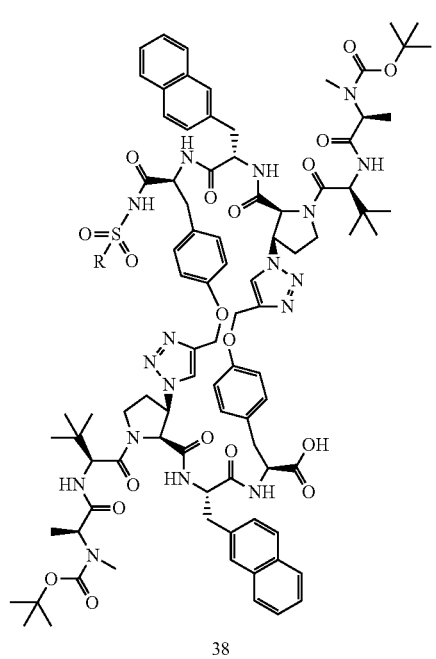

38

42
-continued

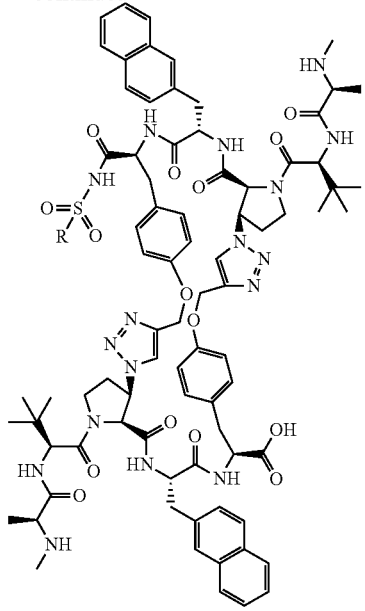

39

Amide analogs such as 42 can be accessed using the synthetic sequence shown in Scheme 7. The coupling of amine 40 with macrocyclic acid 30 can be carried out in the presence of a suitable coupling reagent (e.g., HATU) to afford amide 41. Hydrolysis of the methyl ester of 41 followed by acetonide removal and Boc-deprotection with acid can provide the desired product 42.

SCHEME 7

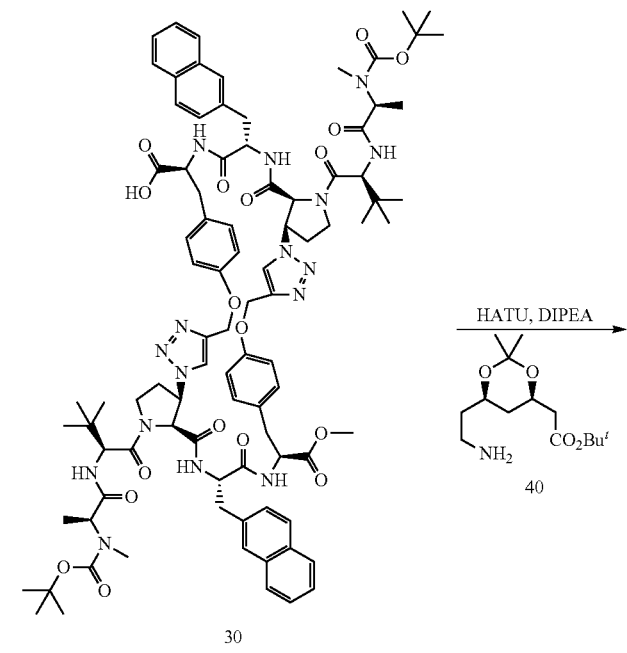

30

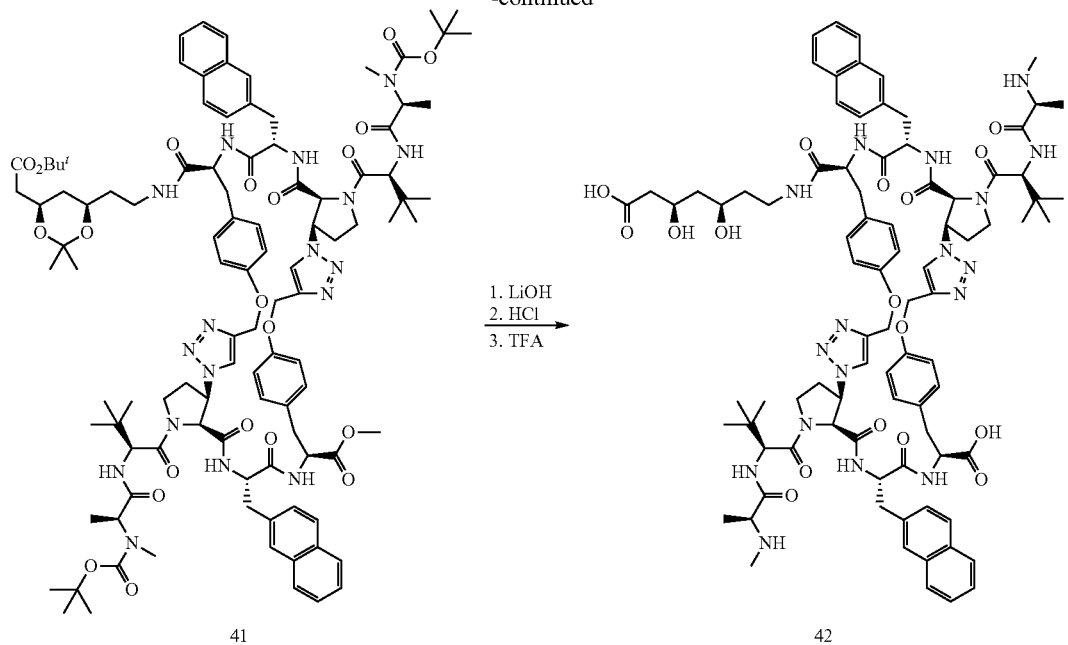

Analogs bearing heterocyclic acid isosteres can be prepared directly from carboxylic acid intermediate 30. As depicted in Scheme 8, macrocycle 30 can be treated with hydrazine to form the corresponding hydrazide 43. Exposure of 43 to CDI (or a related reagent) affects cyclization to generate oxadiazolone 44. Subsequent removal of the N-Boc-protecting group of 44 provides the desired analog 45.

SCHEME 8

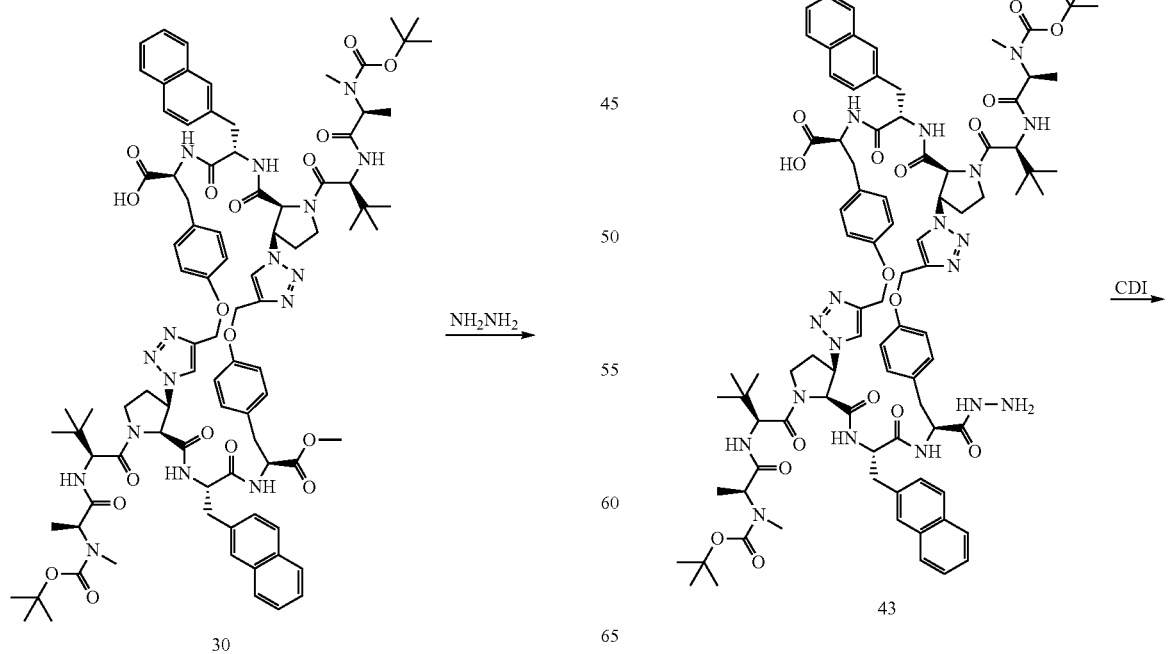

-continued

45

-continued

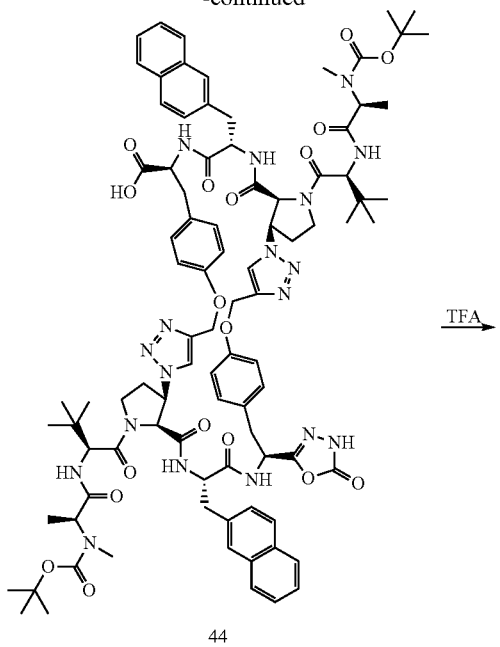

44

TFA →

45

Additional heterocyclic acid isosteres can be prepared from the cyano-substituted macrocycle 46 (Scheme 9). Intermediate 32 can be activated with a suitable chloroformate, such as isobutyl chloroformate. Treatment of the resulting mixed anhydride with ammonia followed by subsequent dehydration using, for example Burgess reagent can furnish the nitrile 46.

46

SCHEME 9

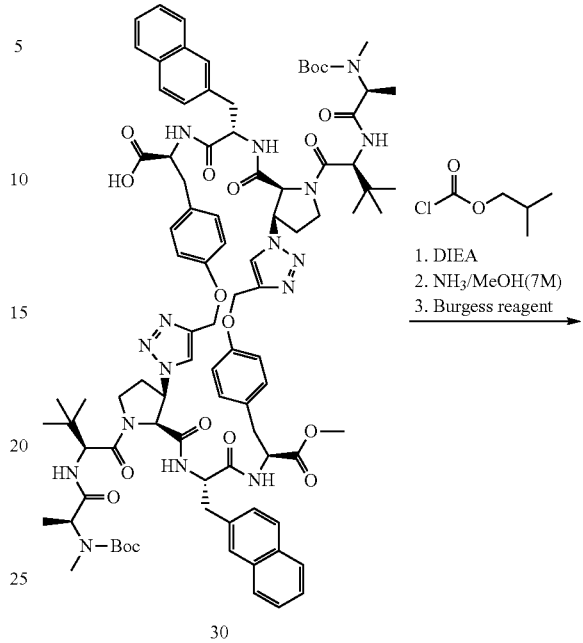

1. DIEA
2. NH₃/MeOH(7M)
3. Burgess reagent
→

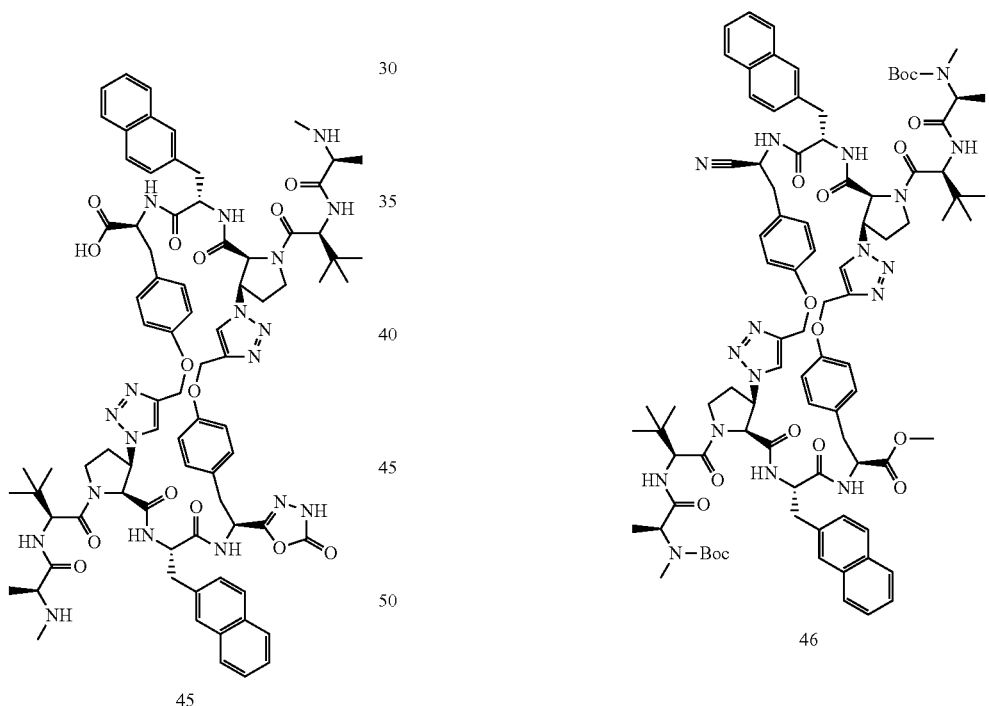

46

Additional heterocyclic analogs, such as the oxadiazolone or oxadiazolethione 48 and tetrazole 49 can be prepared from the cyano-substituted intermediate 46 as outlined in Scheme 10. Hydroxyacetimidamide 47, derived from treatment of 46 with hydroxylamine can be cyclized with CDI or TDI (1,1'-thiocarbonyldiimidazole) to provide the oxadiazolone or oxadiazolethione intermediate, respectively. Base-promoted hydrolysis and N-Boc deprotection can then afford the desired analogs 48. Alternatively, treatment of nitrile 46 with sodium azide and a catalysis, such a Zn(II) bromide provides the tetrazole intermediate. Subsequent ester hydrolysis and Boc-deprotection provides the desired tetrazole analog 49.

SCHEME 10

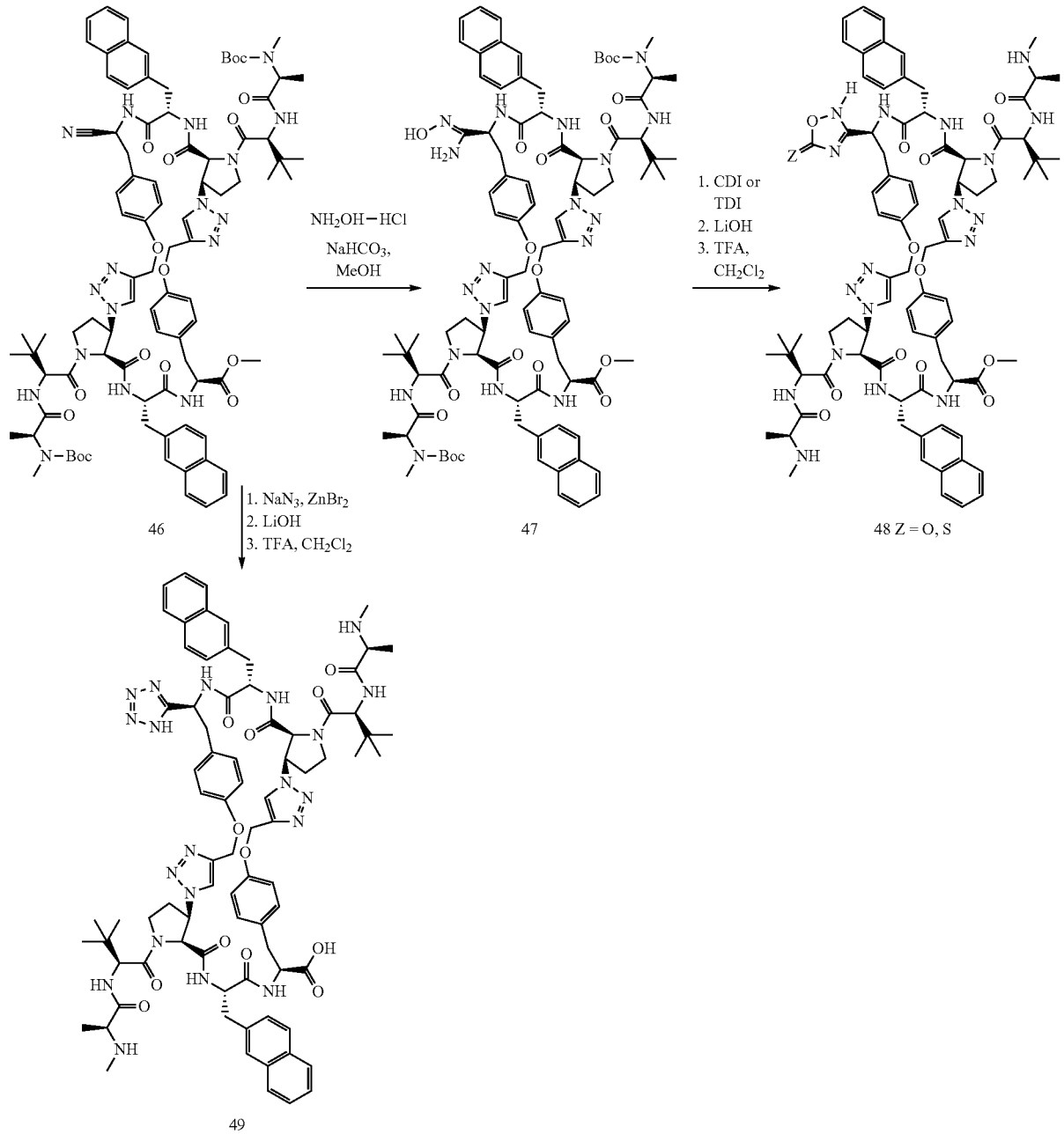

EXAMPLES

General Experimental

All reactions were carried out with continuous magnetic stirring under an atmosphere of dry nitrogen or argon. All evaporations and concentrations were carried out on a rotary evaporator under reduced pressure. Commercial reagents were used as received without additional purification. Solvents were commercial anhydrous grades and were used without further drying or purification. Flash chromatography was performed using prepacked RediSep® $R_f$ silica gel columns on a CombiFlash Companion machine.

Preparative Reverse Phase HPLC was performed with a linear gradient elution using $H_2O$/MeOH or $H_2O$/MeCN mixtures buffered with 0.1% trifluoroacetic acid or 10 mM $NH_4OAc$ and detection at 220 nm on one of the following columns: Shimadzu Sunfire S10 30×250 mm (flow rate=40 mL/min), or C18 Phenenomenex Luna S5 ODS 21×100 mm (flow rate=20 mL/min), or YMC S5 ODS 20×100 mm (flow rate=20 mL/min) or Waters XBridge C18 19×250 mm (flow rate=20 mL/min) Preparative Supercritical Fluid Chromatography (SFC) was performed using 78% $CO_2$/MeOH buffered with 0.1% diethylamine and detection at 220 nm on a Chiralpak AS-H IDS 25×3 cm column (flow rate=85 mL/min).

All final products were characterized by $^1$H NMR, RP HPLC and electrospray ionization (ESI) or atmospheric pressure ionization (API) mass spectrometry (MS). $^1$H NMR spectra were obtained a 500 MHz or a 400 MHz Bruker instrument. Field strengths are expressed in units of δ (parts per million, ppm) relative to the solvent peaks, and peak multiplicities are designated as follows: s, singlet; d, doublet; dd, doublet of doublets; t, triplet; q, quartet; sxt, sextet; br s, broad singlet; m, multiplet.

ABBREVIATIONS

AcOH acetic acid
aq. aqueous
Bn benzyl
Boc t-butyl carbamate
Boc$_2$O di-t-butyl dicarbonate
CDI 1,1'-carbonyldiimidazole
conc. concentrated
DCE dichloroethane
DCM dichloromethane
DIAD diisopropyl azodicarboxylate
DIPEA diisopropylethylamine
DMAP 4-N,N-dimethylaminopyridine
DMF dimethyl formamide
DMSO dimethyl sulfoxide
EDC 1-(dimethylaminopropyl)-3-ethylcarbodiimide hydrochloride
Et ethyl
EtOAc ethyl acetate
EtOH ethanol
Et$_2$O diethyl ether
Et$_3$N triethyl amine
h hour(s)
HATU O-(7-azabenzotriazol-1-yl)-N,N,N',N'-tetramethyluronium hexafluorophosphate
HOAt 1-hydroxy-7-azabenzotriazole
HPLC high pressure liquid chromatography
i-PrOH isopropanol
min minute(s)
Me methyl
MeCN acetonitrile
MeOH methanol
NMM N-methylmorpholine
NMR nuclear magnetic resonance
Pd/C palladium on carbon
Pd(dppf)$_2$Cl$_2$ [1,1'-bis(diphenylphosphino)ferrocene]dichloropalladium(II)
Pd(OAc)$_2$ palladium acetate
Pd(PPh$_3$)$_4$ tetrakis(triphenylphosphine)palladium
Pd$_2$(dba)$_3$ tris(dibenzylideneacetone)dipalladium(0)
Ph phenyl
PhMe toluene
PhNTf$_2$ N-phenyl-bis(trifluoromethanesulfonimide)
PPh$_3$ triphenyl phosphorus
sat. saturated
t-Bu tertiary butyl
t-BuOH tertiary butanol
TDI 1,1'-thiocarbonyldiimidazole
TFA trifluoroacetic acid
THF tetrahydrofuran
TMS trimethylsilyl Example 1

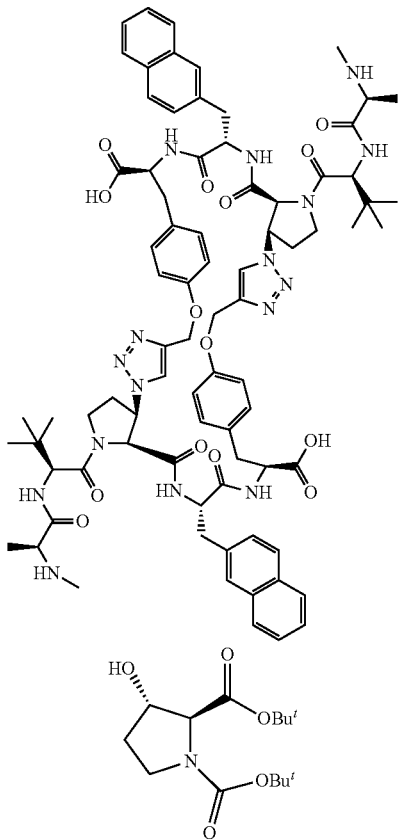

A) (2S,3S)-Di-tert-butyl 3-hydroxypyrrolidine-1,2-dicarboxylate 1,1-Di-tert-butoxy-N,N-dimethylmethanamine (25 mL, 122 mmol) and freshly prepared (2S,3S)-1-(tert-butoxycarbonyl)-3-hydroxypyrrolidine-2-carboxylic acid (28.3 g, 122 mmol, see *Eur. J. Org. Chem.* 2009, 3368-3386) were heated to 80° C. overnight. The next day, the reaction mixture was cooled to rt, treated with H$_2$O (30 mL), and stirred at rt for 3 h. The mixture was then extracted with EtOAc and washed with aq. LiCl soln. (3×). The combined organic layers were dried over Na$_2$SO$_4$, filtered, and concentrated to a give an oil. The crude material was purified by flash column chromatography (ELSD ISCO, Silica gel, 330 g column, hexanes to EtOAc) to afford the desired product (7.7 g) as a white solid (7.7 g). MS (ESI$^+$) rt 0.94 min, m/z 288.2.

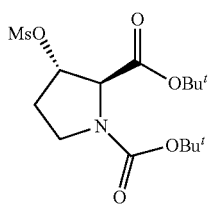

B) (2S,3S)-Di-tert-butyl 3-((methylsulfonyl)oxy) pyrrolidine-1,2-dicarboxylate To a solution of (2S,3S)-di-tert-butyl 3-hydroxypyrrolidine-1,2-dicarboxylate (7.7 g, 27 mmol) in CH$_2$Cl$_2$ (48.7 mL) was added triethylamine (5.98 mL, 42.9 mmol) and the resulting solution was cooled to 0° C. With internal temperature monitoring so not to exceed 3.5° C., methanesulfonyl chloride (2.297 ml, 29.5 mmol) was added and the resulting solution was permitted to stir at 0° C. until complete consumption of starting material was observed. The reaction mixture was quenched with the addition of H$_2$O, extracted with CH$_2$Cl$_2$ (2×), washed with 1N HCl, sat. aq. NaHCO$_3$ soln., and brine. The combined organics were dried over MgSO$_4$, filtered and concentrated in vacuo to give the desired product (9.79 g) as a brown oil, which was used directly in the next step without purification. MS (ESI$^+$) rt 0.99 min, m/z 210.1 (-Boc, -tBu).

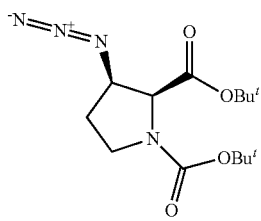

C) (2S,3R)-Di-tert-butyl 3-azidopyrrolidine-1,2-dicarboxylate

Sodium azide (2.61 g, 40.2 mmol) was added to a solution of (2S,3S)-di-tert-butyl 3-((methylsulfonyl)-oxy)pyrrolidine-1,2-dicarboxylate (9.79 g, 26.8 mmol) in DMF (40 mL). The reaction mixture was heated to 70° C. overnight and treated with an additional 0.5 g of sodium azide. The mixture was heated to 80° C., stirred for another 12 h and cooled to rt. The mixture was poured into H$_2$O (50 mL), extracted with EtOAc (200 mL), and washed with 10% aq. LiCl soln, (3×50 mL). The combined organic extracts were dried over MgSO$_4$, filtered and concentrated to a light brown oil (8.57 g). The crude material was purified by flash column chromatography (ISCO, 120 g of Silica gel, hexanes to EtOAc) to afford the desired product (5.8 g, 69%) as a clear colorless oil. MS (ESI$^+$) rt 1.10 min, m/z 158.0 (-Boc, -tBu).

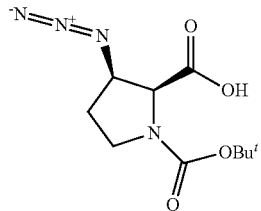

D) (2S,3R)-3-Azido-1-(tert-butoxycarbonyl)pyrrolidine-2-carboxylic acid

A solution of (2S,3R)-di-tert-butyl 3-azidopyrrolidine-1, 2-dicarboxylate (5.8 g, 18.57 mmol), CH$_2$Cl$_2$ (60 mL), and TFA (30 mL) was stirred at rt until LCMS confirmed the reaction was complete. The solvent was removed in vacuo to yield a brown oil, which was used directly in the next step-MS (ESI$^+$) rt 0.57 min, m/z 157.2. The intermediate was dissolved in THF (43 mL) and 1M aq. NaOH (42.7 mL, 42.7 mmol), and treated with di-tert-butyl dicarbonate (4.05 g, 18.6 mmol) at rt. Upon complete conversion of the starting material, the pH of the solution was adjusted to 4 with concentrated HCl. The mixture was extracted with EtOAc (4×100 mL) and the organics were dried over MgSO$_4$, filtered and concentrated to a brown oil (7.13 g). The crude material was purified by flash column chromatography (ISCO, 120 g of Silica gel, hexanes to EtOAc) to yield the desired product (1.54 g) as an off-white solid. MS (ESI$^+$) rt 0.72 min, m/z 157.2 (-Boc).

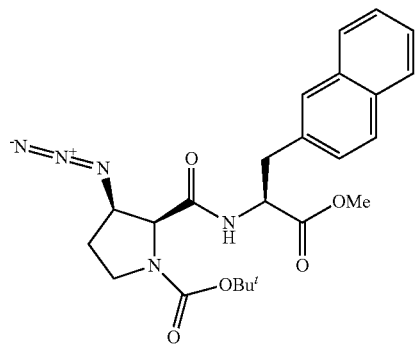

E) (2S,3R)-tert-Butyl 3-azido-2-(((S)-1-methoxy-3-(naphthalen-2-yl)-1-oxo-propan-2-yl)carbamoyl) pyrrolidine-1-carboxylate To a solution of (2S,3R)-3-azido-1-(tert-butoxycarbonyl) pyrrolidine-2-carboxylic acid (1.54 g, 6.01 mmol), EDC (1.32 g, 6.87 mmol) and 3H-[1,2,3]-triazolo[4,5-b]pyridin-3-ol (HOAt, 0.935 g, 6.87 mmol) in CH$_2$Cl$_2$ (57.2 mL) at 0° C. was added a pre-mixed solution of N-methylmorpholine (1.89 mL, 17.2 mmol) and (S)-methyl 2-amino-3-(naphthalen-2-yl)propanoate (1.31 g, 5.72 mmol). The resulting mixture was stirred and warmed to rt. The reaction was monitored by LCMS until complete conversion of starting material was observed, at which point the reaction was quenched and washed with sat. aq NaHCO$_3$ soln. The mixture was extracted with CH$_2$Cl$_2$ and washed with 1N HCl. The combined organics were dried over MgSO$_4$, filtered and concentrated in vacuo to produce an oil. The crude material was purified by flash column chromatography (ISCO, 40 g of Silica gel, hexanes to EtOAc) to afford the desired product (2.67 g) as a white foam. MS (ESI$^+$) rt 1.08 min, m/z 468.3.

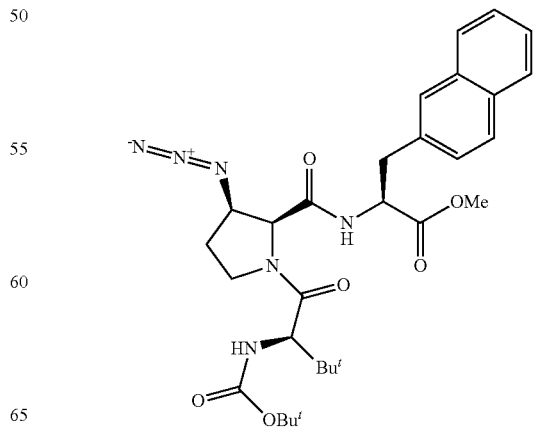

F) (S)-Methyl 2-((2S,3R)-3-azido-1-((S)-2-((tert-butoxycarbonyl)amino)-3,3-dimethylbutanoyl)pyrrolidine-2-carboxamido)-3-(naphthalen-2-yl)propanoate To a solution of (2S,3R)-tert-butyl 3-azido-2-(((S)-1-methoxy-3-(naphthalen-2-yl)-1-oxopropan-2-yl)carbamoyl)pyrrolidine-1-carboxylate (2.67 g, 5.71 mmol) in $CH_2Cl_2$ (10 mL) was added 4N HCl in dioxane (15 mL). The reaction mixture was stirred at rt until Boc removal was complete. The solvent was then removed in vacuo to afford (S)-methyl 2-((2S,3R)-3-azidopyrrolidine-2-carboxamido)-3-(naphthalen-2-yl)propanoate as a foam, which was used directly in the next step without purification. MS (ESI+) rt 0.85 min, m/z 368.3.

To a solution of the intermediate (S)-methyl 2-((2S,3R)-3-azidopyrrolidine-2-carboxamido)-3-(naphthalen-2-yl)propanoate (2.10 g, 5.71 mmol) and N-methylmorpholine (1.88 ml, 17.1 mmol) in $CH_2Cl_2$ (10 mL) at 0° C. was added 3H-[1,2,3]-triazolo[4,5-b]pyridin-3-ol (0.933 g, 6.85 mmol), (S)-2-((tert-butoxycarbonyl)amino)-3,3-dimethylbutanoic acid (1.32 g, 5.71 mmol) and EDC (1.314 g, 6.85 mmol). The resulting reaction mixture was slowly warmed to rt. Upon complete conversion of the starting materials, the mixture was quenched and washed with sat. aq. $NaHCO_3$ soln. The mixture was extracted with $CH_2Cl_2$ and washed with 1N HCl. The combined organics were dried over $MgSO_4$, filtered and concentrated in vacuo to produce an oil. The crude material was purified by flash column chromatography (ISCO, 40 g of Silica gel, hexanes to EtOAc) to afford the desired product (2.93 g, 88%) as a white foam. MS (ESI+) rt 1.16 min, m/z 581.6

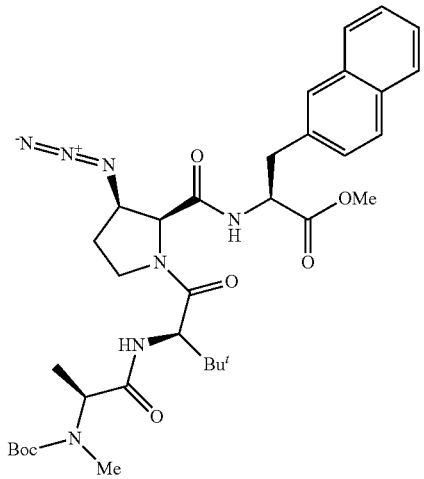

G) (S)-Methyl 2-((2S,3R)-3-azido-1-((S)-2-((S)-2-((tert-butoxycarbonyl)-(methyl)amino)propanamido)-3,3-dimethylbutanoyl)pyrrolidine-2-carboxamido)-3-(naphthalen-2-yl)propanoate To (S)-methyl 2-((2S,3R)-3-azido-1-((S)-2-((tert-butoxycarbonyl)amino)-3,3-dimethylbutanoyl)pyrrolidine-2-carboxamido)-3-(naphthalen-2-yl)propanoate (2.93 g, 5.05 mmol) in $CH_2Cl_2$ (10 mL) was added 4N HCl in dioxane (15 mL). The resulting solution was stirred at rt until complete removal of the Boc group was affected, at which time the solvent was removed to furnish (S)-methyl 2-((2S,3R)-1-((S)-2-amino-3,3-dimethylbutanoyl)-3-azidopyrrolidine-2-carboxamido)-3-(naphthalen-2-yl)propanoate as a foam. This material was used directly in the next step without further purification.

To a solution of the above intermediate (S)-methyl 2-((2S,3R)-1-((S)-2-amino-3,3-dimethylbutanoyl)-3-azidopyrrolidine-2-carboxamido)-3-(naphthalen-2-yl)propanoate and N-methylmorpholine (1.66 ml, 15.1 mmol) in $CH_2Cl_2$ (10 mL) at 0° C. was added 3H-[1,2,3]-triazolo[4,5-b]pyridin-3-ol (0.824 g, 6.06 mmol), (S)-2-((tert-butoxycarbonyl)-(methyl)amino)propanoic acid (1.03 g, 5.05 mmol) and EDC (1.16 g, 6.06 mmol). The resulting reaction mixture was stirred while slowly warming to rt and monitored by LCMS until conversion to the desired material was observed. The solution was quenched with sat. aq. $NaHCO_3$ soln. and extracted with $CH_2Cl_2$. The organics were washed with 1N HCl and the combined extracts were dried over $MgSO_4$, filtered and concentrated in vacuo to produce an oil. The crude material was purified by flash column chromatography (ISCO, 40 g of Silica gel, hexanes to EtOAc) to afford the desired product (2.84 g, 85%) as a white foam. MS (ESI+) rt 1.10 min, m/z 667.4.

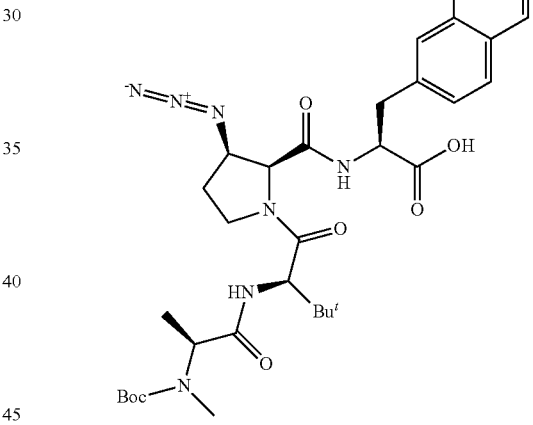

H) (S)-2-((2S,3R)-3-Azido-1-((S)-2-((S)-2-((tert-butoxycarbonyl)(methyl)-amino)propanamido)-3,3-dimethylbutanoyl)pyrrolidine-2-carboxamido)-3-(naphthalen-2-yl)propanoic acid (S)-Methyl 2-((2S,3R)-3-azido-1-((S)-2-((S)-2-((tert-butoxycarbonyl)(methyl)-amino)propanamido)-3,3-dimethylbutanoyl)pyrrolidine-2-carboxamido)-3-(naphthalen-2-yl)propanoate (2.84 g, 4.27 mmol) was dissolved in THF (10.66 mL)/MeOH (10.66 mL) and the resulting solution was treated with 2M LiOH (5.33 mL, 10.66 mmol) at rt until complete conversion of the starting material was observed (MS (ESI+) rt 1.01 min, m/z 652.4). The reaction mixture was acidified to pH 3 with 1N HCl and extracted with EtOAc (3×). The combined organic extracts were dried over $MgSO_4$, filtered, and concentrated in vacuo to afford the desired product (2.63 g, 95%), which was used directly in the next step without purification. MS (ESI) rt 1.01 min, m/z 652.4.

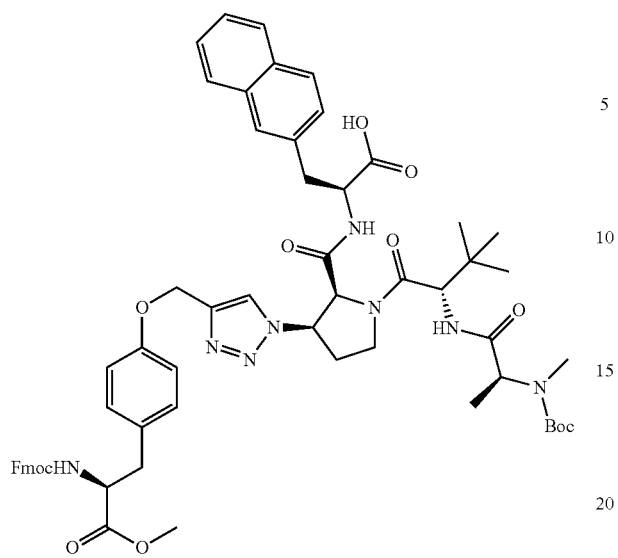
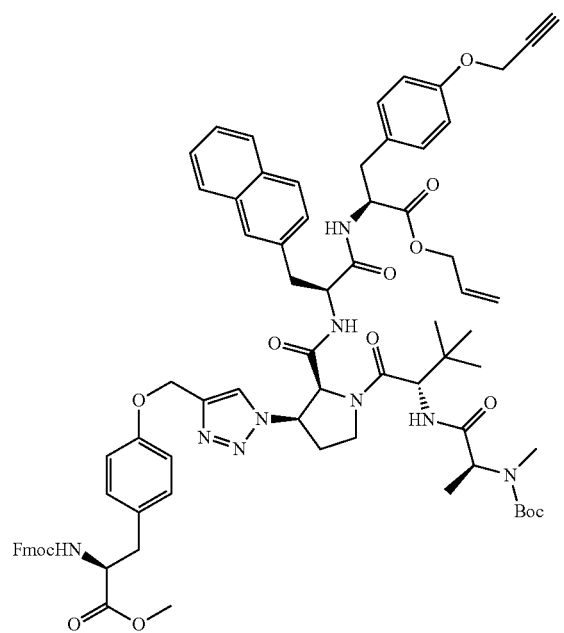

I) (S)-2-((2S,3R)-3-(4-((4-((S)-2-((((9H-Fluoren-9-yl)methoxy)carbonyl)amino)-3-methoxy-3-oxopropyl)phenoxy)methyl)-1H-1,2,3-triazol-1-yl)-1-((S)-2-((S)-2-((tert-butoxycarbonyl)(methyl)amino)propanamido)-3,3-dimethylbutanoyl)-pyrrolidine-2-carboxamido)-3-(naphthalen-2-yl)propanoic acid A round bottom flask was charged with (S)-2-((2S,3R)-3-azido-1-((S)-2-((S)-2-((tert-butoxycarbonyl)-(methyl)amino)-propanamido)-3,3-dimethylbutanoyl)pyrrolidine-2-carboxamido)-3-(naphthalen-2-yl)propanoic acid (1.32 g, 2.03 mmol), (S)-methyl 2-((((9H-fluoren-9-yl)methoxy)carbonyl)amino)-3-(4-(prop-2-yn-1-yloxy)phenyl)propanoate (0.969 g, 2.13 mmol), t-BuOH (25 mL), and THF (25 mL). The mixture was treated with $H_2O$ (12.5 mL) containing copper (II) sulfate pentahydrate (0.025 g, 0.101 mmol) and sodium ascorbate (0.109 g, 0.506 mmol). The solution became yellow instantly and was stirred at rt for 2 h. The mixture was poured into 1 N HCl (5 mL) and EtOAc (30 mL), and extracted EtOAc (3×35 mL). The combined organics were dried over $MgSO_4$, filtered and concentrated in vacuo. The crude solid was purified by reverse phase ISCO (C18 43 g column, 50-95% $MeCN/H_2O$ to MeCN with 0.1% TFA). The desired fractions containing the product were combined over $NaHCO_3$ and extracted with EtOAc (4×). The combined organic extracts were dried over $MgSO_4$, filtered and concentrated in vacuo to afford the desired product (0.89 g, 40%) as a tan solid. MS (ESI) rt 1.16 min, m/z 652.4.

J) (S)-Allyl 2-((S)-2-((2S,3R)-3-(4-((4-((S)-2-(((((9H-fluoren-9-yl)methoxy)-carbonyl)amino)-3-methoxy-3-oxopropyl)phenoxy)methyl)-1H-1,2,3-triazol-1-yl)-1-((S)-2-((S)-2-((tert-butoxycarbonyl)(methyl)amino)propanamido)-3,3-dimethyl-butanoyl)pyrrolidine-2-carboxamido)-3-(naphthalen-2-yl)propanamido)-3-(4-(prop-2-yn-1-yloxy)phenyl)propanoate To a solution of (S)-2-((2S,3R)-3-(4-((4-((S)-2-((((9H-fluoren-9-yl)methoxy)carbonyl)-amino)-3-methoxy-3-oxopropyl)phenoxy)methyl)-1H-1,2,3-triazol-1-yl)-1-((S)-2-((S)-2-((tert-butoxycarbonyl)(methyl)amino)propanamido)-3,3-dimethyl-butanoyl)pyrrolidine-2-carboxamido)-3-(naphthalen-2-yl)propanoic acid (0.89 g, 0.80 mmol) in DMF (20 mL) was added (S)-allyl 2-amino-3-(4-(prop-2-yn-1-yloxy)phenyl)propanoate, HCl (0.285 g, 0.965 mmol), N-methylmorpholine (0.353 mL, 3.22 mmol) and HATU (0.336 g, 0.884 mmol). After 1 h, the reaction mixture was poured into EtOAc (100 mL) and washed with 10% aq. LiCl soln. (50 mL). The aqueous layer was extracted with EtOAC (3×50 mL). The combined organic extracts were washed with 1N HCl (50 mL), sat. aq. $NaHCO_3$ soln. (50 mL), dried over $MgSO_4$, filtered and concentrated in vacuo to afford the desired product (1.21 g) as an oil.

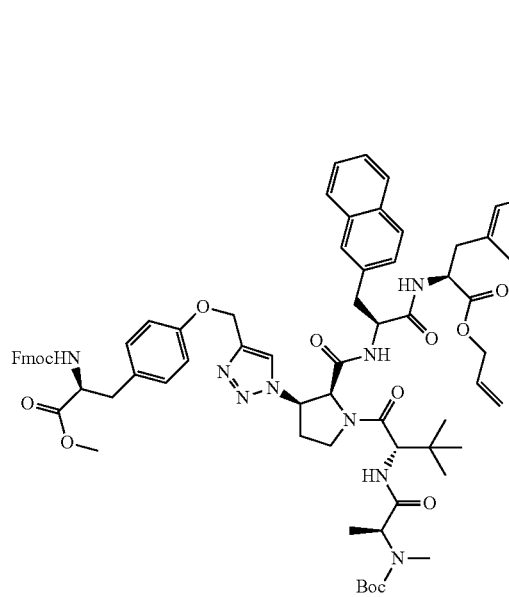
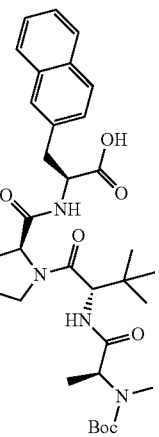

K) (S)-2-((2S,3R)-3-(4-((4-((S)-2-((S)-2-((2S,3R)-3-(4-((4-((S)-2-((((9H-Fluoren-9-yl)methoxy)carbonyl)amino)-3-methoxy-3-oxopropyl)phenoxy)methyl)-1H-1,2,3-triazol-1-yl)-1-((S)-2-((S)-2-((tert-butoxycarbonyl)(methyl)amino)propanamido)-3,3-dimethylbutanoyl)pyrrolidine-2-carboxamido)-3-(naphthalen-2-yl)propanamido)-3-(allyloxy)-3-oxopropyl)phenoxy)methyl)-1H-1,2,3-triazol-1-yl)-1-((S)-2-((S)-2-((tert-butoxycarbonyl)(methyl)amino)propanamido)-3,3-dimethylbutanoyl)pyrrolidine-2-carboxamido)-3-(naphthalen-2-yl)propanoic acid A round bottom flask charged with (S)-2-((2S,3R)-3-azido-1-((S)-2-((S)-2-((tert-butoxycarbonyl)(methyl)amino)propanamido)-3,3-dimethylbutanoyl)pyrrolidine- 2-carboxamido)-3-(naphthalen-2-yl)propanoic acid (0.524 g, 0.804 mmol), (S)-2-((2S,3R)-3-azido-1-((S)-2-((S)-2-((tert-butoxycarbonyl)(methyl)amino)propanamido)-3,3-dimethylbutanoyl)pyrrolidine-2-carboxamido)-3-(naphthalen-2-yl)propanoic acid (0.524 g, 0.804 mmol), t-BuOH (25 ml) and THF (25 mL). To the mixture was added H$_2$O (12.5 mL), copper (II) sulfate pentahydrate (10.0 mg, 0.040 mmol) and sodium ascorbate (0.043 g, 0.201 mmol). The resulting reaction mixture was stirred at rt overnight (MS (ESI$^+$) rt 1.28 min, m/z 1001.8 (M+2)). The solution was diluted with 1N HCl (15 mL). The layers were separated and the organics were washed with brine (100 mL) and the aqueous layer was further extracted with EtOAc (2×100 mL). The combined organics were dried over MgSO$_4$, filtered and concentrated in vacuo. The crude oil was purified by reverse phase ISCO (50-95% MeCN in H$_2$O containing 0.1% TFA) to afford the desired product (900 mg, 56%) as a foam. MS (ESI$^+$) rt 1.28 min, m/z 1001.4 (M+2).

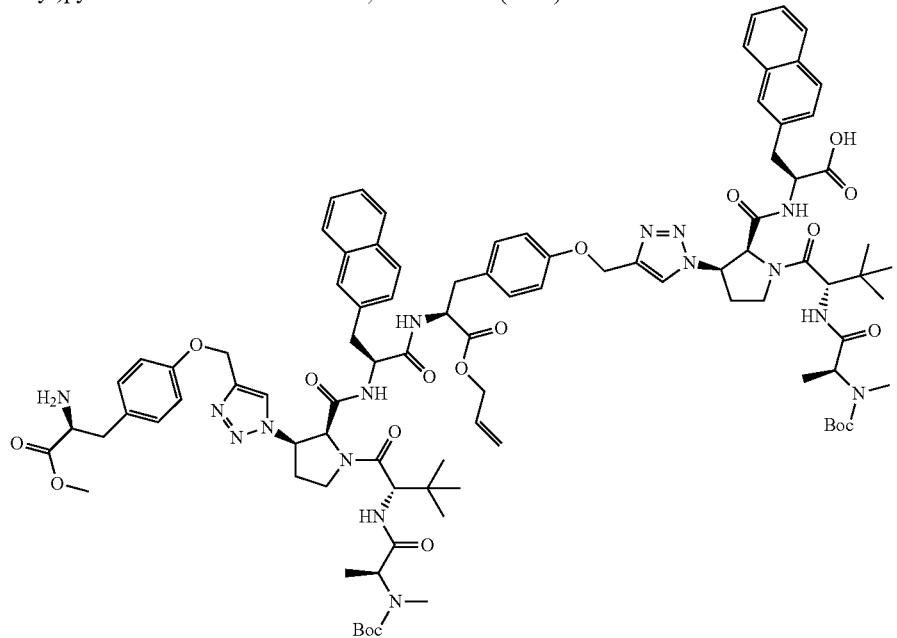 [SMILES: C=CCOC(=O)[C@H](Cc1ccc(OCc2cn([C@@H]3CCN(C(=O)[C@@H](NC(=O)[C@H](C)N(C)C(=O)OC(C)(C)C)C(C)(C)C)[C@@H]3C(=O)N[C@@H](Cc3ccc4ccccc4c3)C(=O)O)nn2)cc1)NC(=O)[C@H](Cc1ccc2ccccc2c1)NC(=O)[C@@H]1[C@H](n2cc(COc3ccc(C[C@H](N)C(=O)OC)cc3)nn2)CCN1C(=O)[C@@H](NC(=O)[C@H](C)N(C)C(=O)OC(C)(C)C)C(C)(C)C]

L) (S)-2-((2S,3R)-3-(4-((4-((S)-3-(Allyloxy)-2-((S)-2-((2S,3R)-3-(4-((4-((S)-2-amino-3-methoxy-3-oxopropyl)phenoxy)methyl)-1H-1,2,3-triazol-1-yl)-1-((S)-2-((S)-2-((tert-butoxycarbonyl)(methyl)amino)propanamido)-3,3-dimethylbutanoyl)-pyrrolidine-2-carboxamido)-3-(naphthalen-2-yl)propanamido)-3-oxopropyl)-phenoxy)methyl)-1H-1,2,3-triazol-1-yl)-1-((S)-2-((S)-2-((tert-butoxycarbonyl)-(methyl)amino)propanamido)-3,3-dimethylbutanoyl)pyrrolidine-2-carboxamido)-3-(naphthalen-2-yl)propanoic acid Piperidine (0.178 mL, 1.80 mmol) was added to a solution of (S)-2-((2S,3R)-3-(4-((4-((S)-2-((S)-2-((2S,3R)-3-(4-((4-((S)-2-((((9H-fluoren-9-yl)methoxy)carbonyl)-amino)-3-methoxy-3-oxopropyl)phenoxy)methyl)-1H-1,2,3-triazol-1-yl)-1-((S)-2-((S)-2-((tert-butoxycarbonyl)(methyl)amino)propanamido)-3,3-dimethylbutanoyl)pyrrolidine-2-carboxamido)-3-(naphthalen-2-yl)propanamido)-3-(allyloxy)-3-oxopropyl)phenoxy)-methyl)-1H-1,2,3-triazol-1-yl)-1-((S)-2-((S)-2-((tert-butoxycarbonyl)(methyl)amino)-propanamido)-3,3-dimethylbutanoyl)pyrrolidine-2-carboxamido)-3-(naphthalen-2-yl)-propanoic acid (900 mg, 0.450 mmol) in DMF (5 mL) at rt. The resulting solution was stirred for 30 min until complete conversion of the starting material was affected—MS (ESI⁺) rt 1.09 min, m/z 1779.1. The reaction solution was purified directly by reverse phase ISCO (gold 40 g column, 40-95% MeCN in H$_2$O containing 0.1% TFA) to afford the desired product (850 mg) as a tan wax.

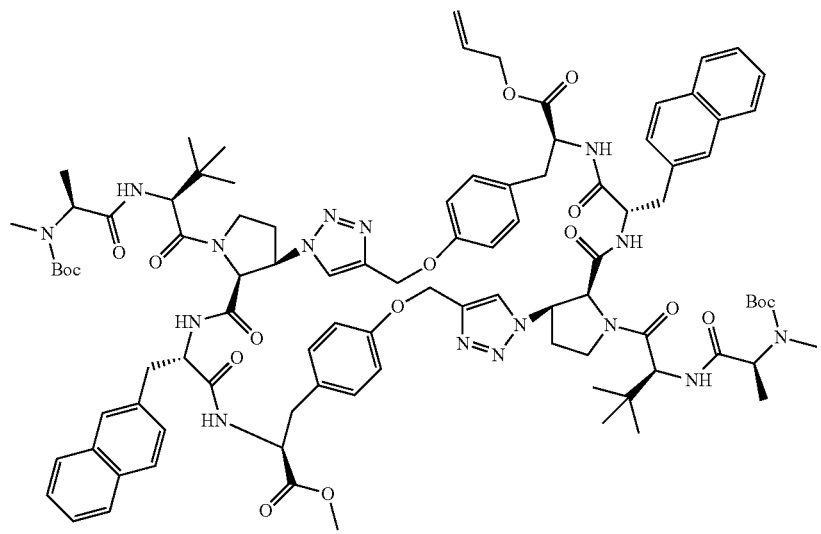

M) Compound M

A solution of 2-(3H-[1,2,3]triazolo[4,5-b]pyridin-3-yl)-1,1,3,3-tetramethylisouronium hexafluorophosphate(V) (545 mg, 1.434 mmol), N-ethyl-N-isopropylpropan-2-amine (0.250 mL, 1.43 mmol) in DMF (54.3 mL) was added to Compound L (850 mg, 0.478 mmol) in CH$_2$Cl$_2$ (543 mL) at rt. Upon complete conversion of the starting material (MS (ESI⁺) rt 1.21 min, m/z 881.0 (M+2)), the reaction mixture was quenched with 1N HCl (20 mL), washed with 10% aq. LiCl (100 mL) and extracted with CH$_2$Cl$_2$ (2×). The combined organics were dried over MgSO$_4$, filtered and concentrated in vacuo. The crude residue was taken up in DMF (5 mL) and purified by reverse phase ISCO (C18 100 g gold column, 40-95% MeCN in H$_2$O containing 0.1% TFA) to obtain the desired product (710 mg, 84%) as a white foam. MS (ESI⁺) rt 1.22 min, m/z 1761.0 (M+1), 880.6 (M+2). HPLC Purity: Low pH Column-1: Sunfire C18 3.5 um, 3.0×150 mm; 92.6% at 220 rt=15.56 min; Low pH Column-2: Xbridge Phenyl 3.5 um, 3.0×150 mm; 87% at 220 rt=13.779 min.

N) Compound N

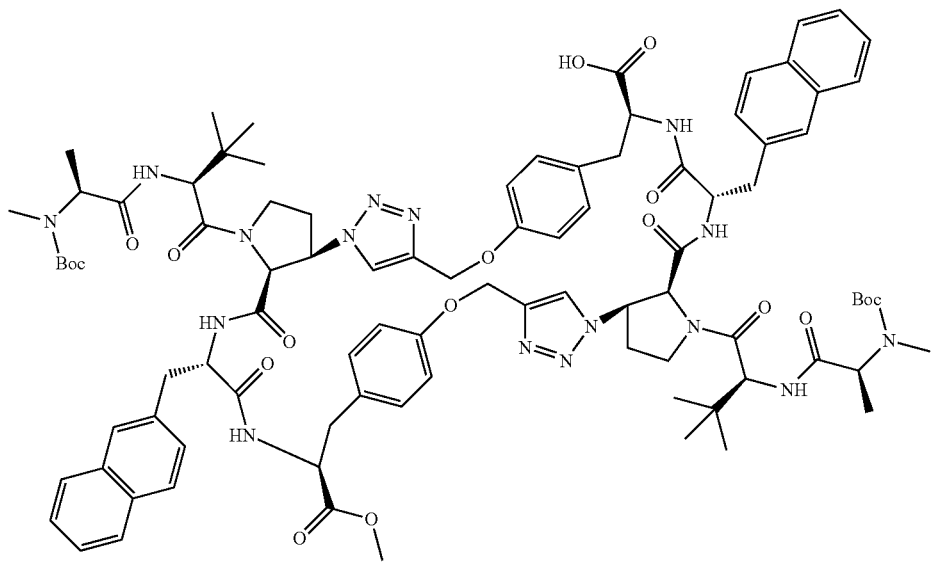

A solution of Compound M (688 mg, 0.391 mmol) in anhydrous THF (20 mL) was placed under $N_2$, cooled to 0° C., and treated with phenylsilane (0.289 mL, 2.345 mmol) and tetrakis(triphenylphosphine)palladium(0) (22.59 mg, 0.020 mmol). The reaction mixture was warmed to rt and stirred for 2 h (MS (ESI+) rt 1.16 min, m/z 1720.1). The crude material was poured into EtOAc (150 mL), washed with brine, and extracted with EtOAc (2×50 mL). The combined organics were dried over $MgSO_4$, filtered and concentrated in vacuo. The residue was purified by reverse phase ISCO (C18 100 g gold column, 30-95% MeCN in $H_2O$ containing 0.1% TFA) to afford the desired product (671 mg). MS (ESI+) rt 1.16 min, m/z 1720.0 (M+1), 860.9 (M+2). HPLC Purity: Low pH, Column-1: Sunfire C18 3.5 um, 3.0×150 mm; 93.3% at 220 rt=14.161 min; Low pH Column-2: Xbridge Phenyl 3.5 um, 3.0×150 mm; 91.4% at 220 rt=12.924 min.

O) Example 1

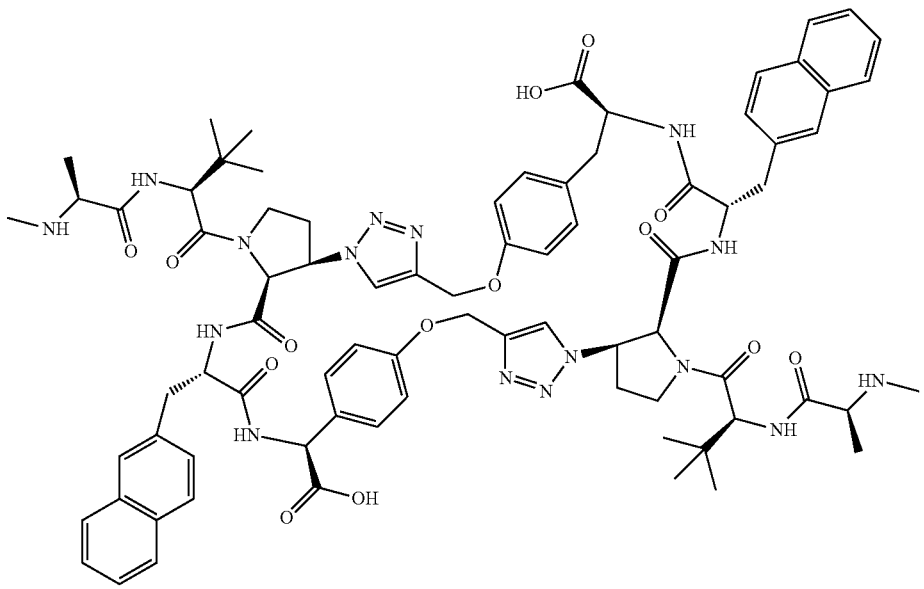

To Compound N (112 mg, 0.065 mmol) in THF (3 mL) was added 2M LiOH (0.108 mL, 0.216 mmol) and the solution was stirred at rt for 1.5 h. The reaction mixture was acidified with 1N HCl (0.4 mL) and concentrated in vacuo. The crude solid was dissolved in $CH_2Cl_2$ (5 mL) and TFA (5 mL) at rt and stirred until the consumption of starting material was achieved. The mixture was concentrated in vacuo and the residue crude was purified by reverse phase preparative HPLC (C18 30×250 mm) The desired fractions containing the product were combined and then lyophilized in the presence of 1N HCl to afford Example 1 (50 mg, 48%). MS (ESI+) rt 0.70 min, m/z 753.8 (M+2). HPLC Purity: Phenomenex Luna 5u C18(2) 150×4.6, 10-100% B, 20 min gradient, 1 mL/min flow rate (rt 13.722 min, 98.5%); mobile A (0.1% TFA H₂O), mobile B (0.1% TFA MeCN).

Example 2

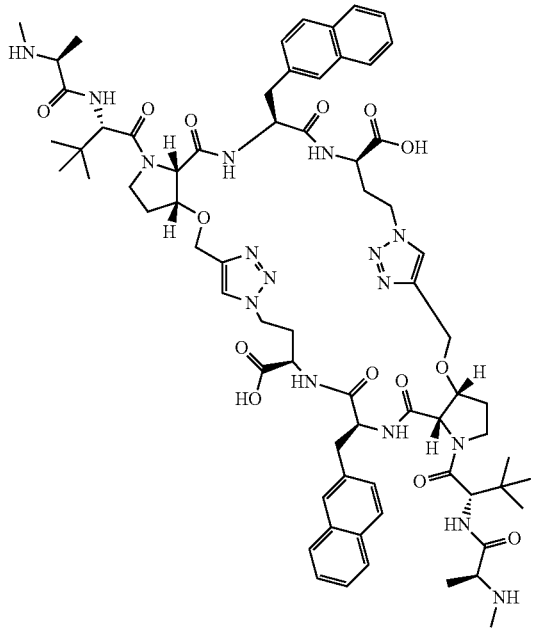

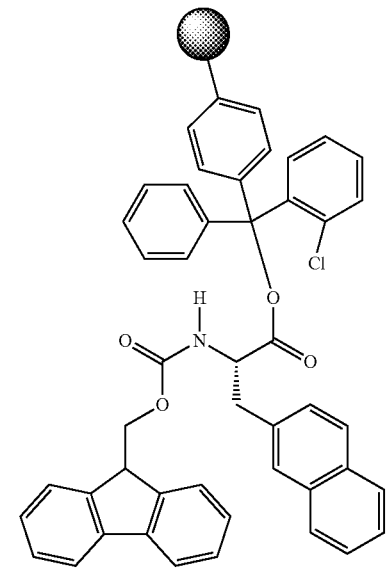

A) Step A

A solution of (S)-2-((((9H-fluoren-9-yl)methoxy)carbonyl)amino)-3-(naphthalen-2-yl)propanoic acid, (Chem-Impex Int'l Inc, 0.715 mmol, 0.313 g) and DIPEA (Aldrich, 7.15 mmol, 1.25 mL) in CH₂Cl₂ (15 mL) was added to 2-chlorotrityl resin (Chem-Impex Int'l Inc, 1.43 mmol/g, 4.51 mmol, 0.5 g) in a glass peptide synthesis vesicle. The resin was rocked for 16 h, and the reaction mixture was filtered. To the resin was added a solution of MeOH (1 mL), DIPEA (2 mL) in CH₂Cl₂ (17 mL) and the mixture was rocked for an additional 0.5 h. The solvent was removed by filtration, and the solid resin was washed with DMF (2×10 mL) and then CH₂Cl₂ (3×10 mL). The resulting resin was dried overnight to give the desired product. Loading was assessed by FMOC determination, 0.527 g/mmol

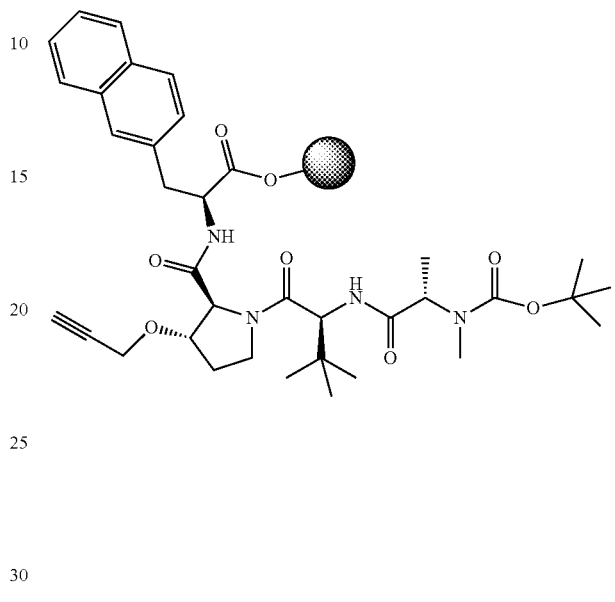

B) Step B

On a Symphony Peptide Synthesizer (Protein Technology Inc. Tucson, Ariz.), resin in Step A (0.100 mmol) was swelled with DMF (7 mL×4 min) and mixed with a gentle stream of N₂ every 30 seconds. The solvent was drained and the following method was used to couple the first amino acid: the Fmoc group was removed from the resin-supported building block by washing the resin twice with a solution of 20% piperidine in DMF (5 mL and 2.5 minutes per wash) and mixing with a gentle stream of N₂ every 30 seconds. The resin was washed three times with DMF (5 mL and 1.5 min per wash). (2S,3S)-1-(((9H-fluoren-9-yl)methoxy)carbonyl)-3-(prop-2-yn-1-yloxy)pyrrolidine-2-carboxylic acid (0.2 M solution in DMF, 0.5 mmol, 1 h) was then added, followed by HATU (Chem-Impex Intl, 0.4M solution in DMF, 1.25 mL, 0.5 mmol) and N-methyl morpholine (Aldrich, 0.8 M in DMF, 1.25 mL, 1 mmol). The reaction mixture was agitated by a gentle stream of nitrogen for 1 h. The reagents were drained from the reaction vessel, and the resin was washed three times with DMF (5 mL×1.5 min).

The resulting resin-supported Fmoc-protected dipeptide was then sequentially deprotected and coupled with (S)-2-((((9H-fluoren-9-yl)methoxy)carbonyl)amino)-3,3-dimethylbutanoic acid (Chem-Impex Int'l Inc, 0.5 mmol, 3 h) and then (S)-2-((tert-butoxycarbonyl)(methyl)amino) propanoic acid (Chem-Impex Int'l Inc, 0.5 mmol, 1 h) to give the desired resin-supported product.

LCMS analysis was performed on peptide aliquot, which was cleaved from the resin (analytical amount of the resin was treated with HFIPA (20% solution hexaflouroisopropanol in CH₂Cl₂, 0.5 mL) at rt for 2 h and then filtered through a syringe filter to give a solution of the free peptide). MS(ESI⁺) m/z 665.3 (M+H).

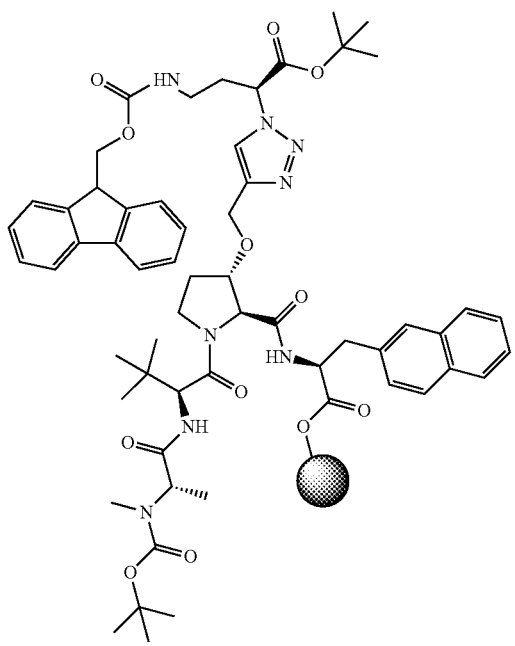 [SMILES: COC(=O)[C@H](Cc1ccc2ccccc2c1)NC(=O)[C@@H]1[C@@H](OCc2cn([C@@H](CCNC(=O)OCC3c4ccccc4-c4ccccc43)C(=O)OC(C)(C)C)nn2)CCN1C(=O)[C@@H](NC(=O)[C@H](C)N(C)C(=O)OC(C)(C)C)C(C)(C)C]

C) Step C

A freshly made solution of copper(II) (Z)-2,2,6,6-tetramethyl-5-oxohept-3-en-3-olate (Strem, 0.050 mmol, 21.5 mg), ascorbic acid (Aldrich, 0.300 mmol, 52.8 mg), DIPEA (Aldrich, 1 mmol, 129 mg), 2,6-dimethylpyridine (Aldrich, 1 mmol, 107 mg), (S)-tert-butyl 4-((((9H-fluoren-9-yl)methoxy)carbonyl)amino)-2-azidobutanoate (0.130 mmol, 54.9 mg) in DMF (1.4 mL) and THF (1.4 mL) was added to the resin-bound linear peptide from Step B (0.1 mmol). The reaction mixture was rocked for 16 h. The reagents were drained from the reaction vessel, and the resin was washed three times with DMF (8 mL×5 min) to give the title resin-supported product.

LCMS analysis was performed on a peptide aliquot which was cleaved from the resin (analytical amount of the resin was treated with HFIPA (20% solution of hexaflouroisopropanol in $CH_2Cl_2$, 0.5 mL) at rt for 120 min and then filtered through a syringe filter to give a solution of the free peptide. MS(ESI+) m/z 1087.6 (M+H).

D) Step D

On a Symphony Peptide Synthesizer (Protein Technology Inc. Tucson, Ariz.), resin from Step C (0.100 mmol) was swelled with DMF (7 mL×4 min) and mixed with a gentle stream of $N_2$ every 30 seconds. The solvent was drained and the following method was used to couple the first amino acid: the Fmoc group was removed from the resin-supported building block by washing the resin twice with a solution of 20% piperidine in DMF (5 mL and 2.5 min per wash) and mixing with a gentle stream of $N_2$ every 30 seconds. The resin was washed three times with DMF (8 mL and 1.5 min per wash). (S)-2-((((9H-fluoren-9-yl)methoxy)carbonyl)amino)-3-(naphthalen-2-yl)propanoic acid (Chem-Impex Int'l Inc, 0.2 M solution in DMF, 5 mL, 1 mmol) was then added, followed by HATU (Chem-Impex Int'l, 0.4M solution in DMF, 2.5 mL, 1 mmol) and N-methylmorpholine (Aldrich, 0.8 M in DMF, 2.5 mL, 2 mmol). The reaction mixture was agitated by a gentle stream of nitrogen for 1 h. The reagents were drained from the reaction vessel, and the resin was washed three times with DMF (8 mL×1.5 min).

The resulting resin-supported Fmoc-protected dipeptide was then sequentially deprotected and coupled with (2S,3S)-1-(((9H-fluoren-9-yl)methoxy)carbonyl)-3-(prop-2-yn-1-yloxy)pyrrolidine-2-carboxylic acid (1 mmol, 1 h), followed by (S)-2-((((9H-fluoren-9-yl)methoxy)carbonyl)amino)-3,3-dimethylbutanoic acid (Chem-Impex Int'l Inc, 1 mmol, 3 h), and then (S)-2-((tert-butoxycarbonyl)(methyl)amino)propanoic acid (Chem-Impex Int'l Inc, 1 mmol, 1 h) to give the title resin-supported product.

LCMS analysis was performed on an aliquot of the peptide cleaved from the resin (analytical amount of the resin was treated with HFIPA (20% solution hexaflouroisopropanol in $CH_2Cl_2$, 0.2 mL) at rt for 120 min and then filtered through a syringe filter to give a solution of the free peptide). MS(ESI+) m/z 1512.9 (M+H).

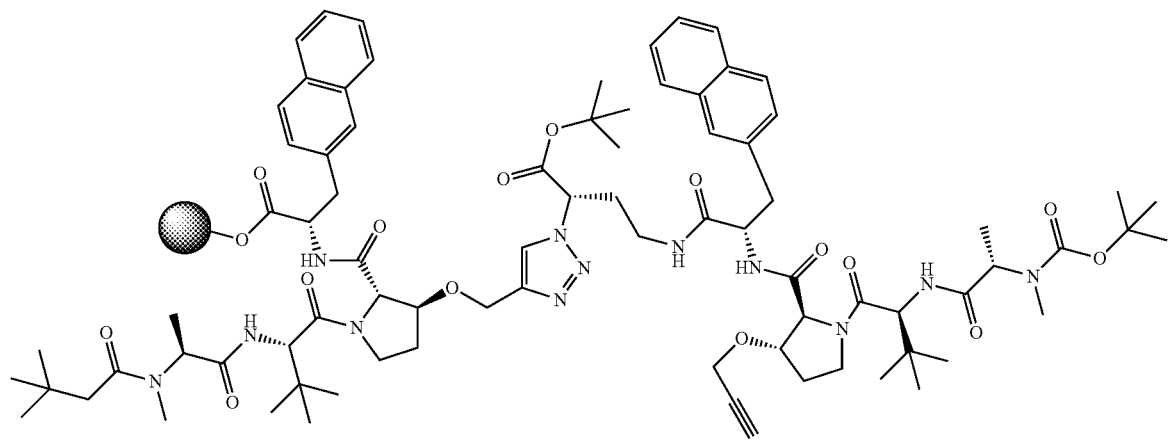 [SMILES: C#CCO[C@H]1CCN(C(=O)[C@@H](NC(=O)[C@H](C)N(C)C(=O)OC(C)(C)C)C(C)(C)C)[C@@H]1C(=O)N[C@@H](Cc1ccc2ccccc2c1)C(=O)NCC[C@@H](C(=O)OC(C)(C)C)n1cc(CO[C@H]2CCN(C(=O)[C@@H](NC(=O)[C@H](C)N(C)C(=O)CC(C)(C)C)C(C)(C)C)[C@@H]2C(=O)N[C@@H](Cc2ccc3ccccc3c2)C(=O)OC)nn1]

E) Step E

A freshly made solution of copper(II) (Z)-2,2,6,6-tetramethyl-5-oxohept-3-en-3-olate (Strem, 0.050 mmol, 21.5 mg), ascorbic acid (Aldrich, 0.300 mmol, 52.8 mg), DIPEA (Aldrich, 1 mmol, 129 mg), 2,6-dimethylpyridine (Aldrich, 1 mmol, 107 mg), (S)-tert-butyl 4-((((9H-fluoren-9-yl)methoxy)carbonyl)amino)-2-azidobutanoate (0.130 mmol, 54.9 mg), in DMF (1.4 mL) and THF (1.4 mL) was added to the resin bound linear peptide from Step D (0.1 mmol) in a Bio-Rad tube. The reaction mixture was rocked for 16 h. The reagents were drained from the reaction vessel, and the resin was washed three times with DMF (8 mL×5 min) to give the title resin-supported product.

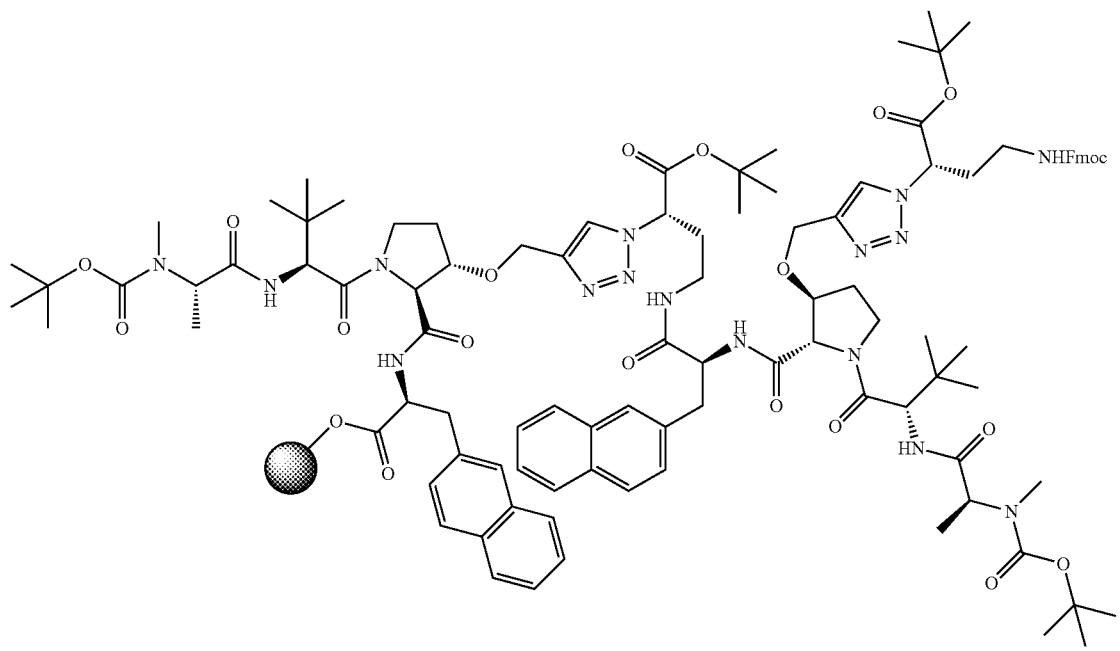

LCMS analysis was performed on an aliquot of the peptide cleaved from the resin (analytical amount of the resin was treated with HFIPA (20% solution of hexaflouroisopropanol in CH$_2$Cl$_2$, 0.5 mL) at rt for 120 min and then filtered through a syringe filter to give a solution of the free peptide). MS(ESI) m/z 1935.1 (M+1), 968.1 (M+2).

F) Step F

A freshly made solution of 25% piperidine (250 μL) in DMF (750 μL) was added to the resin bound linear peptide from Step E (0.1 mmol) in a Bio-Rad tube. The reaction mixture was rocked for 30 min. The reagents were drained from the reaction vessel, and the resin was washed three times with DMF (3 mL×5 min), then CH$_2$Cl$_2$ (3 mL×5 mins) to give the title resin-supported product.

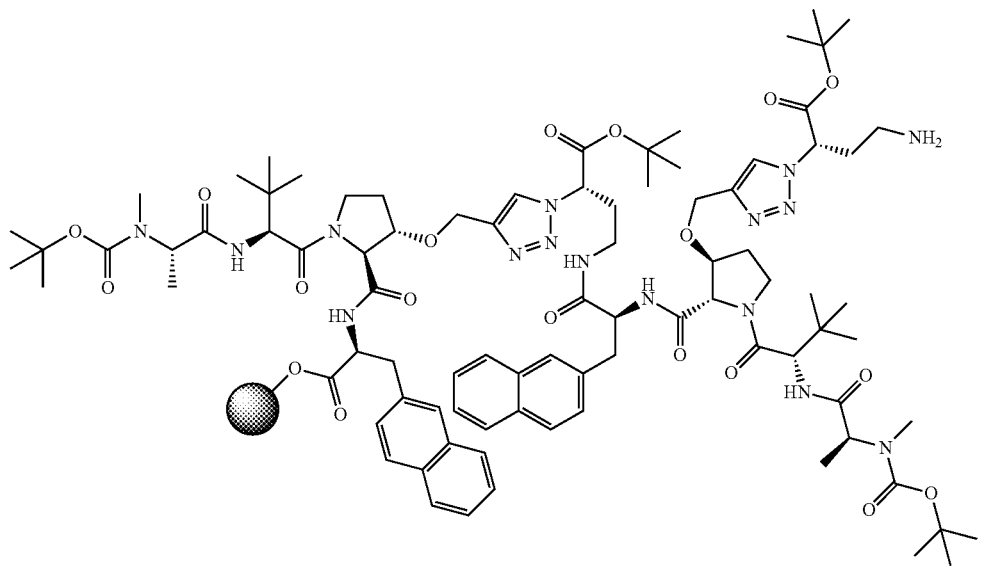 [SMILES: COC(=O)[C@H](Cc1ccc2ccccc2c1)NC(=O)[C@@H]1[C@@H](OCc2cn([C@@H](CCNC(=O)[C@H](Cc3ccc4ccccc4c3)NC(=O)[C@@H]3[C@@H](OCc4cn([C@@H](CCN)C(=O)OC(C)(C)C)nn4)CCN3C(=O)[C@@H](NC(=O)[C@H](C)N(C)C(=O)OC(C)(C)C)C(C)(C)C)C(=O)OC(C)(C)C)nn2)CCN1C(=O)[C@@H](NC(=O)[C@H](C)N(C)C(=O)OC(C)(C)C)C(C)(C)C]

LCMS analysis was performed on an aliquot of peptide cleaved from the resin (analytical amount of the resin was treated with HFIPA (20% solution of hexaflouroisopropanol in CH$_2$Cl$_2$, 0.5 mL) at room temperature for 2 h and then filtered through a syringe filter to give a solution of the free peptide). MS(ESI$^+$) m/z 1712.0 (M+1), 856.7 (M+2).

H) Compound H

To a solution of Compound G (55.8 mg, 0.033 mmol) in CH$_2$Cl$_2$ (148 mL) at 0° C. was added N-isopropyl-N-methylpropan-2-amine (11.3 mg, 0.098 mmol) and 2-(3H-[1,2,3]triazolo-[4,5-b]pyridin-3-yl)-1,1,3,3-tetramethyl-

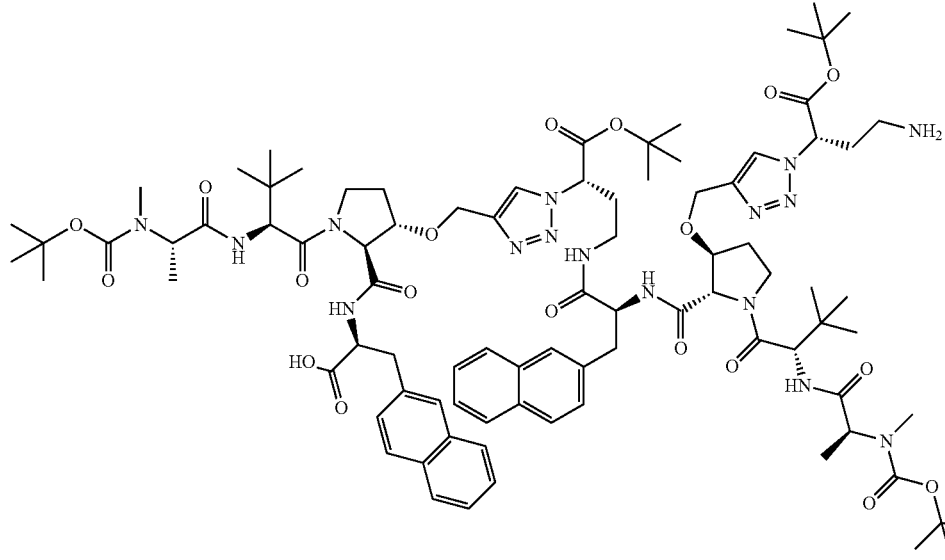

G) Compound G

A freshly made solution of 20% hexaflouroisoproanol (600 µL) in CH$_2$Cl$_2$ (2.4 mL) was added to the resin bound linear peptide from Step F (0.1 mmol) in a Bio-Rad tube. The reaction mixture was shaken at rt for 2 h, and the filtrate was collected. The resin was washed with CH$_2$Cl$_2$ (2×4 mL). The filtrate and washes were combined and concentrated in vacuo to produce an oil, which was purified by reverse phase preparative HPLC (C18 21.2×250 mm, Phenominex Luna) to afford Compound G (55.8 mg, 33%) as a white solid. MS(ESI$^+$) rt 1.1 min, m/z 1712.9 (M+1), 856.7 (M+2).

isouronium hexafluorophosphate(V) (37.2 mg, 0.098 mmol) in DMF (14.8 mL). The resulting reaction mixture was allowed to warm to rt. After 6 h the solution was concentrated in vacuo and the crude material was purified by reverse phase preparative HPLC (C18 21.2×250 mm, Phenominex Luna) to afford Compound H (30.2 mg, 55%) as a white solid. MS(ESI$^+$) rt 1.1 min, m/z 1695.0 (M+1), 847.7 (M+2).

I) Example 2

To a solution of Compound H (30.2 mg, 0.018 mmol) in CH$_2$Cl$_2$ (5 mL) was added TFA (2 mL). The reaction mixture was stirred at rt for 6 h and then concentrated in vacuo. The resulting oil residue was purified by reverse phase preparative HPLC to give the TFA salt of Example 2 (7.9 mg, 26.9%) as a white solid after lyophilization. MS (ESI$^+$) rt 0.71 min, m/z 1382.8 (M+1), 691.5 (M+2). HPLC Purity: Phenomenex Luna 5 u C18(2) 150×4.6 mm, 10-100% B, 20 min gradient, 1 mL/min flow rate (rt 11.76 min, 98%); mobile A (0.1% TFA H$_2$O), mobile B (0.1% TFA MeCN).

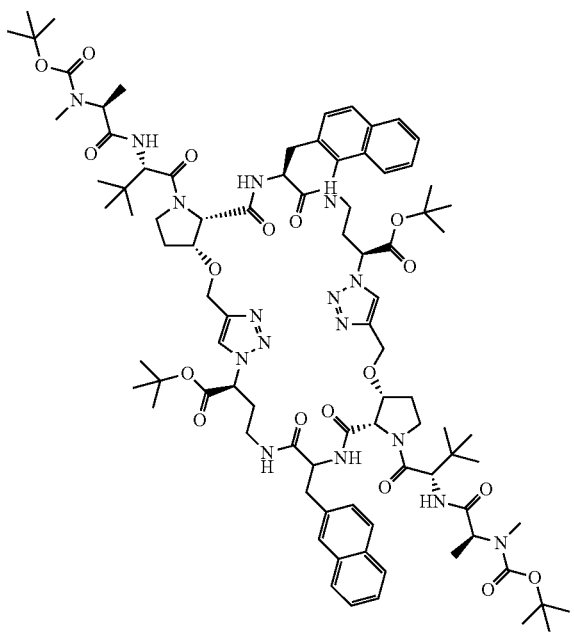 [SMILES: C[C@@H](C(=O)N[C@H](C(=O)N1CC[C@H]2OCc3cn(nn3)[C@H](C(=O)OC(C)(C)C)CCN3C(=O)[C@H](Cc4ccc5ccccc5c43)NC(=O)[C@@H]3[C@@H](CCN3C(=O)[C@@H](NC(=O)[C@H](C)N(C)C(=O)OC(C)(C)C)C(C)(C)C)OCc3cn(nn3)[C@H](C(=O)OC(C)(C)C)CCNC(=O)C(Cc3ccc4ccccc4c3)NC(=O)[C@H]21)C(C)(C)C)N(C)C(=O)OC(C)(C)C]

Examples 3-6

The following examples were prepared according to the procedures described for the synthesis of Example 2.

| Ex No | Structure | MW | Observed LCMS |
|---|---|---|---|
| 3 | 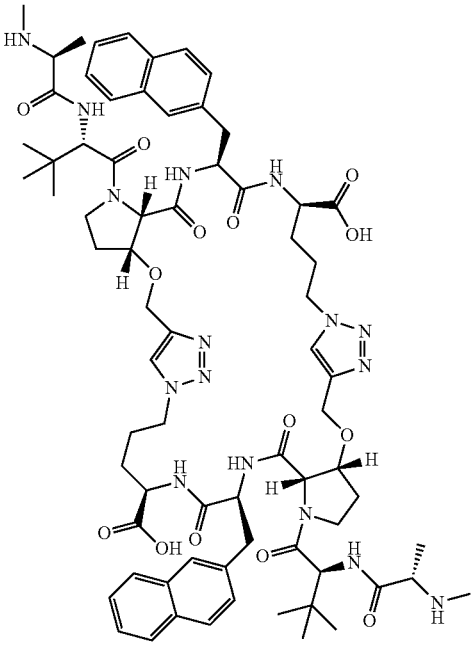 [SMILES: CN[C@@H](C)C(=O)N[C@H](C(=O)N1CC[C@H]2OCc3cn(nn3)CCC[C@H](C(=O)O)NC(=O)[C@H](Cc3ccc4ccccc4c3)NC(=O)[C@@H]3[C@@H](CCN3C(=O)[C@@H](NC(=O)[C@H](C)NC)C(C)(C)C)OCc3cn(nn3)CCC[C@H](C(=O)O)NC(=O)[C@H](Cc3ccc4ccccc4c3)NC(=O)[C@H]21)C(C)(C)C] | 1409.65 | 1409.5 |
| 4 | 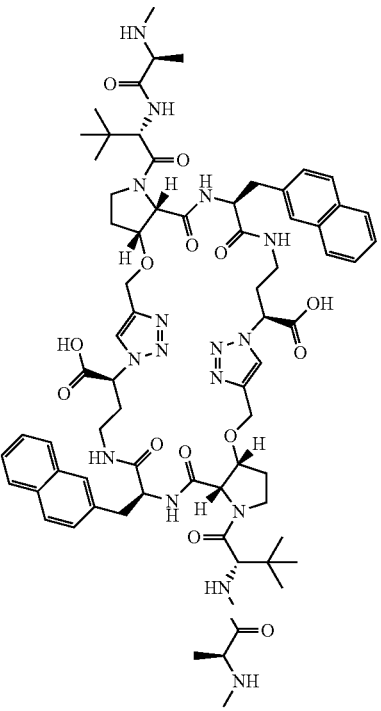 | 1381.59 | 1382.8 |

-continued

| Ex No | Structure | MW | Observed LCMS |
|---|---|---|---|
| 5 | 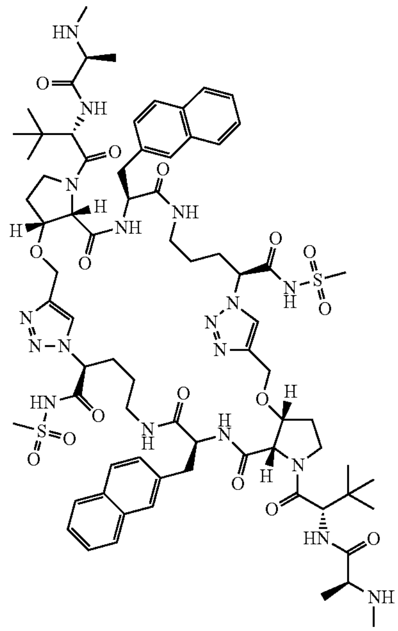 [SMILES: CN[C@@H](C)C(=O)N[C@H](C(=O)N1CC[C@H]2OCc3cn(nn3)[C@H](C(=O)NS(C)(=O)=O)CCCNC(=O)[C@H](Cc3ccc4ccccc4c3)NC(=O)[C@@H]3[C@@H](CCN3C(=O)[C@@H](NC(=O)[C@H](C)NC)C(C)(C)C)OCc3cn(nn3)[C@H](C(=O)NS(C)(=O)=O)CCCNC(=O)[C@H](Cc3ccc4ccccc4c3)NC(=O)[C@H]21)C(C)(C)C] | 1563.86 | 782.5 M + 2 |
| 6 | 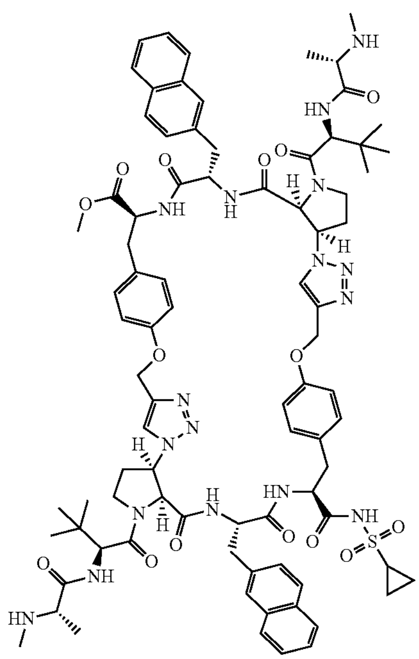 [SMILES: CN[C@@H](C)C(=O)N[C@H](C(=O)N1CC[C@@H]2[C@H]1C(=O)N[C@@H](Cc1ccc3ccccc3c1)C(=O)N[C@H](C(=O)NS(=O)(=O)C1CC1)Cc1ccc(cc1)OCc1cn(nn1)[C@@H]1CCN(C(=O)[C@@H](NC(=O)[C@H](C)NC)C(C)(C)C)[C@@H]1C(=O)N[C@@H](Cc1ccc3ccccc3c1)C(=O)N[C@H](C(=O)OC)Cc1ccc(cc1)OCc1cn2nn1)C(C)(C)C] | 1622.91 | 812.0 M + 2 |

Example 7

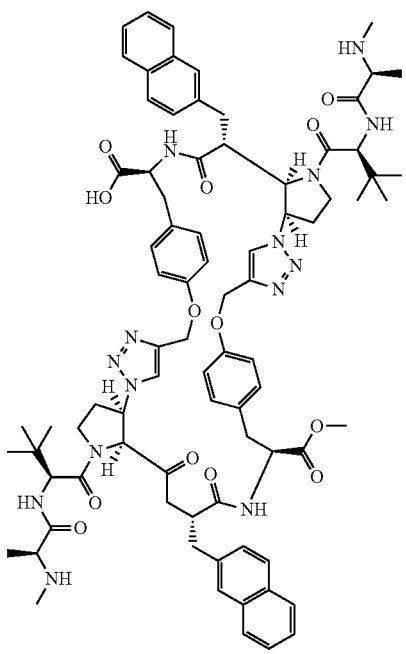 [SMILES: CN[C@@H](C)C(=O)N[C@H](C(=O)N1CC[C@@H]2[C@H]1[C@@H](Cc1ccc3ccccc3c1)C(=O)N[C@H](C(=O)O)Cc1ccc(cc1)OCc1cn(nn1)[C@@H]1CCN(C(=O)[C@@H](NC(=O)[C@H](C)NC)C(C)(C)C)[C@@H]1C(=O)C[C@@H](Cc1ccc3ccccc3c1)C(=O)N[C@H](C(=O)OC)Cc1ccc(cc1)OCc1cn2nn1)C(C)(C)C]

Compound N of Example 1 (14.1 mg, 8.20 umol) in a 1 dram vial equipped with a magnetic stir bar was treated with $CH_2Cl_2$ (1 mL) and TFA (1 mL), and the resulting solution was stirred at rt until complete conversion was observed by LCMS (MS (ESI+) rt 0.77 min, m/z 1520.0 (M+1), 760.9 (M+2)). The solvent was removed in vacuo and the crude material was purified by reverse phase preparative HPLC (C18 Luna 30×250 mm, MeCN in $H_2O$ containing 0.1% TFA) to afford Example 7 (8.2 mg, 57%) as a white solid. MS (ESI+) rt 0.77 min, m/z 1520.5. HPLC Purity: Phenomenex Luna 5u C18(2) 150×4.6, 10-100% B, 20 min gradient, 1 mL/min flow rate (rt 13.971 min, 100%); mobile A (0.1% TFA $H_2O$), mobile B (0.1% TFA MeCN).

Examples 8 and 9

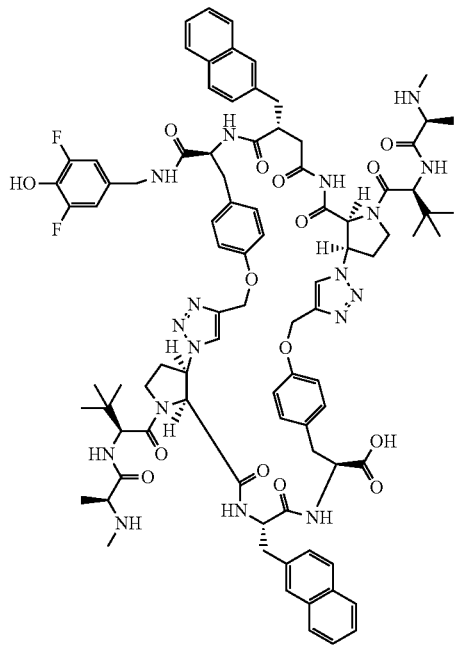

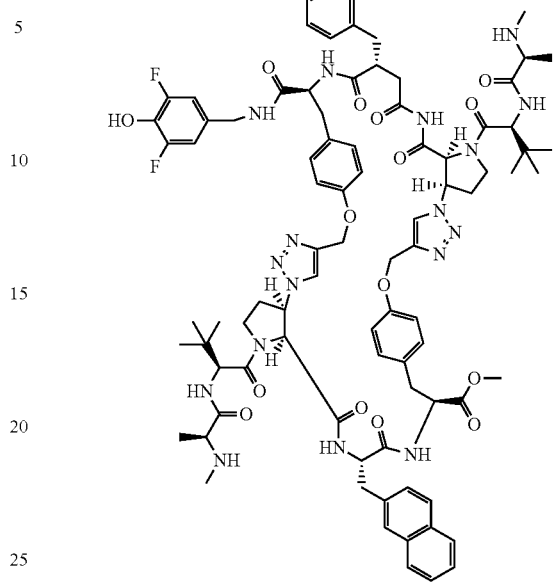

A solution of Compound N of Example 1 (17.6 mg, 10.2 μmol) and (3,5-difluoro-4-methoxyphenyl)-methanamine (4.2 mg, 0.024 mmol) in $CH_2Cl_2$ (1 mL) was treated with a solution of O-(7-azabenzotriazol-1-yl)-N,N,N',N'-tetramethyluronium hexafluorophosphate (5.84 mg, 0.015 mmol) and N-ethyl-N-isopropylpropan-2-amine (3.56 μl, 0.020 mmol) in DMF (100 μl) at rt. Upon complete conversion of the starting material, the reaction mixture was washed with $H_2O$ (0.5 mL) and 1N HCl (0.5 mL). The organics were dried over $MgSO_4$, filtered through an SPE washing with $CH_2Cl_2$, and concentrated in vacuo to a yellow oil (MS (ESI+) rt 1.12 min, m/z 1876.0 (M+1), 938.4 (M+2)).

The resulting crude material was dissolved in $CH_2Cl_2$ (1 mL) and TMS-I (13.93 μL, 0.102 mmol) was added to the solution. The reaction mixture was stirred at rt to 40° C. overnight. The reaction was quenched with 1N HCl (3 mL), washed with brine (2 mL) and extracted with $CH_2Cl_2$ (4×). The combined organic extracts were dried over $MgSO_4$, filtered and concentrated in vacuo. The crude residue was purified by reverse phase preparative HPLC (C18 30×250 mm, Phenominex Luna) to afford Example 8 (white solid, 4.3 mg) and Example 9 (white solid, 2.7 mg).

Example 8: MS (ESI+) rt 0.75 min, m/z 1646.4 (M+1), 824.4 (M+2). HPLC Purity: Phenomenex Luna 5u C18(2) 150×4.6, 10-100% B, 20 min gradient, 1 mL/min flow rate (rt 14.012 min, 90%); mobile A (0.1% TFA water), mobile B (0.1% TFA MeCN). Example 9: MS (ESI+) rt 0.78 min, m/z 1662.6 (M+1), 831.4 (M+2). HPLC Purity: Phenomenex Luna 5u C18(2) 150×4.6, 10-100% B, 20 min gradient, 1 mL/min flow rate (rt 14.36 min, 94%); mobile A (0.1% TFA $H_2O$), mobile B (0.1% TFA MeCN).

Example 10

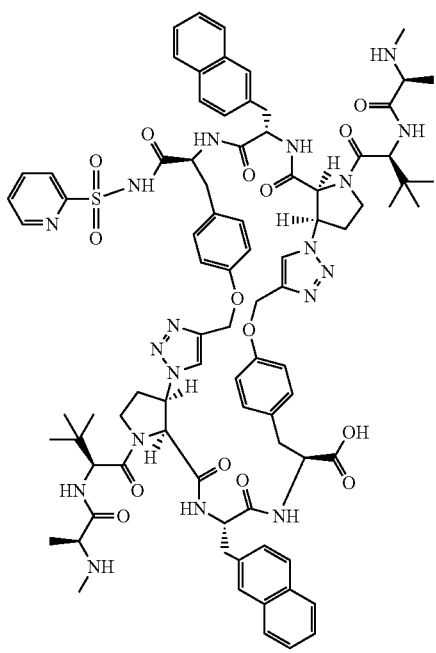 [SMILES: CN[C@@H](C)C(=O)N[C@H](C(=O)N1CC[C@@H]2[C@H]1C(=O)N[C@@H](Cc1ccc3ccccc3c1)C(=O)N[C@H](C(=O)O)Cc1ccc(cc1)OCc1cn(nn1)[C@@H]1CCN(C(=O)[C@@H](NC(=O)[C@H](C)NC)C(C)(C)C)[C@@H]1C(=O)N[C@@H](Cc1ccc3ccccc3c1)C(=O)N[C@H](C(=O)NS(=O)(=O)c1ccccn1)Cc1ccc(cc1)OCc1cn2nn1)C(C)(C)C]

Compound N of Example 1 (35 mg, 0.020 mmol) in THF (500 μL) was treated with a solution of CDI (3.27 mg, 0.020 mmol) in $CH_2Cl_2$ (500 μL) at rt in an oven dried vial. After 2 h, pyridine-2-sulfonamide (3.19 mg, 0.020 mmol) and DBU (3.04 μL, 0.020 mmol) in THF (500 μL) were added and the resulting mixture was stirred for 4 h before being quenched 1N HCl. The mixture was extracted with $CH_2Cl_2$ (3×), and the combined organics were dried over $MgSO_4$, filtered and concentrated in vacuo. The crude material was purified by reverse phase preparative HPLC (C18 30×250 mm, Phenominex Luna) to afford the crude product (5 mg)—MS (ESI+) rt 1.18 min, m/z 1860.8 (M+1), which was dissolved in MeOH (0.5 mL) and THF (0.5 mL) and treated with 2M LiOH (15 μL). Upon completion of the hydrolysis step, the solution was acidified with 1N HCl (0.5 mL) and concentrated to dryness. The residue was taken up in TFA (1 mL) and $CH_2Cl_2$ (1 mL) at rt to effect the Boc removal prior to concentrating the solvent in vacuo. The crude yellow oil was purified by reverse phase preparative HPLC (C18 30×100 mm, Phenominex Luna) to afford Example 10 (white solid, 4 mg). MS (ESI+) rt 0.76 min, m/z 823.9 (M+2). HPLC Purity: Phenomenex Luna 5u C18(2) 150× 4.6, 10-100% B, 20 min gradient, 1 mL/min flow rate (rt 14.064 min, 90%); mobile A (0.1% TFA $H_2O$), mobile B (0.1% TFA MeCN).

Examples 11-12

The following examples were prepared according to the procedures described for the synthesis of Example 10.

| Ex No | Structure | Observed MW | LCMS |
|---|---|---|---|
| 11 | 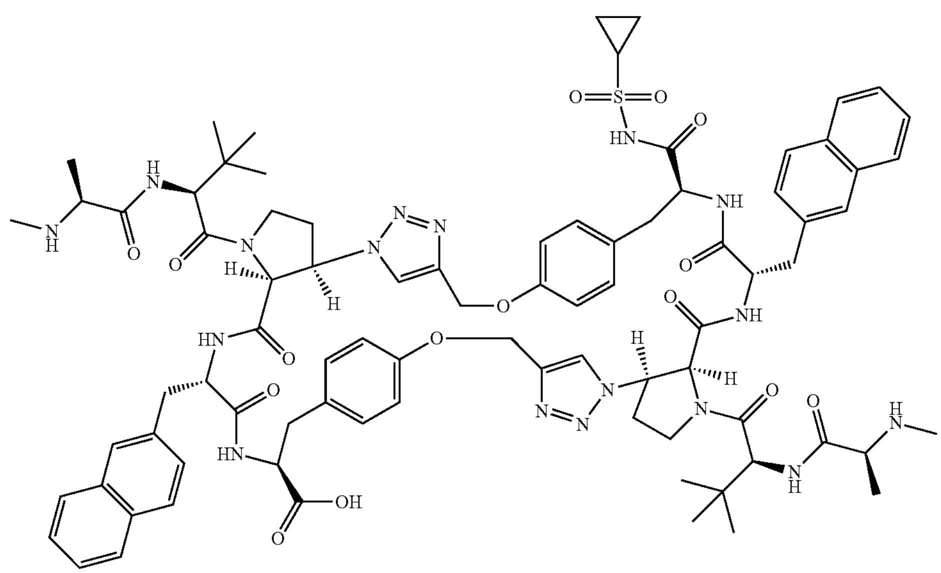 | 1608.88 | 1609.9 |

| Ex No | Structure | MW | Observed LCMS |
|---|---|---|---|
| 12 | 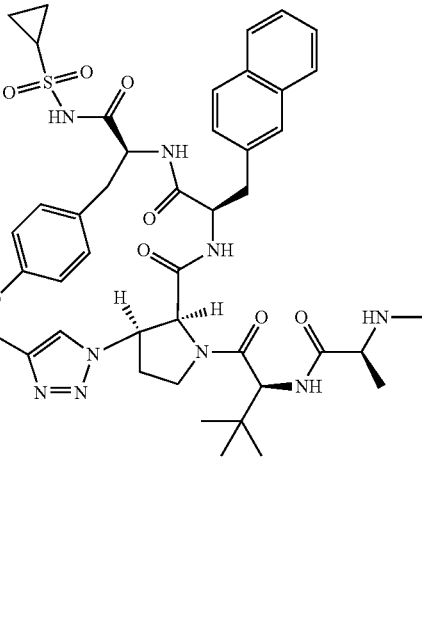 | 1608.88 | 805.44 M + 2 |

Example 13

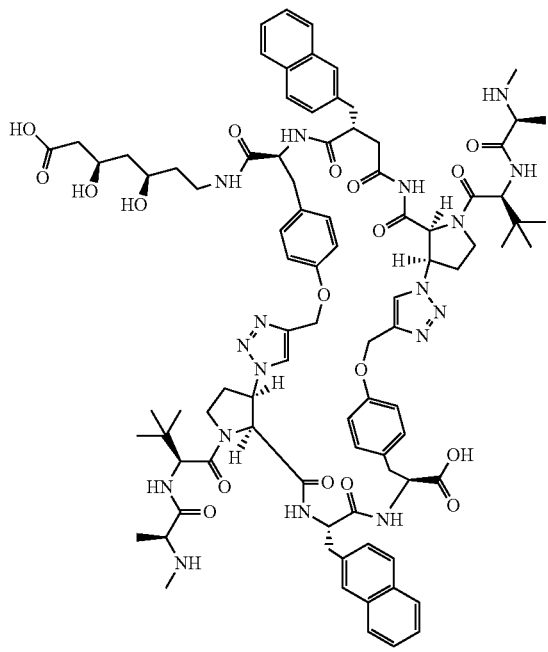 [SMILES: CN[C@@H](C)C(=O)N[C@H](C(=O)N1CC[C@@H]2[C@H]1C(=O)NC(=O)C[C@@H](Cc1ccc3ccccc3c1)C(=O)N[C@H](C(=O)NCC[C@@H](O)C[C@@H](O)CC(=O)O)Cc1ccc(cc1)OCc1cn(nn1)[C@@H]1CCN(C(=O)[C@@H](NC(=O)[C@H](C)NC)C(C)(C)C)[C@@H]1C(=O)N[C@@H](Cc1ccc3ccccc3c1)C(=O)N[C@H](C(=O)O)Cc1ccc(cc1)OCc1cn2nn1)C(C)(C)C]

Compound N of Example 1 (26.3 mg, 0.015 mmol) and tert-butyl 2-((4R,6R)-6-(2-aminoethyl)-2,2-dimethyl-1,3-dioxan-4-yl)acetate (4.18 mg, 0.015 mmol) in CH$_2$Cl$_2$ (1 mL) was treated with a solution of O-(7-azabenzotriazol-1-yl)-N,N,N',N'-tetramethyluronium hexafluorophosphate (8.72 mg, 0.023 mmol) and N-ethyl-N-isopropylpropan-2-amine (5.33 µL, 0.031 mmol) in DMF (100 µl) at rt overnight. The reaction mixture was quenched with H$_2$O (0.5 mL) and 1N HCl (0.5 mL). The mixture was extracted with CH$_2$Cl$_2$ (2×), and the combined organics were dried over MgSO4, filtered, and concentrated in vacuo. The resulting yellow oil was dissolved in MeOH (0.5 mL) and THF (0.5 mL) and treated with 2 M LiOH (22.94 µL, 0.046 mmol). The solution was acidified with 1N HCl (0.25 mL), washed with brine (0.5 mL), and extracted with CH$_2$Cl$_2$ (3×). The combined organics were dried over MgSO$_4$, filtered and concentrated to a solid. The residue was dissolved in CH$_2$Cl$_2$ (1 mL) and TFA (1 mL) at rt, monitored for conversion by LCMS, and upon completion the solvent was removed. The resulting crude oil was purified by reverse phase prep HPLC (C18 30×100 mm, Phenominex Luna) to afford Example 13 (12.1 mg) as a white solid. MS (ESI+) rt 0.71 min, m/z 833.2 (M+2). HPLC Purity: Phenomenex Luna 5u C18(2) 150×4.6, 10-100% B, 20 min gradient, 1 mL/min flow rate (rt 13.28 min, 95%); mobile A (0.1% TFA H$_2$O), mobile B (0.1% TFA MeCN).

Example 14

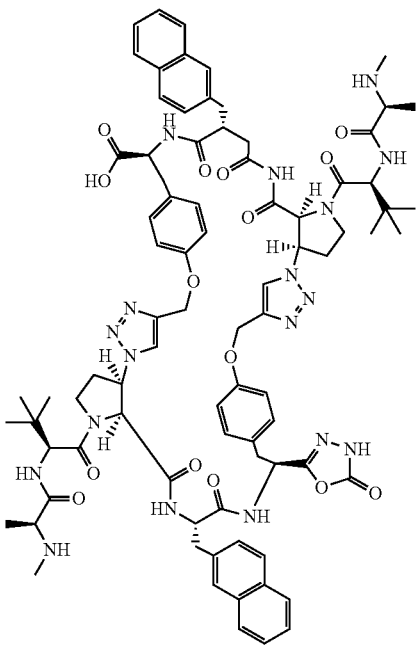 [SMILES: CN[C@@H](C)C(=O)N[C@H](C(=O)N1CC[C@@H]2[C@H]1C(=O)NC(=O)C[C@@H](Cc1ccc3ccccc3c1)C(=O)N[C@H](C(=O)O)Cc1ccc(cc1)OCc1cn(nn1)[C@@H]1CCN(C(=O)[C@@H](NC(=O)[C@H](C)NC)C(C)(C)C)[C@@H]1C(=O)N[C@@H](Cc1ccc3ccccc3c1)C(=O)N[C@H](c1n[nH]c(=O)o1)Cc1ccc(cc1)OCc1cn2nn1)C(C)(C)C]

Compound N of Example 1 (45 mg, 0.026 mmol) was treated with hydrazine, H$_2$O (220 µL, 4.49 mmol) and heated to 85° C. until conversion to the amide was observed by LCMS. Upon conversion, the reaction mixture was cooled to rt, the solvent was removed and the residue was purified by reverse phase preparative HPLC (C18 30×250 mm, Phenominex Luna) to afford a white solid (MS (ESI+) rt 1.07 min, m/z 1720.2). To this solid was added di(1H-imidazol-1-yl)methanone (19.09 mg, 0.118 mmol) in THF (900 µL) and DMF (90 µL). The mixture was warmed to 85° C. for 4 h until complete conversion of the starting material was observed. The solution was then cooled to rt, washed with H$_2$O (0.5 mL) and concentrated to an oil. The residue was taken up in CH$_2$Cl$_2$ (0.5 mL) and TFA (0.5 mL), stirred at rt for 30 min, and concentrated in vacuo. The resulting yellow oil was further purified by reverse phase preparative HPLC (C18 30×100 mm, Phenominex Luna) to afford Example 14 (2.3 mg, 5%) as a white solid. MS (ESI+) rt 0.73 min, m/z 1548.1 (M+1), 773.6 (M+2). HPLC Purity: Phenomenex Luna 5u C18(2) 150×4.6, 10-100% B, 20 min gradient, 1 mL/min flow rate (rt 13.581 min, 99.6%); mobile A (0.1% TFA H$_2$O), mobile B (0.1% TFA MeCN).

Examples 15 and 16

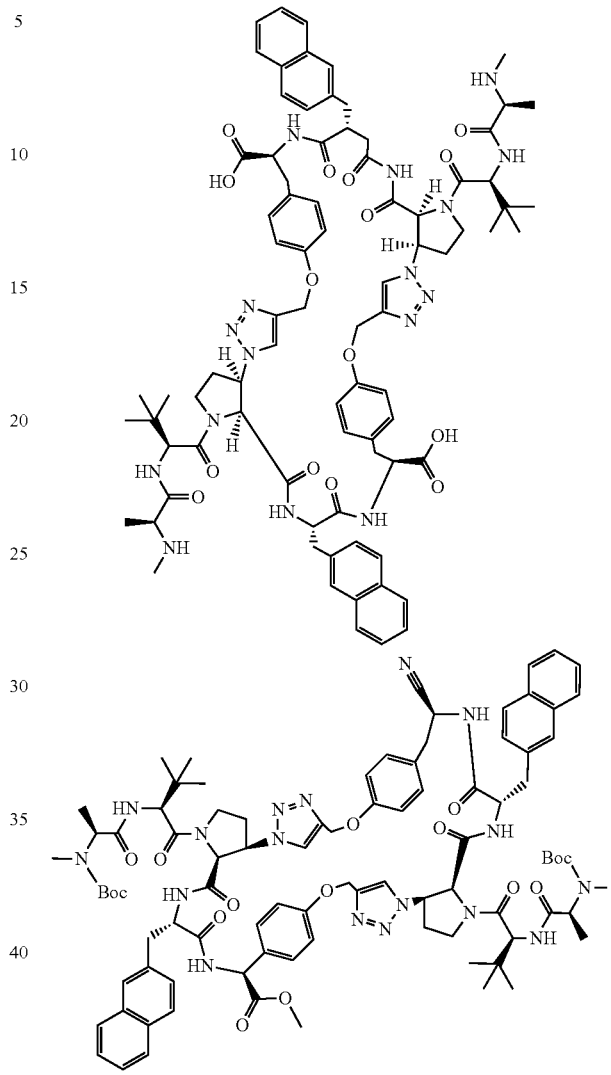

A) Compound A

To a solution of Compound N of Example 1 (210 mg, 0.122 mmol) and DIPEA (64.1 µL, 0.367 mmol) in THF (1112 µL) at −10° C. was added drop wise isobutyl carbonochloridate (23.9 µL, 0.183 mmol). The resulting mixture was stirred at −10° C. for 130 min (monitored by LCMS upon quenching small aliquots into MeOH). Upon formation of the activated ester, a solution of 7N NH$_3$ in MeOH (157 µL, 1.101 mmol) was added via syringe and the resulting mixture was slowly warmed to rt. The reaction mixture was then quenched with a pre-mixed solution of brine (1 mL) and 1N HCl (0.2 mL). The mixture was extracted with EtOAc (3×50 mL), dried over MgSO$_4$, filtered, and concentrated in vacuo. To a solution of this tan solid dissolved in CH$_2$Cl$_2$/THF (1:1, 1 mL), was added Burgess reagent (43.7 mg, 0.183 mmol) in one portion. The resulting mixture was stirred for 45 min (MS (ESI+) rt 1.19 min, m/z 1701.0). The solvent was removed to dryness and the crude was purified by reverse phase ISCO (C18 Gold 43 g column 20-95% MeCN in H$_2$O with 0.1% TFA) to Compound A (182.8 mg) as a tan solid. MS (ESI+) rt 1.18 min, m/z 1702.1. This material was used directly in the next step.

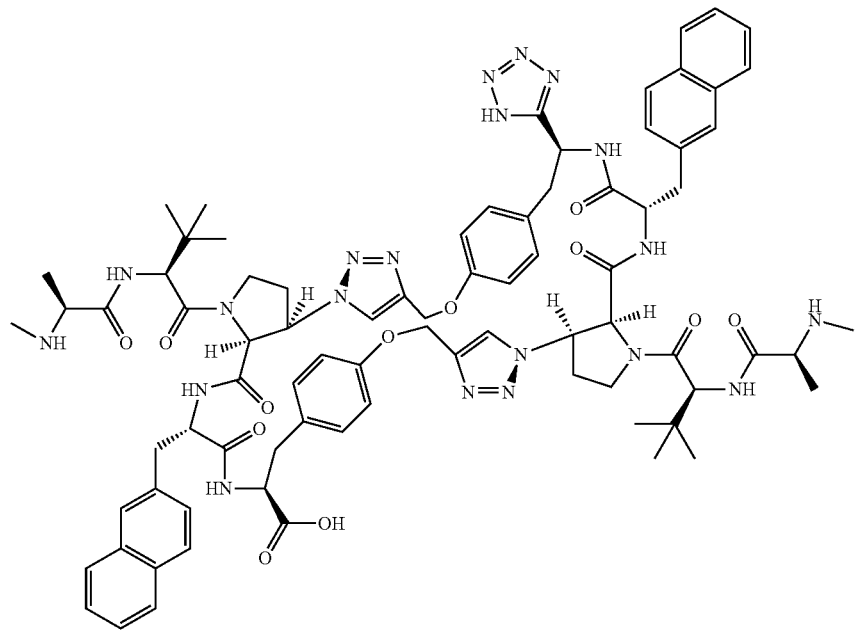

B) Examples 15-16

To a vial containing Compound A (40 mg, 0.024 mmol) and DMF (1.5 mL) was added NaN$_3$ (11 mg, 0.17 mmol). The reaction mixture was warmed to 80° C., treated with Zn(II) bromide (5.30 mg, 0.024 mmol) and stirred at 80° C. for 2 d. The mixture was taken up in DMF (2 mL) and the crude material was purified by reverse phase preparative HPLC (C18, 30×100 mm, Phenominex Luna, 10-100% MeCN with 0.1% TFA in H$_2$O with 0.1% TFA) to afford two fractions of tetrazole—isomer A (8.2 mg) and isomer B (3.5 mg). These to fractions were taken through the sequence separately. Each vial was treated with THF (0.5 mL), MeOH (0.5 mL) and 2M LiOH (9.40 μl, 0.019 mmol). Upon completion of the hydrolysis step, the vials were acidified with 1N HCl (0.2 mL) and the solvent was removed in vacuo. The residues were redissolved in TFA (0.5 mL), CH$_2$Cl$_2$ (0.5 mL) and H$_2$O (0.1 mL). The resulting solution was stirred at rt until deprotection was affected at which point the solvent was removed. The crudes were purified by reverse phase preparative HPLC (C18 30×100 mm, 0-100% MeCN with 0.1% TFA in H$_2$O with 0.1% TFA over 18 min) to afford a major isomer, Example 15 (2.9 mg, white solid), and a minor isomer, Example 16 (1.4 mg, white solid).

Example 15: MS (ESI+) rt 0.73 min, m/z 765.8 (M+2); HPLC Purity: Phenomenex Luna 5u C18(2) 150×4.6, 10-100% B, 20 min gradient, 1 mL/min flow rate (rt 13.701 min, 99.8%); mobile A (0.1% TFA H$_2$O), mobile B (0.1% TFA MeCN). Example 16: MS (ESI+) rt 0.75 min, m/z 766.0 (M+2); HPLC Purity: Phenomenex Luna 5u C18(2) 150× 4.6, 10-100% B, 20 min gradient, 1 mL/min flow rate (rt 13.906 min, 99.7%); mobile A (0.1% TFA H$_2$O), mobile B (0.1% TFA MeCN).

Examples 17 and 18

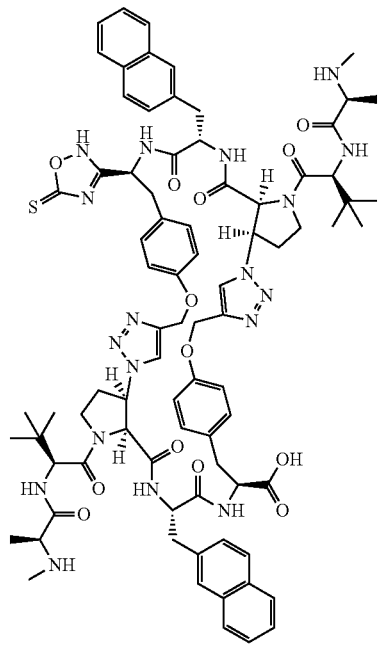

To a solution of Compound A of Examples 15 and 16 (32.9 mg, 0.019 mmol) and MeOH (1 mL) was added solid NaHCO$_3$ (1.787 mg, 0.021 mmol) followed by hydroxylamine, HCl (1.411 mg, 0.020 mmol). The resulting mixture was heated to 70° C. overnight until the starting material was consumed. The solvent was removed and the residue was purified by reverse phase preparative HPLC (C18 30×100 mm, 0-100% MeCN in H$_2$O over 15 min) to afford the hydroxyacetimidamide intermediate (10.4 mg); MS (ESI+) rt 1.08 min, m/z 867.3 (M+2).

To a vial containing this intermediate (10.4 mg, 6.00 µmol) and DMF (1 mL) was added a solution of DBU (3.62 µl, 0.024 mmol), di(1H-imidazol-1-yl)methanethione (TDI, 1.635 mg, 9.18 µmol) in DMF (100 µL). The resulting mixture was stirred at rt and concentrated in vacuo. The residue was dissolved in THF (0.5 mL) and MeOH (0.5 mL) and treated with 2N LiOH (20 µL) at rt. Upon complete hydrolysis, the solution was acidified with 1N HCl (0.4 mL) and concentrated in vacuo. The resulting solid was redissolved in CH$_2$Cl$_2$ (1 mL) and TFA (1 mL) and stirred until the deprotection was complete. The mixture was concentrated in vacuo and the resulting residue was purified by reverse phase preparative HPLC (C18 30×100 mm, 0-100% MeCN in H$_2$O with 0.5% TFA as a modifier) to afford a major isomer, Example 17 (1.6 mg, white solid), and a minor isomer, Example 18 (1.3 mg, white solid).

Example 17: 1.6 mg, white solid; MS (ESI+) rt 0.76 min, m/z 782.5 (M+2); HPLC Purity: Phenomenex Luna 5u C18(2) 150×4.6, 10-100% B, 20 min gradient, 1 mL/min flow rate (rt 14.084 min, 95.2%); mobile A (0.1% TFA H$_2$O), mobile B (0.1% TFA MeCN). Example 18: 1.3 mg, white solid; MS (ESI+) rt 0.74 min, m/z 1561.6 (M+1), 781.6 (M+2); HPLC Purity: Phenomenex Luna 5u C18(2) 150× 4.6, 10-100% B, 20 min gradient, 1 mL/min flow rate (rt 14.422 min, 99.5%); mobile A (0.1% TFA H$_2$O), mobile B (0.1% TFA MeCN).

Examples 19 and 20

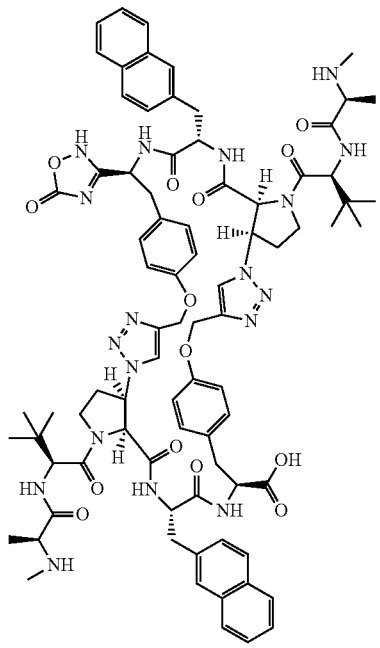 [SMILES: CN[C@@H](C)C(=O)N[C@H](C(=O)N1CC[C@@H]2[C@H]1C(=O)N[C@@H](Cc1ccc3ccccc3c1)C(=O)N[C@H](C(=O)O)Cc1ccc(cc1)OCc1cn(nn1)[C@@H]1CCN(C(=O)[C@@H](NC(=O)[C@H](C)NC)C(C)(C)C)[C@@H]1C(=O)N[C@@H](Cc1ccc3ccccc3c1)C(=O)N[C@H](c1nc(=O)o[nH]1)Cc1ccc(cc1)OCc1cn2nn1)C(C)(C)C]

Examples 19 and 20 were prepared as above with minor modifications to that outlined for Examples 17 and 18, including the substitution of CDI for TDI in the above experimental. Example 19: 1.6 mg, white solid; MS (ESI+) rt 0.74 min, m/z 1545.7 (M+1), 773.9 (M+2); HPLC Purity: Phenomenex Luna 5u C18(2) 150×4.6, 10-100% B, 20 min gradient, 1 mL/min flow rate (rt 13.816 min, 99.7%); mobile A (0.1% TFA H$_2$O), mobile B (0.1% TFA MeCN). Example 20: 1.3 mg, white solid; MS (ESI+) rt 0.76 min, m/z 1546.4 (M+1), 773.4 (M+2); HPLC Purity: Phenomenex Luna 5u C18(2) 150×4.6, 10-100% B, 20 min gradient, 1 mL/min flow rate (rt 14.189 min, 98.3%); mobile A (0.1% TFA H$_2$O), mobile B (0.1% TFA MeCN).

Evaluation of Biological Activity

Exemplary compounds were tested for inhibition of XIAP BIR3 and XIAP BIR2-3 activity. Experimental procedures and results are provided below.

A. XIAP-BIR3/SMAC Homogeneous Time Resolved Fluorescence (HTRF) Assay

Assays were performed in black, flat-bottom, 384-well plates. The final assay volume was 50 µL prepared from additions of His-BIR3 (241-356, XIAP), fluorescein labeled SMAC peptide, and test compounds in assay buffer consisting of 20 mM Sodium Phosphate, 1 mM EDTA, 50 mM NaCl, 50 µg/ml BSA, and 0.05% Pluronic F68. The reaction was incubated at room temperature for 60 minutes, following which 10 µl of mouse anti-6xHis-terbium labeled Fab (Medarex, Cis-bio) was added to the reaction (40 IA for an additional 30 minute incubation. The HTRF signal, ratio of fluorescence intensities at emission wavelengths for fluorescein acceptor (520 nm) and terbium donor (615 nm), the 520/615 ratio, generated by the reaction was then measured on the Envision Plate Reader Inhibition data were calculated from the 520/615 ratio generated by the no protein control reactions for 100% inhibition and vehicle-only reactions for 0% inhibition. The final concentration of reagents in the assay was 1 nM N-His-BIR3(241-356, XIAP), 5 nM fluorescein labeled SMAC peptide, 0.25 nM anti-His-Tb-Fab, and 0.1% DMSO. Dose response curves were generated to determine the concentration required for inhibiting 50% of the HTRF signal (IC$_{50}$). Compounds were dissolved at 3 mM in dimethylsulfoxide (DMSO) and evaluated at eleven serially diluted concentrations. IC$_{50}$ and K$_i$ values were derived by non-linear regression analysis.

B. XIAP-BIR2-3 Dimeric SMAC Peptide Homogeneous Time Resolved Fluorescence (HTRF) Assay Assays were performed in black, flat-bottom, 384-well plates. The final assay volume was 50 µL prepared from additions of His-BIR2-3 (125-356, C202A/C213G, XIAP), fluorescein labeled dimeric SMAC peptide, and test compounds in assay buffer consisting of 20 mM Sodium Phosphate, 1 mM EDTA, 50 mM NaCl, 50 µg/ml BSA, and 0.05% Pluronic F68. The reaction was incubated at room temperature for 60 minutes, following which 10 µl of mouse anti-6xHis-Tb IgG (Medarex, Cis-bio) was added to the reaction (40 µl) for an additional 30 minute incubation. The HTRF signal, ratio of fluorescence intensities at emission wavelengths for fluorescein acceptor (520 nm) and terbium donor (615 nm), the 520/615 ratio, generated by the reaction was then measured on the Envision Plate Reader. Inhibition data were calculated from the 520/615 ratio generated by the no protein control reactions for 100% inhibition and vehicle-only reactions for 0% inhibition. The final concentration of reagents in the assay was 0.5 nM N-His-BIR2-3(125-356, C202A/C213G, XIAP), 20 nM fluorescein labeled dimeric SMAC peptide, 0.25 nM anti-His-Tb-Fab, and 0.1% DMSO. Dose response curves were generated to determine the concentration required for inhibiting 50% of the HTRF signal ($IC_{50}$). Compounds were dissolved at 3 mM in dimethylsulfoxide (DMSO) and evaluated at eleven serially diluted concentrations. $IC_{50}$ and $K_i$ values were derived by non-linear regression analysis.

Results:

Results of the XIAP BIR3 and XIAP BIR2-3 assays are shown in the Table below.

TABLE

| Example Number | XIAP BIR3 FRET $IC_{50}$ (uM) | XIAP BIR2-3 FRET $IC_{50}$ (uM) |
| --- | --- | --- |
| 1 | 0.0049 | 0.0011 |
| 2 | 0.0165 | 0.0052 |
| 3 | 0.0019 | 0.0008 |
| 4 | 0.0578 | 0.0016 |
| 5 | 0.0510 | 0.0080 |
| 6 | 0.0146 | 0.0024 |
| 7 | 0.0290 | 0.0065 |
| 8 | 0.0091 | 0.0012 |
| 9 | 0.0139 | 0.0027 |
| 10 | 0.0631 | 0.0169 |
| 11 | 0.0103 | 0.0013 |
| 12 | 0.0110 | 0.0057 |
| 13 | 0.0128 | 0.0014 |
| 14 | 0.0086 | 0.0013 |
| 15 | 0.0019 | 0.0003 |
| 16 | 0.0044 | 0.0022 |
| 17 | 0.0032 | 0.0008 |
| 18 |  | 0.0022 |
| 19 | 0.0020 | 0.0004 |
| 20 | 0.0101 | 0.0029 |

What is claimed is:

1. A compound of Formula (I)

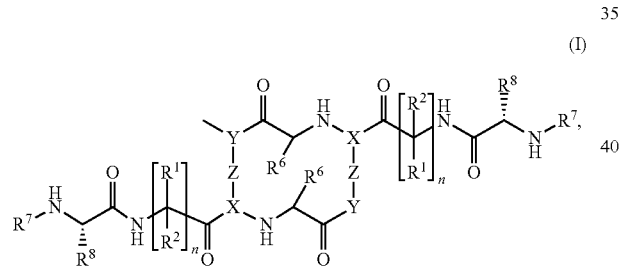

including pharmaceutically acceptable salts thereof, wherein:

each n is independently 1 or 2;

each $R^1$ is independently hydrogen, $C_1$-$C_4$ alkyl, cycloalkyl or —($C_1$-$C_4$ alkylene)-$R^4$, wherein each $R^4$ is independently hydrogen, aryl, or cycloalkyl, wherein at least one $R^1$ is other than hydrogen; and each $R^2$ is hydrogen; or $R^1$ and $R^2$ are taken together with the carbon atom to which they are commonly bound to form a cycloalkyl;

each $R^6$ is independently —($C_1$-$C_4$ alkylene)-$R^9$, wherein each $R^9$ is independently selected from hydrogen, aryl, heteroaryl and cycloalkyl; wherein any aryl, heteroaryl or cycloalkyl portion of $R^6$ is optionally substituted with up to two substituents independently selected from halo, $CF_3$, OH, $C_1$-$C_4$ alkoxy, $C_1$-$C_4$ alkenyloxy, phenyl, phenyloxy, and phenylmethyloxy; and wherein one —$CH_2$— in the —($C_1$-$C_4$ alkylene)- portion of $R^6$ is optionally replaced with —O—;

each $R^7$ is independently hydrogen or $C_1$-$C_4$ alkyl;

each $R^8$ is independently $C_1$-$C_4$ alkyl;

each X is independently selected from:

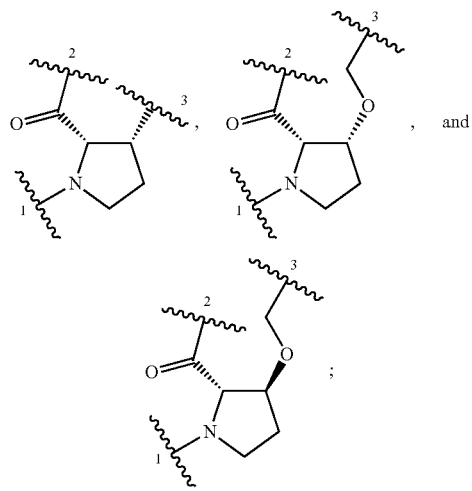

each Z is:

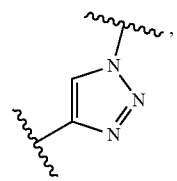 [SMILES: *c1cn(*)nn1]

wherein each -| represents a point of attachment to the compound;

each Y is:

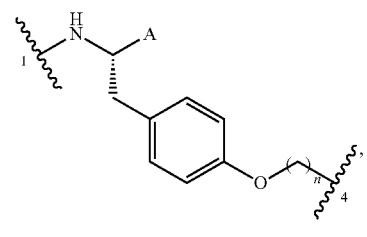

$n = 1$-$3$ wherein:

-|$^1$ represents a point of attachment to a —C=O portion of the compound;

-|$^2$ represents a point of attachment to a —NH portion of the compound;

-|$^3$ represents a first point of attachment to Z;

-|$^4$ represents a second point of attachment to Z; and each A is independently selected from

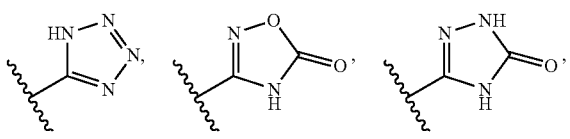

-continued

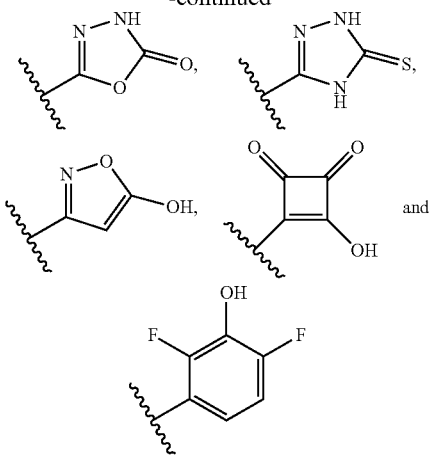

(including the various tautomeric forms).

2. The compound according to claim 1 wherein each $R^1$ is independently $C_1$-$C_4$ alkyl;

each $R^6$ is independently —($C_1$-$C_4$ alkylene)-$R^9$, wherein each $R^9$ is independently selected from hydrogen, aryl and heteroaryl;

each $R^7$ is independently selected from hydrogen and methyl;

each $R^8$ is independently selected from methyl and ethyl; and each A is independently

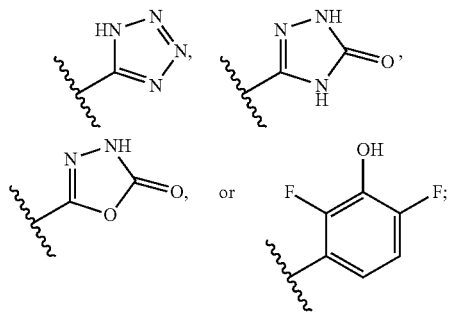 [SMILES: *c1nnn[nH]1 ; *c1n[nH]c(=O)[nH]1 ; *c1n[nH]c(=O)o1 ; *c1ccc(F)c(O)c1F]

and/or a pharmaceutically acceptable salt thereof.

3. The compound according to claim 2 wherein each $R^1$ is t-butyl;

each $R^6$ is independently —($C_1$-$C_4$ alkylene)-$R^9$, wherein each $R^9$ is aryl;

each $R^7$ is independently selected from hydrogen and methyl;

each $R^8$ is independently selected from methyl and ethyl; and each A is independently or

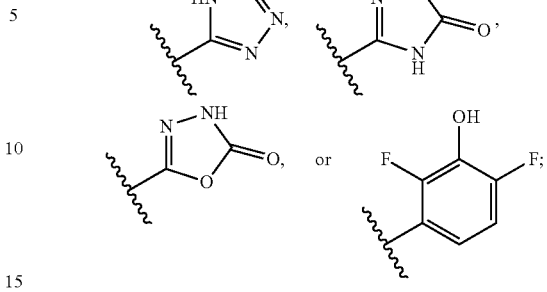

and/or a pharmaceutically acceptable salt thereof.

4. The compound according to claim 3 wherein each $R^6$ is independently —($C_1$-$C_4$ alkylene)-$R^9$, wherein each $R^9$ is naphthalenyl;

each $R^7$ is methyl;

each $R^8$ is methyl; and each A is independently

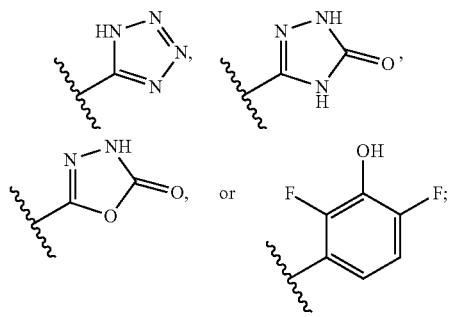

and/or a pharmaceutically acceptable salt thereof.

5. A pharmaceutical composition comprising a compound of claim 1 and a pharmaceutically acceptable carrier.

6. A pharmaceutical composition comprising a compound of claim 2 and a pharmaceutically acceptable carrier.

7. A pharmaceutical composition comprising a compound of claim 3 and a pharmaceutically acceptable carrier.

8. A method for the treatment or prevention of a proliferative disorder in a patient comprising administering to the patient a therapeutically effective amount of a compound or pharmaceutically acceptable salt thereof according to claim 1.

9. The method according to claim 8 wherein the proliferative disorder is cancer.

10. The method according to claim 9 further comprising administering to the patient a therapeutically effective amount of a chemotherapeutic agent prior to, simultaneously with or after administration of the compound.

11. A method for inducing apoptosis in a cancer cell comprising contacting the cell with a compound or pharmaceutically acceptable salt thereof according to claim 1.

* * * * *